(12) United States Patent
Renzi et al.

(10) Patent No.: US 8,202,851 B2
(45) Date of Patent: Jun. 19, 2012

(54) ANTISENSE OLIGONUCLEOTIDES FOR TREATING ALLERGY AND NEOPLASTIC CELL PROLIFERATION

(75) Inventors: Paolo Renzi, Westmount (CA); Khalid Zemzoumi, Montreal (CA)

(73) Assignee: Topigen Pharmaceuticals Inc., Montreal (CA)

( * ) Notice: Subject to any disclaimer, the term of this patent is extended or adjusted under 35 U.S.C. 154(b) by 0 days.

(21) Appl. No.: 13/301,183

(22) Filed: Nov. 21, 2011

(65) Prior Publication Data

US 2012/0065249 A1    Mar. 15, 2012

Related U.S. Application Data

(63) Continuation of application No. 11/666,647, filed as application No. PCT/CA2005/001656 on Oct. 27, 2005, now Pat. No. 8,119,790.

(60) Provisional application No. 60/623,206, filed on Oct. 29, 2004.

(51) Int. Cl.
*C12N 15/11* (2006.01)
*C07H 21/02* (2006.01)
*C07H 21/04* (2006.01)

(52) U.S. Cl. .................. 514/44; 536/24.1; 536/24.5

(58) Field of Classification Search .............. 514/44; 536/24.1, 24.5
See application file for complete search history.

(56) References Cited

U.S. PATENT DOCUMENTS

| | | | |
|---|---|---|---|
| 3,337,530 A | 8/1967 | Hanze, et al. | |
| 4,880,635 A | 11/1989 | Janoff et al. | |
| 4,906,477 A | 3/1990 | Kurono et al. | |
| 4,911,928 A | 3/1990 | Wallach | |
| 4,917,951 A | 4/1990 | Wallach et al. | |
| 4,920,016 A | 4/1990 | Allen et al. | |
| 4,921,757 A | 5/1990 | Wheatley et al. | |
| 5,807,708 A | 9/1998 | Falb | |
| 5,856,466 A | 1/1999 | Guinosso et al. | |
| 5,889,178 A | 3/1999 | Gregson et al. | |
| 5,925,624 A | 7/1999 | Gregson et al. | |
| 6,025,339 A | 2/2000 | Nyce et al. | |
| 6,175,004 B1 | 1/2001 | Ross et al. | |
| 2003/0087845 A1 | 5/2003 | Nyce et al. | |

FOREIGN PATENT DOCUMENTS

| | | |
|---|---|---|
| WO | 9622371 | 7/1996 |
| WO | 9632481 | 10/1996 |
| WO | 9636291 | 11/1996 |
| WO | 9720926 | 6/1997 |
| WO | 9722698 | 6/1997 |
| WO | 9723244 | 7/1997 |
| WO | 9728190 | 8/1997 |

(Continued)

OTHER PUBLICATIONS

Lamkhioued, B. et al., "The CCR3 Receptor is Involved in Eosinophil Differentiation and is Up-Regulated by Th2 Cytokines in CD34+ Progenitor Cells." J Immunol. 169:537-547, 2002.

(Continued)

*Primary Examiner* — Terra Cotta Gibbs
(74) *Attorney, Agent, or Firm* — Nixon Peabody LLP; David S. Resnick; Leena H. Karttunen Contarino

(57) ABSTRACT

Antisense oligonucleotides for treating and/or preventing at least one of asthma, allergy, hypereosinophilia, general inflammation and cancer are provided. The oligonucleotides are directed against nucleic acid sequences coding for a receptor selected from the group consisting of a CCR3 receptor and a common sub-unit of IL-3, IL-5 and GM-CSF receptors.

4 Claims, 25 Drawing Sheets

FOREIGN PATENT DOCUMENTS

| | | |
|---|---|---|
| WO | 9741154 | 11/1997 |
| WO | 9741225 | 11/1997 |
| WO | 9902732 | 1/1999 |
| WO | 9913886 | 3/1999 |
| WO | 9966037 | 12/1999 |
| WO | 9967378 | 12/1999 |
| WO | 0009525 | 2/2000 |
| WO | 0012563 | 3/2000 |
| WO | 0062736 | 10/2000 |
| WO | 0220773 | 3/2002 |
| WO | 03004511 | 1/2003 |
| WO | 03037909 | 5/2003 |
| WO | 03064441 | 8/2003 |

OTHER PUBLICATIONS

Allakhverdi, Z. et al., Am J Respir Care Med, 165:1015-1021 (2002). "Inhibition of Antigen-induced Eosinophilia and Airway Hyper-responsiveness by Antisense Oligonucleotides Directed against the Common Beta Chain of IL-3, IL-5, GM-CSF Receptors in a Rat Model of Allergic Asthma."
Allakhverdi, Z. et al., Ann. N. Y. Acad. Sci., 1082:62-73 (2006). "Multitargeted Approach Using Antisense Oligonucleotides for the Treatment of Asthma."
Fortin, M. et al., Oligonucleotides, 16:203-212 (2006). "Effects of Antisense Oligodeoxynucleotides Targeting CCR3 on the Airway Response to Antigen in Rats."
Jubinsky, P.T. et al., Blood, 90(5):1867-1873 (1997). "The Beta Chain of the Interleukin-3 Receptor Functionally Associates with the Erythropoietin Receptor."
Adachi et al. (1995) Am. J. Respir. Crit. Care Med. 151:618-623.
Adachi et al. (2004) Biochem. Biophys. Res. Comm. 320:292-296.
Agrawal et al. (2000) Mol. Med. tODAY 6:72-81.
Ali et al. (2001) Am. J. Respir. Critic. Care Med. 163:989-993.
Bailly et al. (1995) Nuc. Acids Res. 23:885-92.
Bailly et al. (1996) Proc. Natl. Acad. Sci. 93:13623-8.
Balow et al. (1998) Nuc. Acids Res. 26(14): 3350-3357.
Balzarini et al. !1987) Biochem. Biophys. Res. Comm. 145:269-76.
Barnes et al. (2003) Cytokine Growth Factor Rev. 14:511-522.
Bide et al. (2000) J. Appl. Toxicol. 20:273-290.
Blease (2003) Expert Opin. Emerg. Drugs 8:71-81.
Cheng (1995) Ann. Rev. Biophys. Biomol. Struct. 24:293-318.
Chollett et al (1988) Nuc. Acids Res. 16: 305-17.
Crooke (1995) Hematoloic Pathology 9:59-72.
Crooke (1998) Antisense Research and Applications, CRC Press, 1-50.
Devos et al. (1995) J. Leukocyte Biol. 57:813-819.
Eckstein (1985) Ann. Rev. Biochem. 54:367-402.
Freeburn et al. (1997) Exp. Hematol. 25:306-311.
Goodchild (2004) Curr. Opin. Mol. Ther. 6:120-128.
Green et al. (2000) J. Am. Coll. Surg. 191(1):93-105.
Hare et al (2003) Mol. Biol. Evol. 20:969-978.
Hayashida et al. (1990) Proc. Natl. Acad. Sci. 87-9655-9659.
Hanze et al. (1968) Biochemistry 7(3):932-939.
Hoheisel et al (1990) FEBS Letters 274:103-6.
Ikizawa et al. (1995) Clin. Exp. Immunol. 100: 383-389.
Jen et al. (2000) Stem Cells 18: 307-319.
John et al. (2003) Sarcoidosis Vasc. Diffuse Lung Dis. 20:180-189.
Khudyakov et al. (1978) Virology 88:8-18.
Lamkhioued et al. (1997) J. Immunol. 159:4593-4601.
Mann et al. (1986) J. Appl. Physiol. 61:1667-76.
Nandanan et al. (1999) J. Med. Chem. 42:1625-1638.
Oddera et al. (1998) Lung 176:237-247.
Ortoleva-Donnelly et al. (1998) RNA 4:498-519.
Ponath et al. (1996) J. Exp. Med. 183:2437-2448.
Rackwitz et al. (1977) Eur. J. Briochem. 72:191-200.
Rahman et al. (2004) Genomics 83:76-84.
Renzi et al. (1992) Am. Rev. Respir. Dis. 146:163-9.
Saladino et al. (1996) Tetrahedron 52(19): 6759-6780.
Sanghvi et al (1991) Nucleosides Nucleotides 10: 345-346.
Santalucia et al. (1991) J. Am. Chem. Soc. 113:4313-4322.
Schuh et al. (2003) Cytokine Growth Factor Rev. 14:503-510.
Strauss-Soukup et al. (2000) J. Mol. Biol. 302:339-358.
Strobel et al. (1997) Proc. Natl. Acad. Sci. 94:2903-2908.
Templin et al. (2000) Antisense Nucl. Acid Drug Dev. 10:359-368.
Tiffany et al. (1996) J. Immunol. 160:1385-1392.
Trentin et al. (2004) Blood 104:502-508.7, 2002.
Uhlmann et al. (1990) Am. Chem. Soc. vol. 90, No. 4: 556-5573.
Urban et al. (2003) Farrmaco 58:243-258.
Walsh et al. (1997) Clin. Exp. Allergy 27:482-487.
Genbank Accession No. U49727, Oct. 4, 1996.
Genbank Accession No. M59941, May 1994.
Allakhverdi et al. (2002) Am. J. Respir. Crit. Care Med. 165:1015-1021.
Allam et al. (2001) Antisense & Nucleic Acid Drug Development 11:289-300.
Buhr et al. (1996) Nucleic Acids Research 24 (15): 2974-2980.
Ohnishi et al (1993) J. Allergy Clin. Immunol. 92:607-615.

Figure 1.

Figure 10A.
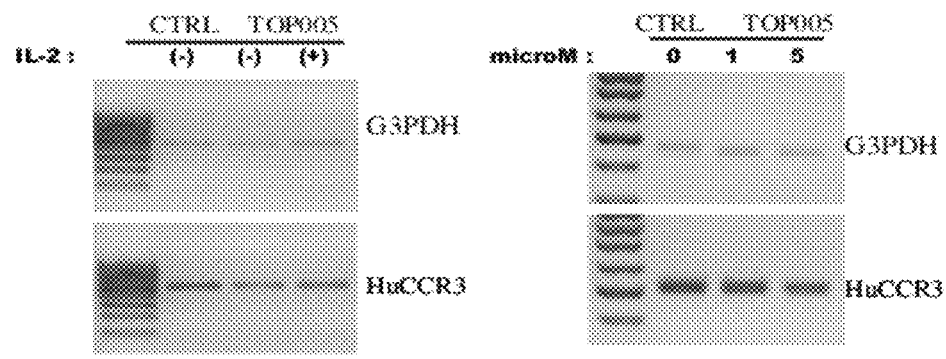
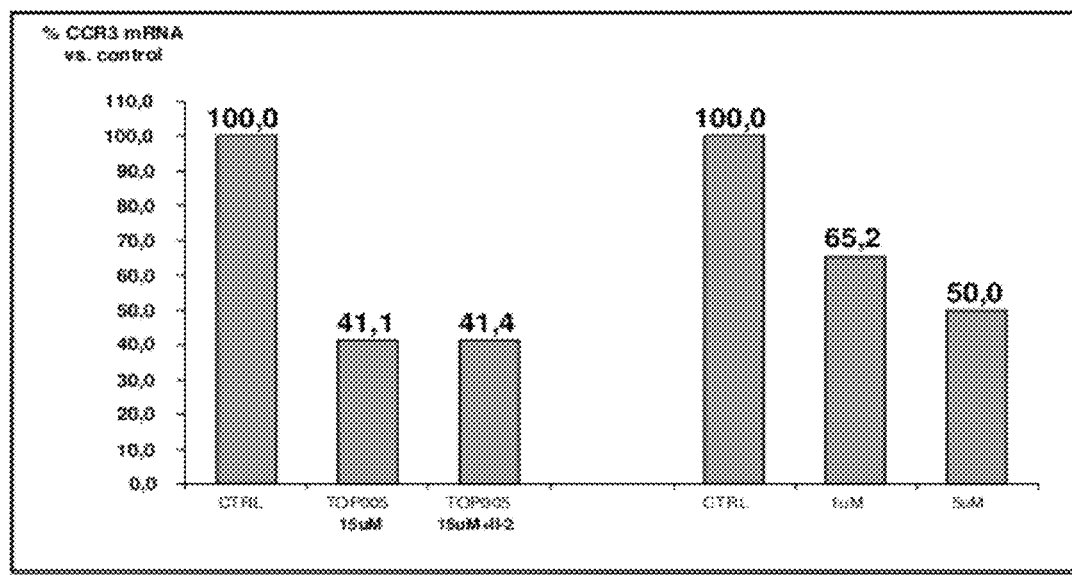
Figure 10B.

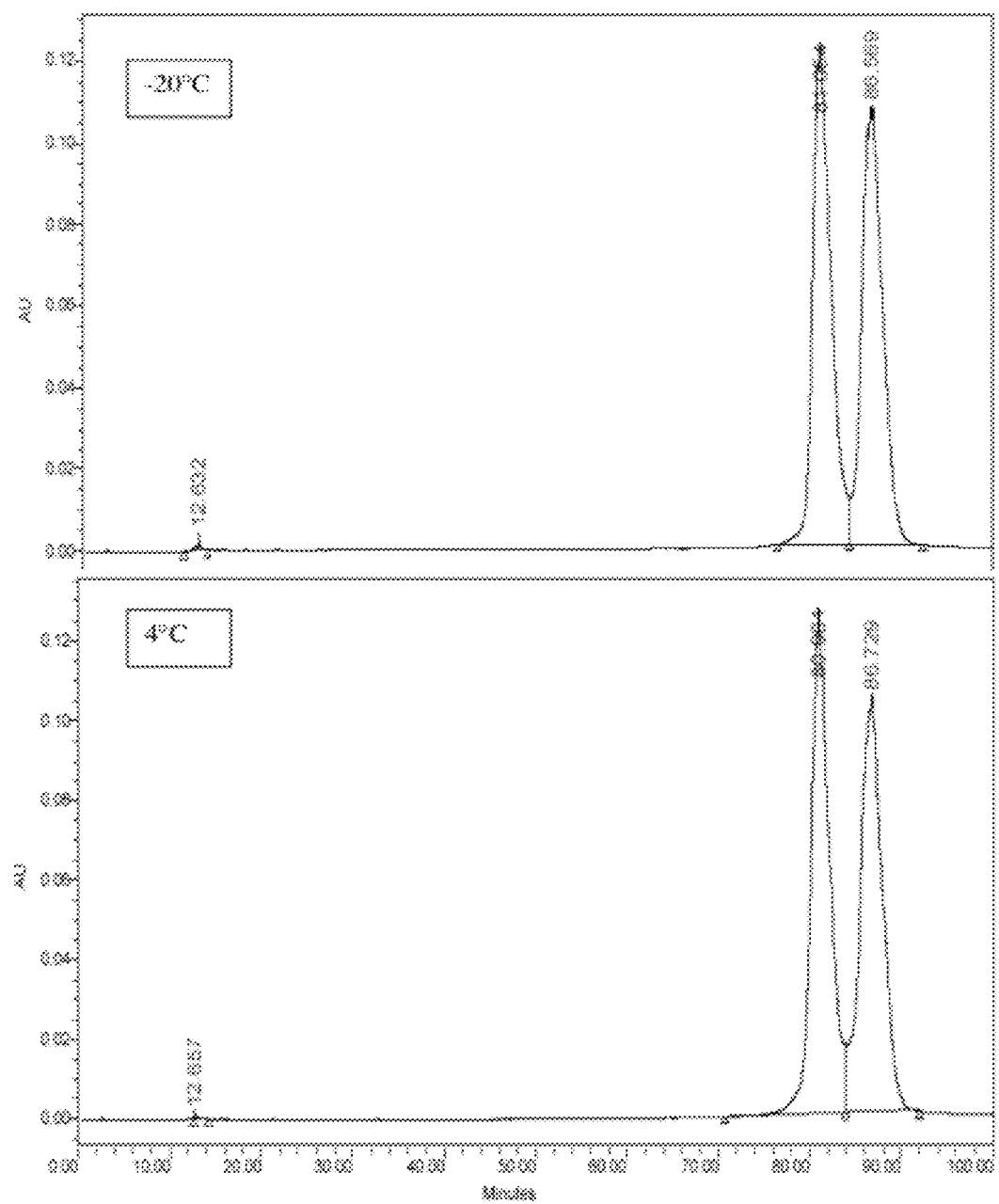
Figure 17A1

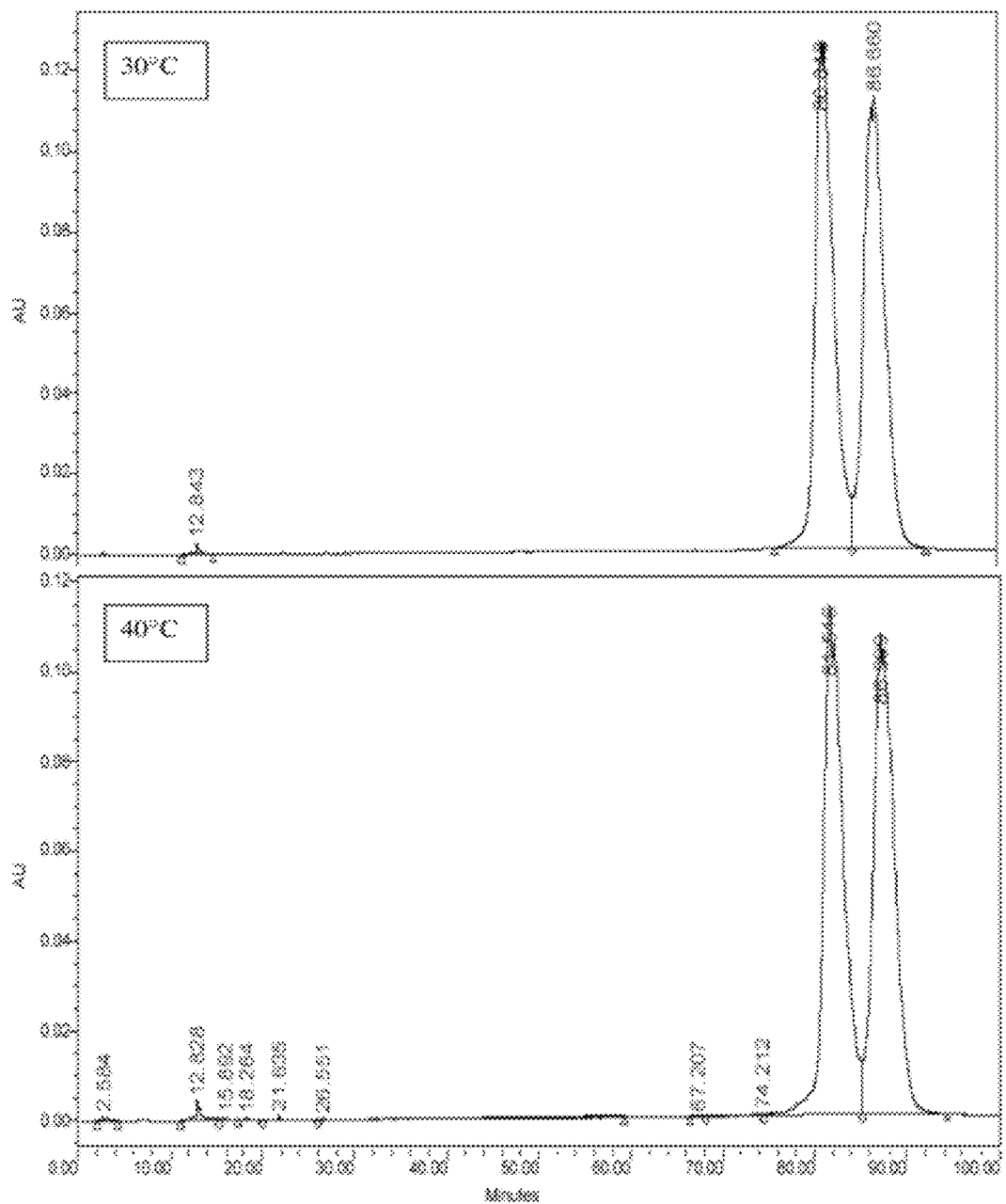
Figure 17A2

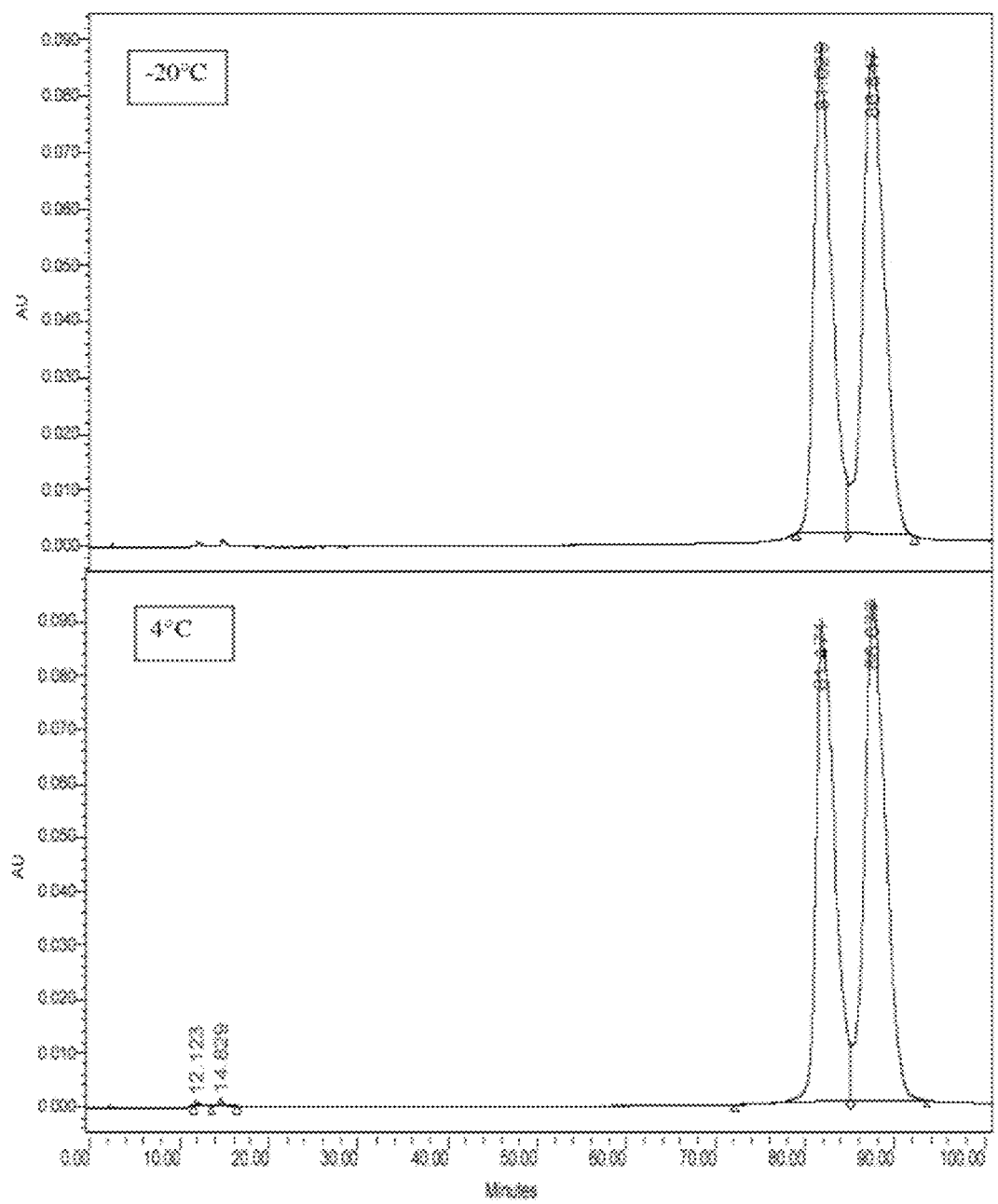
Figure 17B1

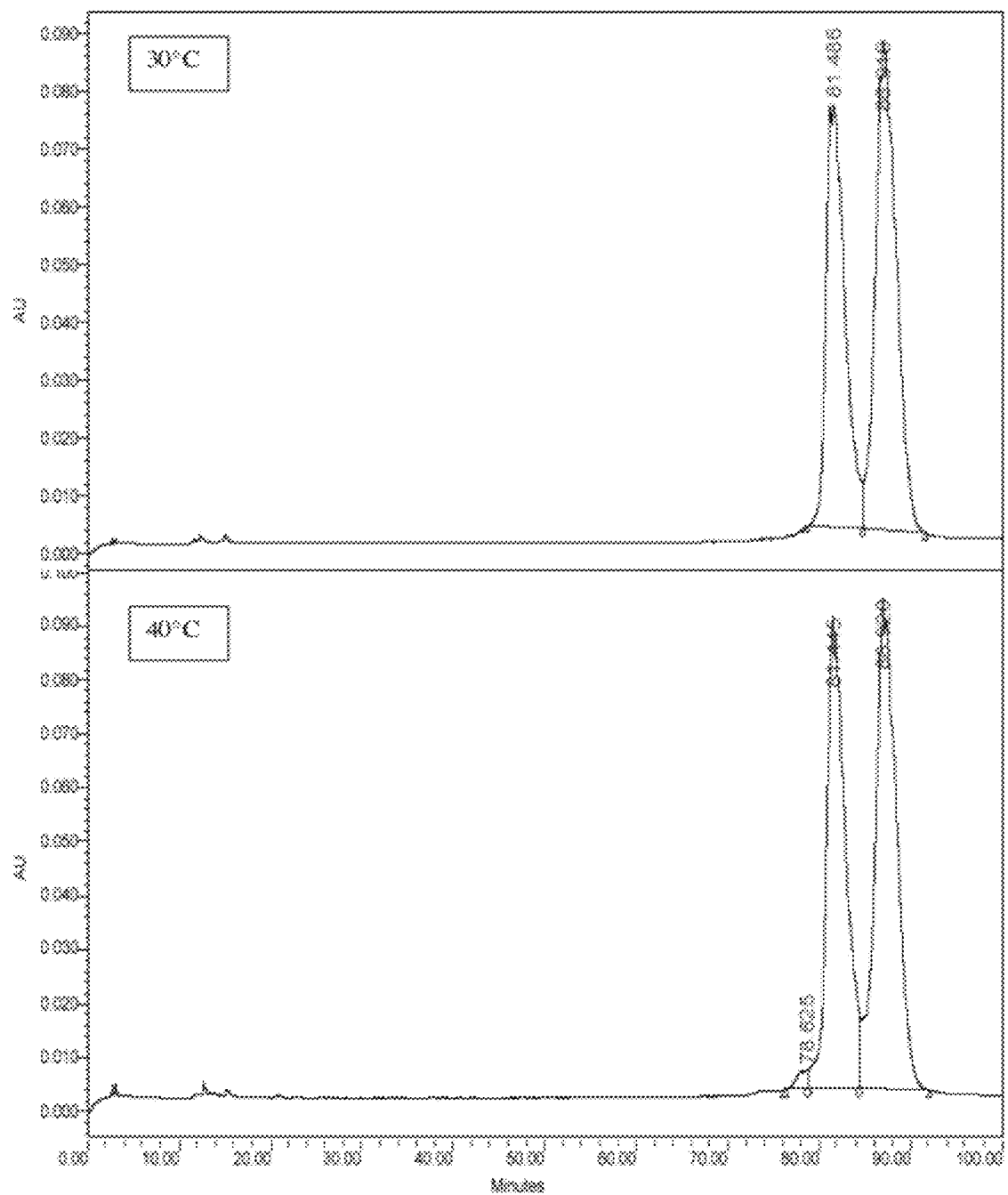
Figure 17B2

ANTISENSE OLIGONUCLEOTIDES FOR TREATING ALLERGY AND NEOPLASTIC CELL PROLIFERATION

CROSS REFERENCE TO RELATED APPLICATIONS

This application is a Continuation Application of U.S. application Ser. No. 11/666,647, filed Nov. 30, 2007, issued as U.S. Pat. No. 8,119,790, which is a 371 National Stage of International Application No. PCT/CA2005/001656 filed on Oct. 27, 2005, which designated the U.S., and which claims benefit under 35 U.S.C. §119(e) of U.S. Provisional Application No. 60/623,206 filed on Oct. 29, 2004.

FIELD OF THE INVENTION

The invention relates to the use of antisense oligonucleotides directed against specific cellular receptors, alone or in combination, in order to inhibit general inflammation, including inflammation associated with asthma and allergy, and hypereosinophilia. The invention also relates to the use of antisense oligonucleotides to inhibit neoplastic cell proliferation such as cancer.

BACKGROUND OF THE INVENTION

Antisense oligonucleotides are a new class of pharmaceuticals. In general, antisense refers to the use of small, synthetic oligonucleotides, with the same constituents as that found in human DNA or RNA. The antisense oligonucleotides are designed as a complementary sequence of a part of a gene they are targeting in order to be able to adhere to this sequence and inhibit gene expression. Gene expression is inhibited through hybridization of an antisense oligonucleotide to a specific messenger RNA (mRNA) sense target according to the Watson-Crick base pairing in which adenosine and thymidine (uracile in mRNA) or guanosine and cytidine interact through hydrogen bonding. Two mechanisms can account for these effects, the first being hybridization with impaired translation of targeted mRNA, the second being the induction of RNase H or similar enzymes with degradation of mRNA. A major advantage of this strategy is the specificity of action with the potential for less side effects and toxicity, especially when applied to the site of action (topical treatment). This therapeutic strategy could potentially be applied to any disease where an over-expression of one or several genes is believed to cause the presence or persistence of the disease. As a result, there have been numerous studies of antisense oligonucleotides as therapeutic agents for cancer and viral diseases.

Antisense oligonucleotides can be used to inhibit interleukin (IL)-6 receptor expression and thus the effects of the acute inflammatory mediator interleukin-6 on cells. Few studies have been conducted to assess whether antisense oligonucleotides can be employed to inhibit other receptors on cells that are involved in inflammation, including, but not limited to inflammation associated with asthma and inflammation associated with atopic diseases and allergy or on cancerous cells.

Asthma is a disease that affects 5 to 10% of the population that has doubled in prevalence in the last 25 years. This increase has been noted especially in infants after a viral infection of the airways (bronchiolitis), in children and in occupational induced asthma. The recurrent breathing problems associated with asthma are often triggered by allergens but the exact cause of asthma is not yet known. However, it is believed that agents such as viruses are involved in the perpetuation of the abnormal inflammation that is found in the airways of patients with asthma and thus the persistence of the disease.

For this reason the current recommendations for first line therapy of asthma is a potent anti-inflammatory medication such as those containing corticosteroids and anti-leukotrienes. Although this therapy is effective in many patients, some patients are resistant to corticosteroids. This medication is also a potent immunosuppressive with long term side effects and has not been shown to be effective in the prevention of allergy or asthma. Anti-leukotrienes have some effect in allergy and asthma but are not as effective as corticosteroids.

Several inflammatory mediators play a role in the appearance and perpetuation of inflammation in the airways of patients with asthma. Some mediators attract the inflammatory cells into the airways either through chemotaxis of eosinophils (the chemokines: RANTES, eotaxins 1, 2, 3, MCP-3, 4 that act mostly in asthmatic inflammation through a receptor called CCR3) or through endothelial cell activation (IL-4, -13). Other mediators cause the priming and increased survival of inflammatory cells in the airways (IL-3, -4, -5, GM-CSF). These mediators thus consist of either specific chemokines for eosinophils or of cytokines of the T helper lymphocyte type 2 phenotype (Th2: IL-3, -4, -5, -6, -9, -10, -13 and GM-CSF), (John A E. and Lukacs N W., 2003 Sarcoidosis Vasc Diffuse Lung Dis., 20:180-189; Blease et al., 2003, Expert Opin Emerg Drugs. 8:71-81). An improvement, in asthma and general respiratory inflammation, has been shown when there is a decrease in these inflammatory mediators in the airways.

Allergy is a hypersensitivity to an allergen causing an undesirable immune response. Allergy is a disease that is extremely prevalent, for example atopic rhinitis and conjunctivitis affect around 30% of the population. Allergy is characterized by abnormal IgE production and inflammation to an allergen. In the presence of IgE and allergen, effector cells, such as the mast cells degranulate and release inflammatory mediators leading to the recruitment of the same inflammatory cells that are found in asthma. In allergic rhinitis (i.e. hayfever), allergic conjunctivitis, nasal polyposis, chronic sinusitis and eczema, such as atopic dermatitis, one finds the same excess in inflammatory mediators as those present in asthma. IL-4 and IL-13 are necessary for the production of IgE and the induction of the cells with a Th2 phenotype (Barnes P J., 2003, Cytokine Growth Factor Rev. 14:511-522; Schuh et al., 2003, Cytokine Growth Factor Rev. 2003, 14:503-510). Atopic diseases is a generic name for allergic diseases which are developed by exposure to allergens, especially in individuals with a genetic propensity for being easily sensitized to allergens. Individuals having these predisposing factors easily develop an abnormal immune response to alimentary antigens and inhalants. Some specific examples of allergic diseases are bronchial asthma, atopic dermatitis, urticaria, allergic rhinitis, allergic conjunctivitis and allergic enterogastritis.

A neoplasm is an abnormal tissue growth that is uncontrollable and progressive. A malignant neoplasm is often characterized as a cancer. Cancer is the second leading cause of death in humans and is a general term for more than 100 diseases characterized by abnormal proliferation of immortalized cells. One of the mechanisms that is involved in the persistence and increase in these cells is by the release of growth factors that act through receptors and lead to cellular proliferation. Amongst these growth factors, GM-CSF has been shown to be an important growth factor for several tumour cells. The chemokine receptor CCR3 was recently characterized in malignant B lymphocytes recovered from patients with chronic lymphocytic leukemia (CLL) and with hairy cell leukemia (HCL), (Trentin et al., 2004, Blood, 104, 502-508). Indeed, the transactivation of Epidermal Growth Factor Receptor (EGFR) through CCR3 chemokine receptor was found to be a critical pathway that elicits MAP kinase activation and cytokine production in bronchial epithelial cells (Adachi et al., 2004, Biochem. Biophys. Res. Commun. 320, 292-396). The inhibition of proliferation of cancerous cells by blocking the receptors for growth factors and/or for chemokines, may be important in the therapy of certain cancers.

Eosinophils are a type of white blood cell. They are granular leukocytes with a nucleus that usually has two lobes connected by a slender thread of chromatin, and cytoplasm containing course, round granules that are uniform in size and stainable by eosin. Hypereosinophilia is characterized by an increased number of eosinophils, often associated with allergies, asthmas and infections.

Some use of oligonucleotides directed against specific nucleic acid sequences coding for receptors, in order to inhibit inflammatory reactions is known. PCT Application No. WO 99/66037 by Renzi describes antisense oligonucleotides that are used for treating and/or preventing asthma, allergy, hypereosinophilia, general inflammation and cancer. Specifically, the oligonucleotides of Renzi are directed against nucleic acid sequences coding for a CCR3 receptor, a common sub-unit of IL-4 and IL-3 receptors, or a common sub-unit of IL-3, IL-5 and GM-CSF receptors. Among others, an antisense oligonucleotide identified as 107A (5'-GGGTCTGCAGCGGGATGGT-S') (SEQ ID NO: 43), directed against the common, beta (β) sub-unit of the IL-3, IL-5 and GM-CSF receptor, is disclosed therein.

For potential clinical uses, antisense oligonucleotides should exhibit stability against degradation by serum and cellular nucleases, show low non-specific binding to serum and cell proteins, exhibit enhanced recognition of the target mRNA sequence, demonstrate cell-membrane permeability and elicited cellular nucleases when complexed with complementary mRNA. It is well documented that oligonucleotides containing natural sugars (D-ribose and D-2-deoxyribose) and phosphodiester (PO) linkages are rapidly degraded by serum and intracellular nucleases, which limit their utility as effective therapeutic agents. Chemical strategic modifications have been described for oligonucleotides in order to improve their stability and efficacy as therapeutic agents. The main chemical changes included, modification of the sugar moiety, the base moiety, and/or modification or replacement of the internucleotide phosphodiester linkage. To date the most widely studied analogues are the phosphorothioate (PS) oligodeoxynucleotides, in which one of the non-bridging oxygen atoms in the phosphodiester backbone is replaced with a sulfur (Eckstein F., 1985, Ann. Rev. Biochem., 54: 367-402). Several antisense oligonucleotide generations have been developed and used for in vitro and for in vivo studies (Goodchild J., 2004, Curr. Opin. Mol. Ther., 2004, 6:120-128; Urban E. and R. Noe C R., 2003, Farmaco. 58:243-258). Recently, Renzi et al. described the use of 2',6'-diaminopurine (DAP) and analogs thereof in nucleic molecules for anti-inflammatory compositions (PCT Application No. WO 03/004511 A2). Also described in this reference is the preparation of nucleic molecules having an increased in vivo physiological efficiency and a reduced toxicity as compared to oligonucleotides without DAP. Renzi et al. further teaches that DAP substitution is particularly useful in preparing oligonucleotides directed to pulmonary/respiratory diseases such as cystic fibrosis, asthma, chronic bronchitis, chronic obstructive lung disease, eosinophilic bronchitis, allergies, allergic rhinitis, pulmonary fibrosis, adult respiratory distress syndrome, sinusitis, respiratory syncytial virus or other viral respiratory tract infection and cancer.

It would be desirable to have further antisense oligonucleotides directed against at least one specific common receptor for either Th2 cytokines or receptors for mediators that attract cells that respond to Th2 cytokines, in order to inhibit the inflammatory reaction that is present in asthma or allergy and to inhibit neoplastic cell proliferation.

It would also be highly desirable to have further antisense oligonucleotides directed against nucleic acid sequences coding for receptors so that by inhibiting these receptors these oligonucleotides could be employed in the therapy and/or prevention of asthma, allergy, hypereosinophilia, general inflammation and cancer.

SUMMARY OF THE INVENTION

The present invention provides the use of antisense oligonucleotides, directed against at least one common subunit of a cellular receptor, such as, for example, the common beta subunit for IL-3, IL-5, and GM-CSF receptors or the chemokine receptor CCR3, in order to treat and/or prevent at least one of asthma, allergy, hypereosinophilia, general inflammation and cancer.

In another aspect, the present invention provides antisense oligonucleotides directed against a nucleic acid sequence coding for the common beta subunit of the IL-3, IL-5 and GM-CSF receptors so that by inhibiting these receptors they may be employed in the treatment and/or prevention of at least one of asthma, allergy, hypereosinophilia, general inflammation and cancer.

The present invention also provides antisense oligonucleotides directed against a nucleic acid sequence coding for the CCR3 receptor for chemokines so that by inhibiting this receptor they may be employed in the treatment and/or prevention of at least one of asthma, allergy, hypereosinophilia, general inflammation and cancer.

The present invention also provides therapeutically effective compositions comprising at least one antisense oligonucleotide directed against nucleic acid sequences coding for the common beta subunit of IL-3, IL-5, and GM-CSF, or the CCR3, receptors for the treatment and/or prevention of at least one of asthma, allergy, hypereosinophilia, general inflammation and cancer.

The present invention also provides therapeutically effective compositions comprising two antisense oligonucleotides each directed against nucleic acid sequences coding for the common beta subunit of IL-3, IL-5, and GM-CSF, or the CCR3, receptors for an improved effect in the treatment and/or prevention of at least one of asthma, allergy, hypereosinophilia, general inflammation and cancer.

According to another aspect, the present provides methods for treating and/or preventing at least one of asthma, allergy, general inflammation and cancer comprising administering one or more antisense oligonucleotides directed against at least one common subunit of a cellular receptor, such as the common beta subunit for IL-3, IL-5, and GM-CSF or the CCR3, receptors.

The present invention seeks to provide antisense oligonucleotides for any of the foregoing as well as chemically modified antisense oligonucleotides modified in known ways that have improved stability in the body while exhibiting improved effectiveness and lower toxicity.

According to another aspect of the present invention, an antisense oligonucleotide for treating and/or preventing at least one of asthma, allergy, hypereosinophilia, general inflammation and cancer is provided. The oligonucleotide is directed against a nucleic acid sequence coding for a receptor selected from the group consisting of a CCR3 chemokine receptor and a common beta-sub-unit of IL-3, IL-5 and GM-CSF receptors, and has a sequence selected from the group consisting of SEQ ID NO. 1, SEQ ID NO. 13 and SEQ ID NO. 14.

According to another aspect of the invention, use of the at least one oligonucleotide for treating and/or preventing at least one of asthma, allergy, hypereosinophilia, general inflammation and cancer, is provided. Preferably, oligonucleotides comprising both sequences SEQ ID NO. 13 and SEQ ID NO. 14 are used.

According to another aspect of the invention, a pharmaceutical composition for treating and/or preventing at least one of asthma, allergy, hypereosinophilia, general inflammation and cancer is provided comprising the at least one oligonucleotide in association with a pharmaceutically acceptable carrier. Preferably, the at least one oligonucleotide comprises both SEQ ID NO. 13 and SEQ ID NO. 14.

According to another aspect of the invention, a use of the pharmaceutical composition, for treating and/or preventing at least one of asthma, allergy, hypereosinophilia, general inflammation and cancer is provided.

According to another aspect of the invention, a method for treating and/or preventing at least one of asthma, allergy, hypereosinophilia, general inflammation and cancer is provided comprising the step of administering an effective amount of (i) the at least one oligonucleotide or (ii) the pharmaceutical composition comprising the at least one oligonucleotide in association with a pharmaceutically acceptable carrier.

The invention herein also relates to modifications to an antisense oligonucleotide(s) that do not significantly adversely affect their ability to reduce activity or inhibit expression of a target protein, but which may enhance this ability.

BRIEF DESCRIPTION OF THE DRAWINGS

These and other features of the preferred embodiments of the invention will become more apparent in the following detailed description in which reference is made to the appended drawings wherein:

FIG. 1A shows the sequence alignment of three clones obtained from PCR amplification of the Cynomolgus monkey common beta-chain for IL-3, IL-5 and GM-CSF, receptor genes with the corresponding human, chimpanzee, pork, rat and mouse, orthologues surrounding the human TOP004 complement sequence.

FIG. 1B shows the predicted amino acid sequences (SEQ ID NO: 38 human protein (pt), SEQ ID NO: 44 human nucleotide (nt); SEQ ID NO: 38 *Pan troglydytes* pt, SEQ ID NO: 45 *Pan troglydytes* nt; SEQ ID NO: 37 *Macaca Fascicularis* pt, SEQ ID NO: 46 *Macaca Fascicularis* nt; SEQ ID NO: 40 *Cavia porcellus* pt, SEQ ID NO: 47 *Cavia porcellus* nt; SEQ ID NO: 42 *Rattus norvegicus* pt, SEQ ID NO: 48 *Rattus norvegicus* nt; SEQ ID NO: 41 *Mus musculus* pt, SEQ ID NO: 49 *Mus musculus* nt) of the translated region surrounding TOP004 complementary segment in cloned Cynomolgus monkey, human, chimpanzee (AADA01213660—SEQ ID NO. 63), pork (U94688.1—SEQ ID NO. 60), rat (NM_133555.1—SEQ ID NO. 61) and mouse (NM_007780.1—SEQ ID NO. 62), common beta-chain DNA sequences.

FIG. 2A shows the reduced beta-chain ($\beta_c$) mRNA expression by varying concentrations of TOP004 in cynomolgus monkey PBMC as compared to untreated cells.

FIG. 2B shows the reduced CCR3 mRNA expression by varying concentrations of TOP005 in cynomolgus monkey PBMC as compared to untreated cells.

FIG. 10 shows the effect of TOP005 on mRNA expression in human PBMC. Gels showing G3PDH and CCR3 expression are shown above the bar graph. The ratio of CCR3 mRNA expression to G3PDH, normalized for controls is presented on the bottom.

FIGS. 17A1, 17A2, 17B1 and 17B2 show the chemical stability of ASM8 after storage under different temperatures and later eluted using DEAE anion exchange chromatography.

DETAILED DESCRIPTION OF THE INVENTION

Several inflammatory mediators play a role in the appearance and perpetuation of inflammation in the airways of patients with asthma. Some mediators attract the inflammatory cells into the airways either through chemotaxis of eosinophils. Many of these chemokines act mostly in asthmatic or allergic inflammation through the CCR3 receptor. Other mediators cause the priming and increased survival of inflammatory cells in the airways or skin such as IL-3, IL-5, and GM-CSF. An improvement in asthma has been shown when there is a decrease in these inflammatory mediators in the airways.

Furthermore, cancer, characterized by abnormal proliferation of immortalized cells, can be caused by the release of inflammatory mediators and/or growth factors that act through receptors and lead to cellular proliferation. Amongst these, GM-CSF has been shown to be an important growth factor for several tumor cells. The chemokine receptor CCR3 was characterized in malignant B lymphocytes recovered from patients with chronic lymphocytic leukemia (CLL) and with hairy cell leukemia (HCL), (Trentin et al., 2004, Blood, 104, 502-508). Indeed, the transactivation of EGFR through CCR3 was found a critical pathway that elicits MAP kinase activation and cytokine production in bronchial epithelial cells (Adachi et al., 2004, Biochem. Biophys. Res. Commun. 320, 292-396). The inhibition of proliferation and metastasis of cancerous cells by blocking the receptors for growth factors or the chemokine receptor CCR3 could be important in the therapy of certain cancers.

In one embodiment of the invention, a novel antisense oligonucleotide identified as 828 (5'-GTTACTACTTCCAC-CTGCCTG-3', (SEQ ID NO. 1)) and directed against the CCR3 chemokine receptor is provided. The examples disclosed herein show that 828 is effective at decreasing or blocking CCR3 mRNA expression in human cell lines.

In another embodiment of the invention, novel antisense oligonucleotides TOP004 and TOP005 based on the previously disclosed 107A and the above 828 are provided. TOP004 (5'-GGGTCTGCXGCGGGXTGGT-3' (SEQ ID NO. 13) where X represents a DAP modification of an adenosine residue), as with 107A, is a 19-mer directed against the mRNA of the common beta (β)-chain of the IL-3, IL-5, and GM-CSF receptors. TOP005 (5'-GTTXCTXCTTCCX-CCTGC CTG-3' (SEQ ID NO. 14), where X represents a DAP modification of an adenosine residue), as with 828, is a 21-mer directed against the mRNA of the chemokine receptor CCR3. A composition comprising both TOP004 and TOP005 is identified as a part of ASM8.

Figure 1:
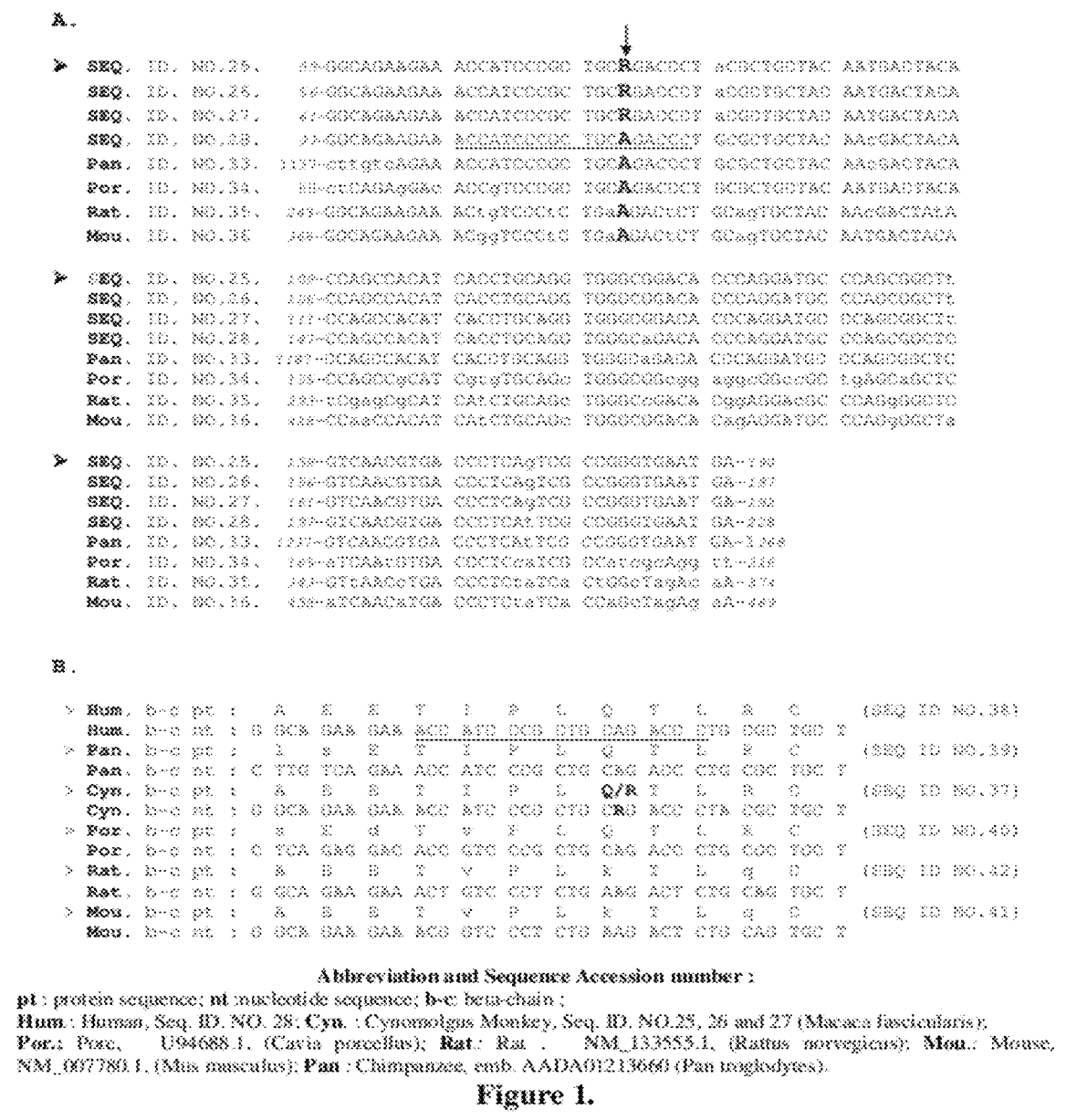
Figure 2:
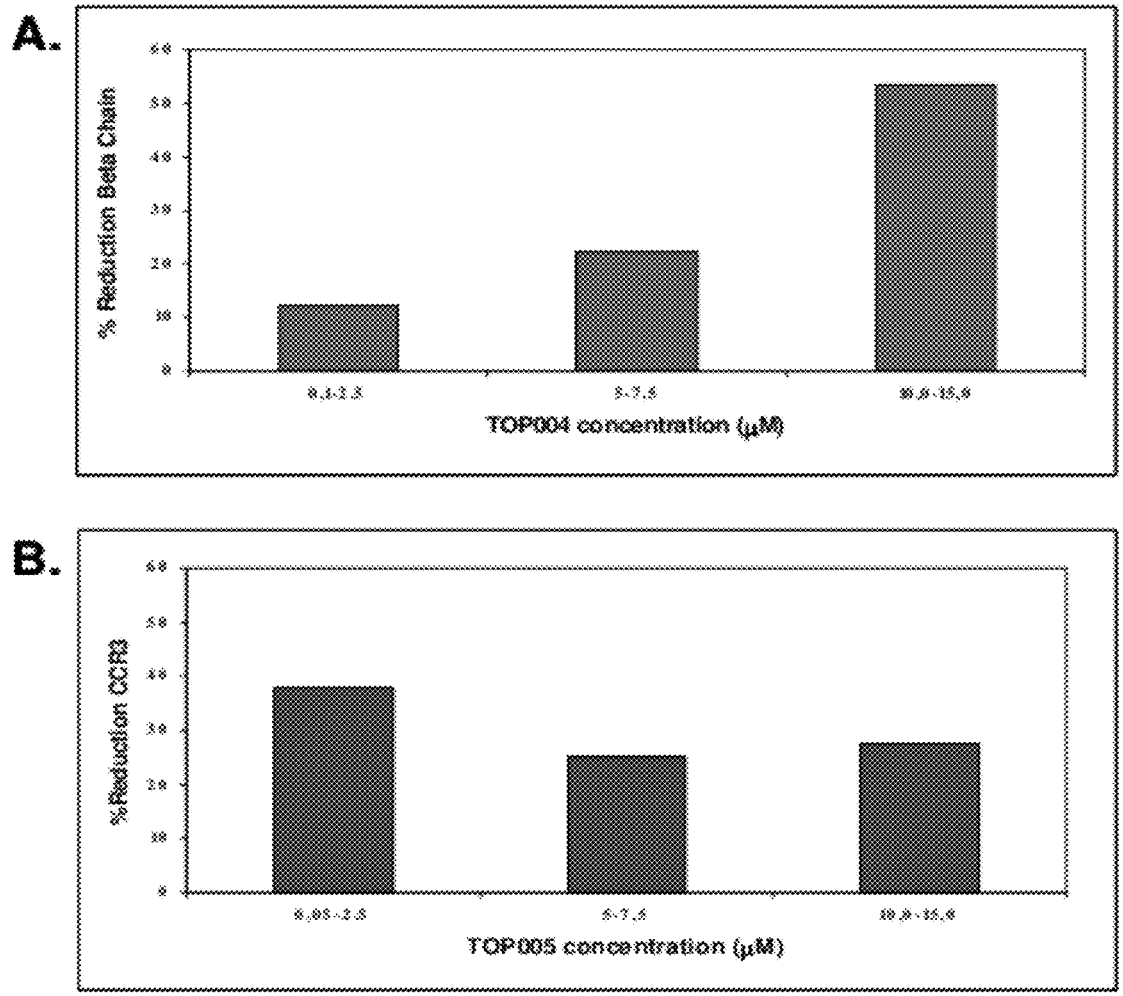
Figure 3:
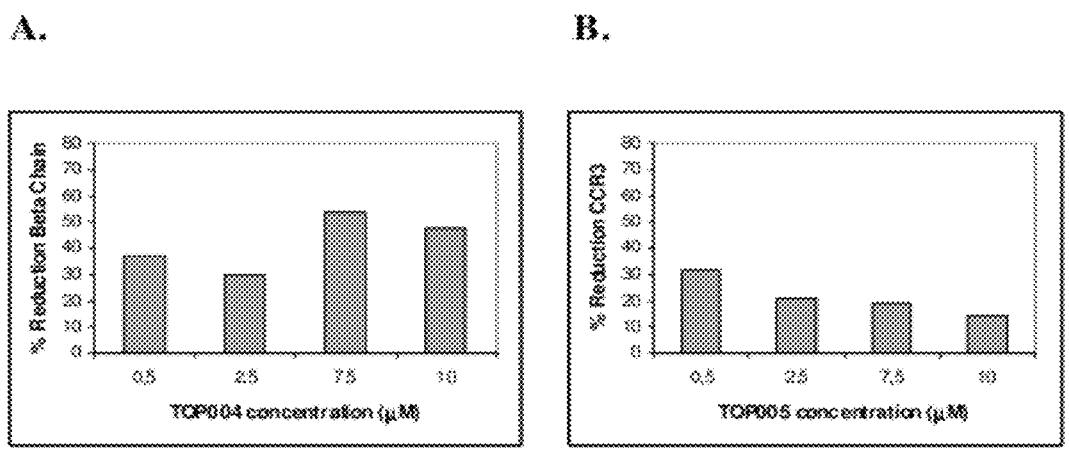
FIG. 3A shows reduced beta-chain ($\beta_c$) cell surface protein expression by different concentrations of TOP004 in cynomolgus monkey PBMCs as compared to untreated cells.
FIG. 3B shows reduced CCR3 cell surface protein expression by different concentrations of TOP005 in cynomolgus monkey PBMCs as compared to untreated cells.
Figure 4:
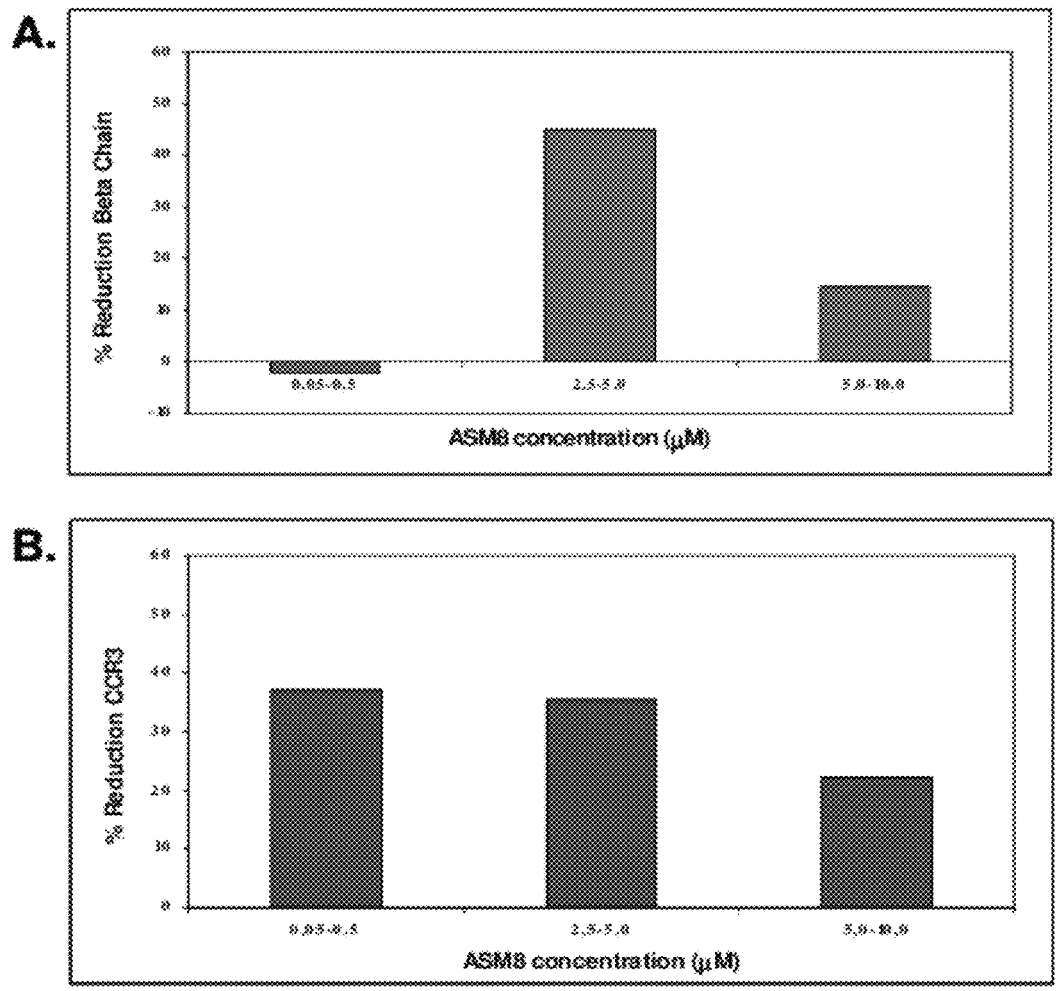
FIG. 4A shows reduced beta-chain ($\beta_c$) mRNA expression by varying concentrations of ASM8 in cynomolgus monkey PBMCs as compared to untreated cells.
FIG. 4B shows reduced CCR3 mRNA expression by varying concentrations of ASM8 in cynomolgus monkey PBMCs as compared to untreated cells.

As disclosed herein, TOP004 and TOP005 possess activity in a non-human primate system, thus validating the use of the cynomolgus monkey for safety assessment. FIG. 1 shows the sequencing of the common beta-chain gene of cynomolgus monkey. The cynomolgus beta-chain sequence complementary to TOP 004 showed significant homology. The very high degree of identity between the monkey and the human beta-chain sequence suggest a probable functional activity of TOP004 in cynomolgus monkey. The effectiveness of TOP 004 and TOP 005 at blocking or decreasing expression of the common beta-chain and CCR3 in monkey peripheral blood mononuclear cells is shown in FIGS. 2, 3, and 4. The results show that both of TOP004 and TOP005 directed against human gene targets are effective at reducing expression of their respective targets in cynomolgus monkey peripheral blood mononuclear cells (PBMC). ASM8, containing both TOP004 and TOP005 significantly inhibited both the common beta-chain expression and CCR3, receptors, either to a greater degree or to the same extent at a lower concentration. TOP004 and TOP005 together therefore exhibit synergistic effects in blocking beta-chain and CCR3 mRNA expression. Furthermore, in Tables 7 and 8, tracheal samples, taken from monkeys treated with ASM8, were analyzed for the level of mRNA expression. The expression of the target genes was normalized to the mRNA levels for inflammatory cytokines (IL-4 and TNF-α). Even approximately 24 hours after administration of ASM8, the relative expression of the β$_c$-subunit and CCR3 mRNA to IL-4 mRNA was decreased by 29% and 24%, respectively, and the expression relative to TNF-α was decreased by 30% and 24%, respectively, in ASM8-treated animals.

In FIGS. 5-10, antisense nucleotides, including A86 and TOP005, directed against the CCR3 mRNA were tested for efficacy in human cells and cell lines. When assessed by semi-quantitative reverse transcription-polymerase chain reaction ("RT-PCR"), the antisense oligonucleotides caused inhibition of CCR3 mRNA expression. Further, using FACS analysis, it is shown that cell surface expression of CCR3 protein was inhibited by antisense oligonucleotide treatment as well. Moreover, the functional inhibition of CCR3 was confirmed by inhibition of calcium (Ca$^{++}$) mobilization in purified eosinophils after stimulation with eotaxin. In addition, the oligonucleotides inhibited eosinophil chemotaxis by 55% in a chemotaxis assay.

In FIGS. 11-13, 107A and TOP004 antisense were used to treat various cells. TF-1 cells incubated with 107A showed reduced beta-chain mRNA expression. 107A also inhibited TF-1 cell proliferation in the presence of IL-3, IL-5, or GM-CSF. Furthermore, 107A reduced, in a dose-dependent manner, the anti-apoptotic effect of IL-5 on eosinophils. U937 cells incubated with TOP004 showed reduced common beta-chain expression at the level of mRNA and protein. The antisenses 107A and TOP004 were thus highly effective in blocking the expression of beta-chain mRNA, protein and functional at blocking the associated cellular responses in human cell cultures.

Figure 14:
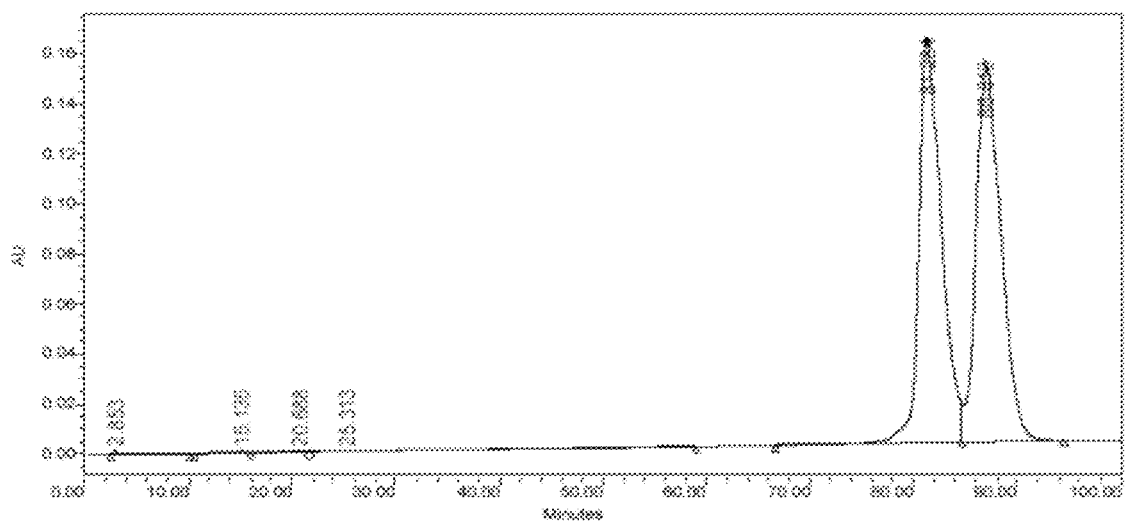
FIG. 14 shows the elution profile of the individual products of ASM8 (TOP004 and TOP005) using DEAE anion exchange chromatography.

In FIGS. 14-17B2, the stability of ASM8 is shown by eluting the composition under varying conditions. ASM8 was eluted using the DEAE anion exchange high performance liquid chromatography (HPLC)-based fractionation system to assess the integrity of ASM8 and its degradation products after storage at different temperatures. ASM8 components did not undergo any detectable degradation when stored at −20° C., 4° C., 30° C., or 40° C. for up to 2 months.

Figure 18:
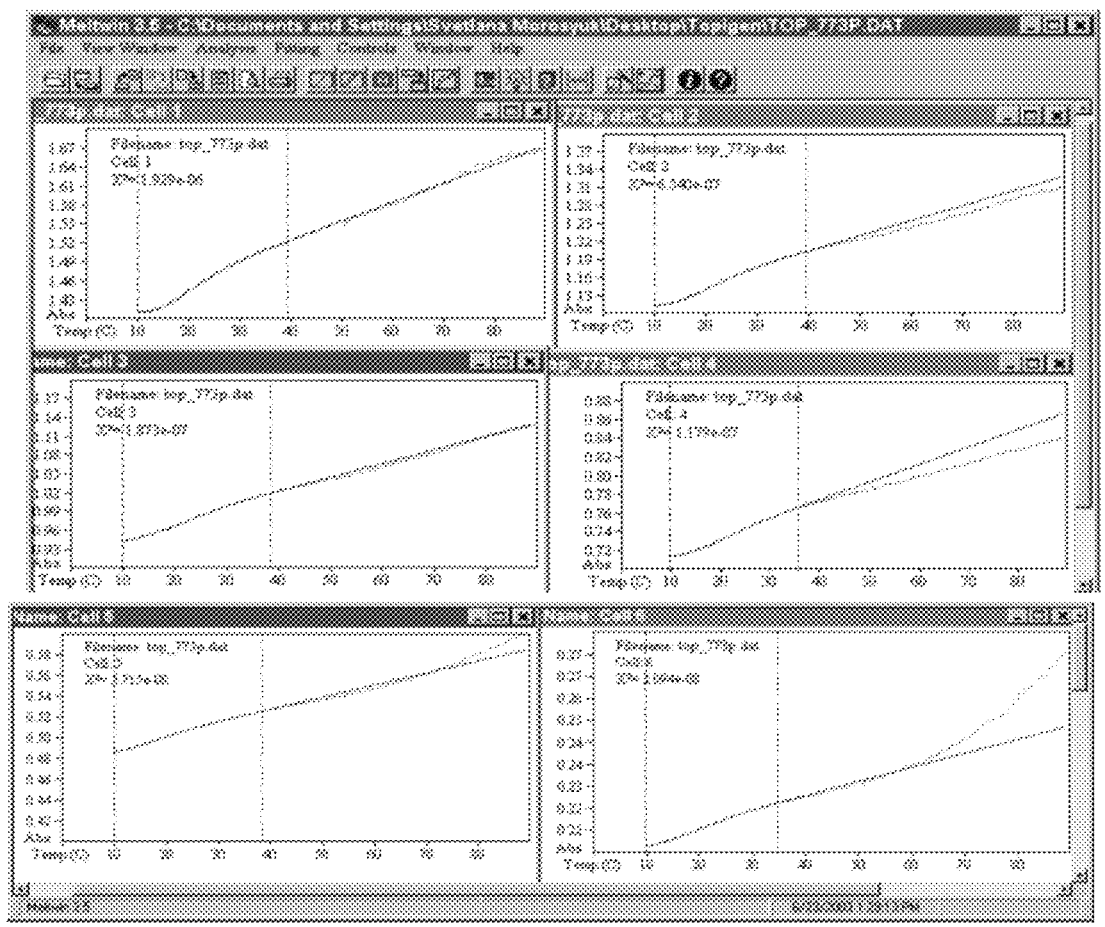
FIG. 18 shows melting curves for TOP004 and TOP005 in 1×PBS.
Figure 19:
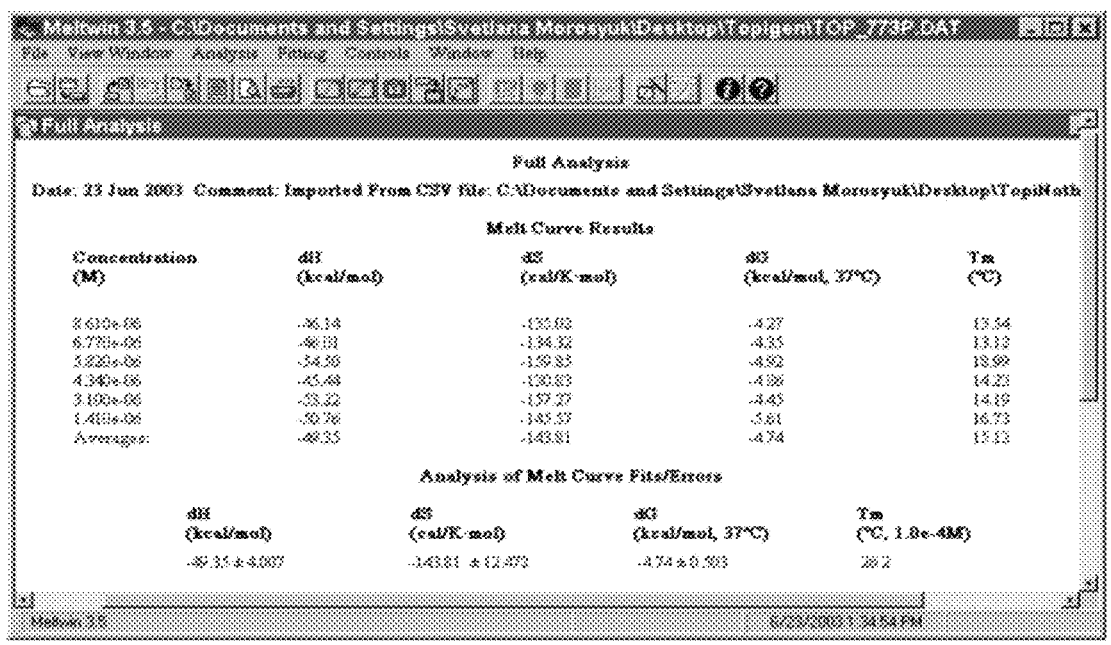
FIG. 19 shows a thermodynamics summary based on results of melting curve fits of TOP004 and TOP005 in 1×PBS.

In FIGS. 18-19, melting curves and thermodynamic summaries provided for ASM8 show that the two oligonucleotide strands do not interact significantly in solution.

Figure 20:
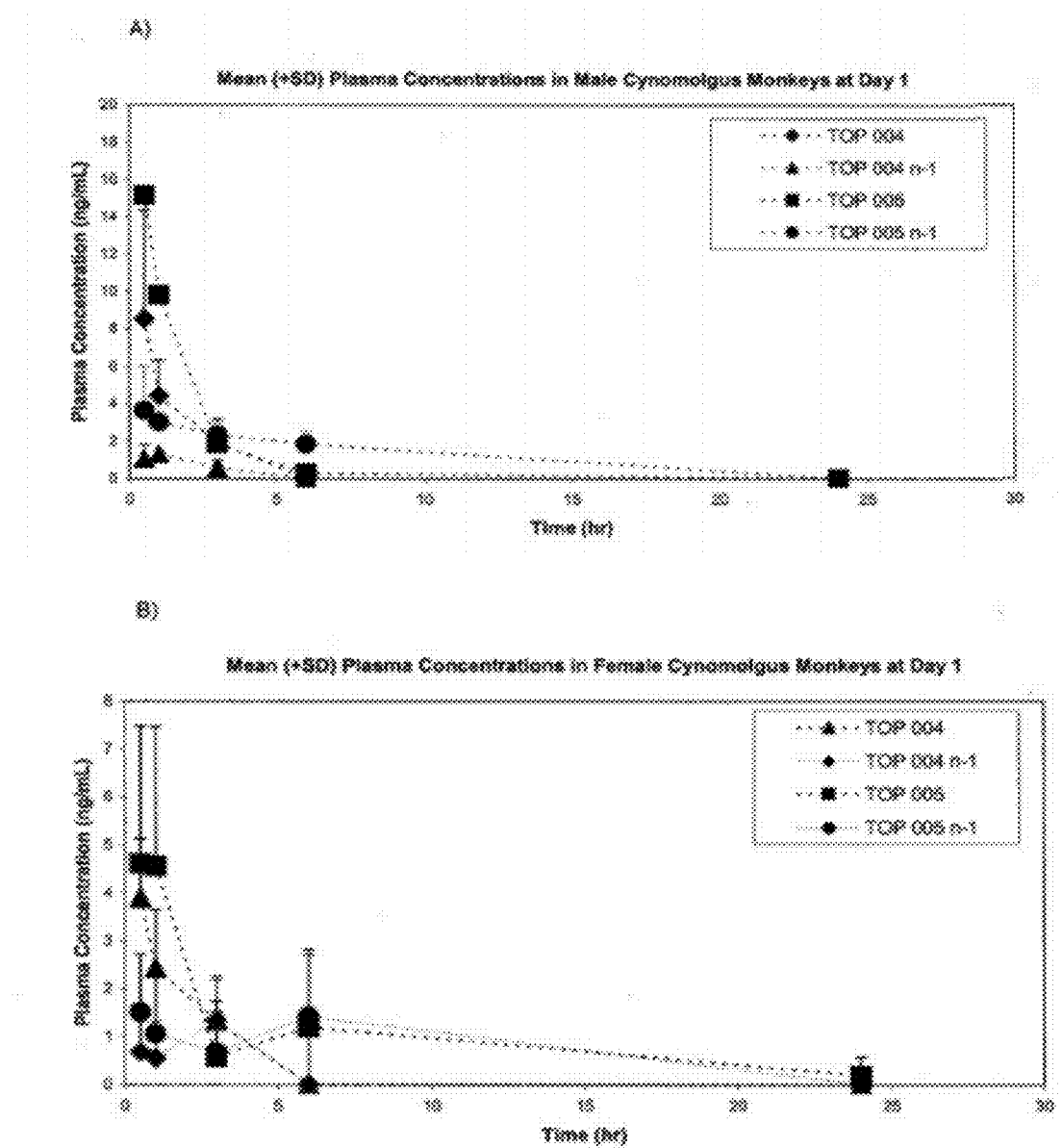
FIGS. 20A and 20B show the concentrations of TOP004 and TOP005 and their metabolites in monkey plasma at day 1 after treatment with a high-dose of ASM8.
Figure 21:
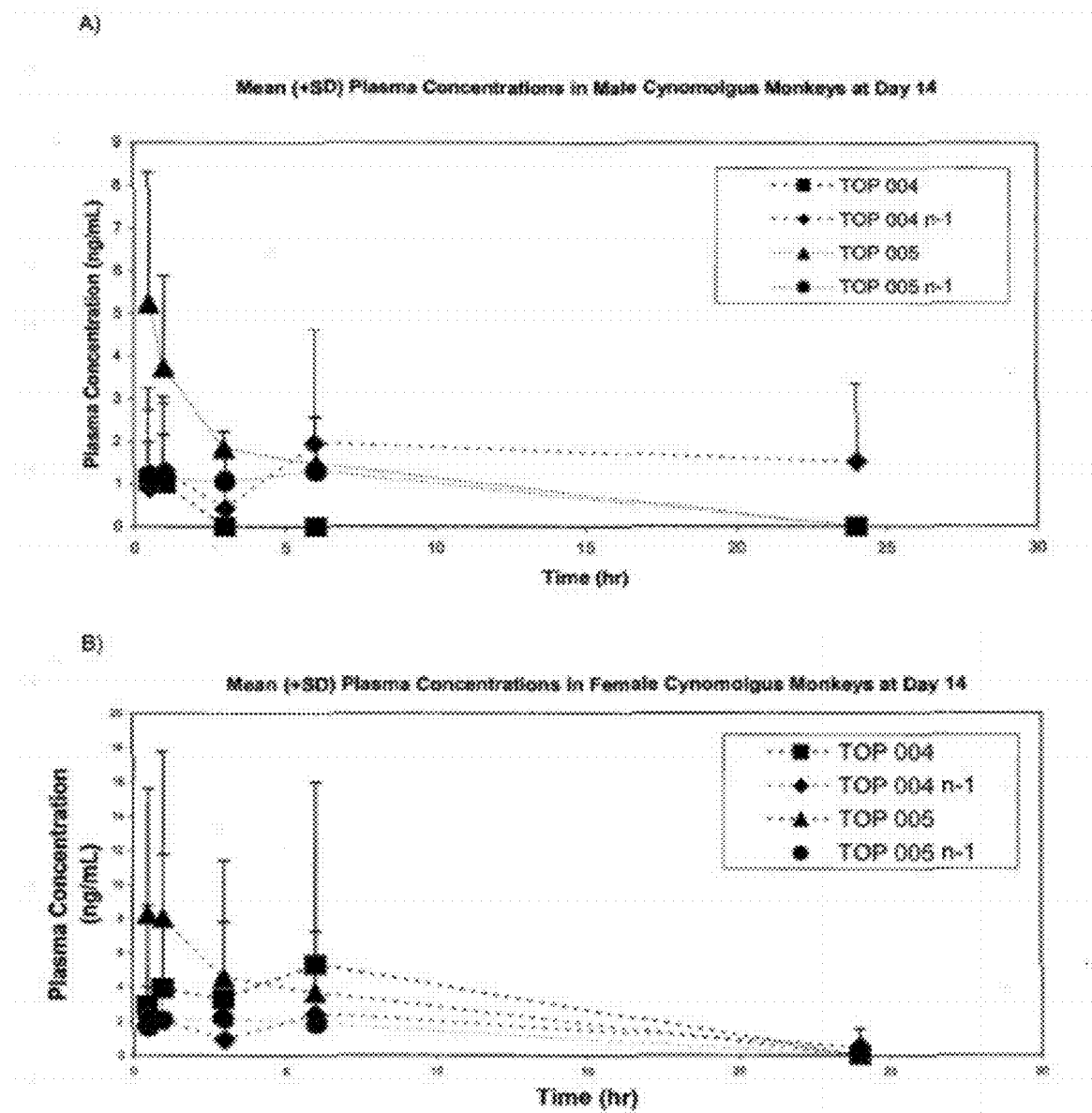
FIGS. 21A and 21B show the concentrations of TOP004 and TOP005 and their metabolites in monkey plasma at day 14 after treatment with a high-dose of ASM8.

In FIGS. 20-21, the concentrations of ASM8 oligonucleotide constituents and their primary metabolites (n−1) in monkey plasma samples were measured. The samples were collected during a nonclinical toxicity trial in which the animals were treated for 14 consecutive days via inhalation.

Antisense oligonucleotides directed against the common beta subunit of IL-3, IL-5 and GM-CSF, and the CCR3, receptors, and against nucleic acids coding therefore, are thus provided. Pharmaceutical compositions comprising the oligonucleotides with a pharmaceutically acceptable carrier are also provided. Uses of the oligonucleotides and methods comprising administering the oligonucleotides for treating and/or preventing at least one of asthma, allergy, hypereosinophilia, general inflammation and cancer are described.

The terms "nucleic acid" and "nucleic acid molecule" as used interchangeably herein, refer to a molecule comprised of nucleotides, i.e., ribonucleotides, deoxyribonucleotides, or both. The term includes monomers and polymers of ribonucleotides and deoxyribonucleotides, with the ribonucleotide and/or deoxyribonucleotides being connected together, in the case of the polymers, via 5' to 3' linkages. However, linkages may include any of the linkages known in the nucleic acid synthesis art including, for example, nucleic acids comprising 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "nucleic acid backbone" as used herein refers to the structure of the chemical moiety linking nucleotides in a molecule. This may include structures formed from any and all means of chemically linking nucleotides. A modified backbone as used herein includes modifications to the chemical linkage between nucleotides, as well as other modifications that may be used to enhance stability and affinity, such as modifications to the sugar structure. For example an [alpha]-anomer of deoxyribose may be used, where the base is inverted with respect to the natural [beta]-anomer. In a preferred embodiment, the 2'-OH of the sugar group may be altered to 2'-O-alkyl or 2'-O-alkyl-n(O-alkyl), which provides resistance to degradation without comprising affinity.

The term "oligonucleotide" as used herein refers to a nucleic acid molecule comprising from about 1 to about 100 nucleotides, more preferably from 1 to 80 nucleotides, and even more preferably from about 4 to about 35 nucleotides.

Antisense oligonucleotide compounds in accordance with the present invention also include siRNAs (small interfering RNAs) and the RISCs (RNA-induced silencing complexes) containing them that result from the RNAi (RNA interference) approach. The RNA interference (RNAi) approach, which has been described recently, is considered as a new tool for the inhibition of target gene expression. As already known some years ago, RNAi is based on an ancient anti-viral defense mechanism in lower eukaryotes. It is induced by double-stranded RNA and its processing to 21-23 nt small interfering RNAs (siRNAs), which cause the degradation of homologous endogenous mRNA after hybridizing to the target mRNA in a single stranded fashion with the assistance of the RISC complex. The way RNAi works is still to be fully elucidated, but it already serves as a first-choice approach to generate loss-of-function phenotypes among a broad variety of eukaryotic species, such as nematodes, flies, plants, fungi and mammals.

Antisense oligonucleotide compounds in accordance with the present invention also include ribozymes and short nucleotide sequences, single or double stranded, RNA or DNA, which may incorporate chemical modifications as described above, capable of inhibiting gene transcription and/or translation in vitro and/or in vivo.

The term "modified oligonucleotide" and "modified nucleic acid molecule" includes antisense oligonucleotide compounds that have been modified without significant adverse effect to their activity, for example, by the insertion or deletion of 1 or more bases. In particular, the addition or deletion of bases at the terminal ends of the oligonucleotides that exhibit 100% complementation to the gene they are directed against can generally be made without significant loss of inhibitory activity. Such modifications may be made in order to increase activity or to provide enhanced stability of the oligonucleotide. In addition, substitution of 1 or more bases in the present antisense oligonucleotide compounds may also be made without adverse effect to activity, for example, substitution of purine with another purine (adenine, guanine) and pyrimidine with pyrimidine (cytosine, thymine, uracil). Modified oligonucleotide and modified nucleic acid molecule as used herein also include nucleic acids, including oligonucleotides, with one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. The internucleoside phosphate linkages can be phosphodiester, phosphotriester, phosphoramidate, siloxane, carbonate, carboxymethylester, acetamidate, carbamate, thioether, bridged phosphoranidate, bridged methylene phosphonate, phosphorothioate, methylphosphonate, phosphorodithioate, bridged phosphorothioate and/or sulfone internucleotide linkages, or 3'-3',2'-5' or 5'-5' linkages, and combinations of such similar linkages (to produce mixed backbone modified oligonucleotides). The modifications can be internal (single or repeated) or at the end(s) of the oligonucleotide molecule and can include additions to the molecule of the internucleoside phosphate linkages, such as cholesteryl, diamine compounds with varying numbers of carbon residues between amino groups and terminal ribose, deoxyribose and phosphate modifications which cleave or cross-link to the opposite chains or to associated enzymes or other proteins. Electrophilic groups such as ribose-dialdehyde may be covalently linked with an epsilon amino group of the lysyl-residue of such a protein. A nucleophilic group such as n-ethylmaleimide tethered to an oligomer could covalently attach to the 5' end of an mRNA or to another electrophilic site. The term modified oligonucleotides also includes oligonucleotides comprising modifications to the sugar moieties such as 2'-substituted ribonucleotides, or deoxyribonucleotide monomers, any of which are connected together via 5' to 3' linkages. Modified oligonucleotides may also be comprised of PNA or morpholino modified backbones where target specificity of the sequence is maintained. The term modified oligonucleotides also includes oligonucleotide compounds, as defined herein, of a form that does not significantly adversely affect their activity to reduce activity or inhibit expression of a target protein, but which may enhance this activity.

Modified oligonucleotides also include oligonucleotides that are based on or constructed from arabinonucleotide or modified arabinonucleotide residues, including but not limited to antisense oligonucleotide constructs based on beta-arabinofuranose and its analogues. Aribonucleosides are stereoisomers of ribonucleosides, differing only in the configuration at the 2'-position of the sugar ring. PCT Application No. WO 99/67378 by Damha et al. (1), which is hereby incorporated by reference in its entirety, discloses arabinonucleic acids (ANA) oligomers and their analogues for improved sequence specific inhibition of gene expression via association to complementary messenger RNA. Dahma et al. further teaches sugar-modified oligonucleotides that form a duplex with its target RNA sequence resulting in a substrate for RNaseH. Specifically, oligomers comprising beta-D-arabinonucleotides and 2'-deoxy-2'-fluoro-beta-D-arabino-nucleosides are disclosed. PCT Application No. WO 02/20773 also by Dahma et al. (2), which is hereby incorporated by reference in its entirety, discloses oligonucleotide chimeras used to inhibit gene transcription and expression in a sequence specific manner. Specifically, Dahma et al. (2) teaches antisense oligonucleotides constructed from arabinonucleotides flanking a series of deoxyribose nucleotide residues of variable length. Antisense oligonucleotides so constructed are used to hybridize and induce cleavage of complementary RNA. PCT Application No. WO 03/037909 also by Dahma et al. (3), which is hereby incorporated by reference in its entirety, discloses oligonucleotides having an internal acyclic linker residue. Antisense oligonucleotides prepared with an acyclic linker are used to prevent or deplete function of a target nucleic acid of interest such RNA. PCT Application No. WO 03/064441 also by Dahma et al. (4), which is hereby incorporated by reference in its entirety, discloses oligonucleotides having alternating segments of sugar-modified nucleosides and 2' deoxynucleosides and also alternating segments of sugar-modified nucleotides and 2' deoxynucleotides. Antisense oligonucleotides having these alternating segments are disclosed to be used to prevent or deplete function of a target nucleic acid of interest such as RNA.

The term "substantially nuclease resistant" refers to nucleic acids that are resistant to nuclease degradation, as compared to naturally occurring or unmodified nucleic acids. Modified nucleic acids of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant nucleic acids include, but are not limited to, nucleic acids with modified backbones such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n(O-alkyl), 3'-O-alkyls, 3'-O-alkyl-n(O-alkyl), 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The terms "CCR3 and common beta-chain for IL-3/IL-5/GM-CSF, -receptors, antisense oligonucleotides" as used herein each refer to an oligonucleotide that is targeted, respectively, to sequences that affect CCR3 chemokine receptor and the common beta-chain for IL-3/IL-5/GM-CSF, -receptors, expression and/or activity. These include, but are not limited to, CCR3 chemokine receptor and the common beta-chain for IL-3/IL-5/GM-CSF, -receptors, DNA coding sequences, DNA promoter sequences, DNA enhancer sequences, mRNA encoding sequences, and the like.

As discussed above, one embodiment of the present invention provides antisense oligonucleotides targeted to sequences that affect CCR3 chemokine receptor and the common beta-chain for IL-3/IL-5/GM-CSF, -receptors, expression and/or activity. In one embodiment the antisense oligonucleotide may comprise fragments or variants of these sequences, as will be understood by a person skilled in the art, that may alter the oligonucleotide make-up and/or length, but which maintains or increases the activity of the oligonucleotide to down-regulate gene expression. In another embodiment the present invention provides for combinations of at least two antisense oligonucleotides from the sequences identified as SEQ ID NO. 1, SEQ ID NO. 13 and SEQ ID NO. 14.

The terms "treatment", "treating", "therapy" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or amelioration of an adverse effect attributable to the disease. "Treatment" as used herein covers any treatment of a disease in a subject as previously defined, particularly a human, and includes:

(a) preventing a disease from occurring in a subject which may be predisposed to the disease but has not yet been diagnosed as having it;
(b) inhibiting a disease, i.e., arresting its development; or
(c) relieving a disease, i.e., causing regression of the disease.

The term "pharmaceutically acceptable" as it is used herein with respect to carriers, surfactants and compositions refers to substances which are acceptable for use in the treatment of a subject patient that are not toxic or otherwise unacceptable for administration by any of the routes herein described.

The invention is generally directed toward the treatment of subjects by the administration of therapeutically effective amounts of antisense oligonucleotide compounds in accordance with the present invention, including siRNA, ribozymes, short nucleotide sequences as single or double stranded including RNA and/or DNA that may be complementary to a target nucleic acid, or may optionally be modified as described above, an RNA oligonucleotide having at least a portion of said RNA oligonucleotide capable of hybridizing with RNA to form an oligonucleotide-RNA duplex, or a chimeric oligonucleotide, that will downregulate or inhibit the expression of an endogenous gene in vivo.

By "therapeutically effective" amount is meant a nontoxic but sufficient amount of an antisense oligonucleotide compound to provide the desired therapeutic effect. In the present case, that dose of antisense oligonucleotide compound effective to relieve, ameliorate, or prevent symptoms of the condition or disease being treated, e.g. disease associated with allergy, asthma, inflammatory disease such as inflammatory respiratory disease.

The term "allergy" as used herein, describes any undesirable immune response by the body to a substance to which it has become hypersensitive.

The formulations of the present invention are preferably administered directly to the site of action and thus preferably are topical, including but not limited to, oral, intrabuccal, intrapulmonary, rectal, intrauterine, intratumor, nasal, intrathecal, inhalable, transdermal, intradermal, intracavitary, iontophoretic, ocular, vaginal, intraarticular, otical, transmucosal, rectal, slow release or enteric coating formulations. Without limiting any of the foregoing, formulations of the present invention may also be intracranial, intramuscular, subcutaneous, intravascular, intraglandular, intraorgan, intralymphatic, intraperitoneal, intravenous, and implantable. The carriers used in the formulations may be, for example, solid and/or liquid carriers.

Reference may be made to "Remington's Pharmaceutical Sciences", 17th Ed., Mack Publishing Company, Easton, Pa., 1985, for other carriers that would be suitable for combination with the present oligonucleotide compounds to render compositions/formulations suitable for administration to treat respiratory disease.

Optionally, the presently described oligonucleotides may be formulated with a variety of physiological carrier molecules. The presently described oligonucleotides may also be complexed with molecules that enhance their ability to enter the target cells. Examples of such molecules include, but are not limited to, carbohydrates, polyamines, amino acids, peptides, lipids, and molecules vital to cell growth. For example, the oligonucleotides may be combined with a lipid, the resulting oligonucleotide/lipid emulsion, or liposomal suspension may, inter alia, effectively increase the in vivo half-life of the oligonucleotide.

The pharmaceutical compositions provided herein may comprise antisense oligonucleotide compounds described above and one or more pharmaceutically acceptable surfactants. Suitable surfactants or surfactant components for enhancing the uptake of the antisense oligonucleotides of the invention have been previously described in U.S. Application Publication No. 2003/0087845, the contents of which are incorporated herein with respect to surfactants The application states that suitable surfactants " . . . include synthetic and natural as well as full and truncated forms of surfactant protein A, surfactant protein B, surfactant protein C, surfactant protein D and surfactant protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamelar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly(vinyl amine) with dextran and/or alkanoyl side chains, Brij 35™, Triton 100™ and synthetic surfactants ALEC™, Exosurf™, Survan™ and Atovaquone™, among others. These surfactants may be used either as single or part of a multiple component surfactant in a formulation, or as covalently bound additions to the 5' and/or 3' ends of the antisense oligonucleotides."

The antisense component of the present compositions may be contained in a pharmaceutical formulation within a lipid particle or vesicle, such as a liposome or microcrystal. As described in U.S. Pat. No. 6,025,339, the lipid particles may be of any suitable structure, such as unilamellar or plurilamellar, so long as the antisense oligonucleotide is contained therein. Positively charged lipids such as N-[1-(2,3-dioleoyloxi) propyl]-N,N,N-trimethyl-ammoniumethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The composition of the invention may be administered by any means that transports the antisense oligonucleotide compound to the desired site, such as for example, the lung. The antisense compounds disclosed herein may be administered to the lungs of a patient by any suitable means, but are preferably administered by inhalation of an aerosol comprised of respirable particles that comprise the antisense compound.

The composition of the present invention may be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. Particles of non-respirable size that are included in the aerosol tend to deposit in the throat and be swallowed, and the quantity of non-respirable particles in the aerosol is preferably thus minimized. For nasal administration, a particle size in the range of 10-500 micro-M (micrometer)) is preferred to ensure retention in the nasal cavity.

Liquid pharmaceutical compositions of active compound (the antisense oligonucleotide compound(s)) for producing an aerosol may be prepared by combining the antisense compound with a suitable vehicle, such as sterile pyrogen free water or phosphate buffered saline.

A solid particulate composition comprising the antisense compound may optionally contain a dispersant that serves to facilitate the formation of an aerosol as well as other therapeutic compounds. A suitable dispersant is lactose, which may be blended with the antisense compound in any suitable ratio, e.g., a 1 to 1 ratio by weight.

The antisense compositions may be administered in an anti-bronchoconstriction, anti-allergy(ies) and/or anti-inflammatory effective amount, which amount depends upon the degree of disease being treated, the condition of the subject patient, the particular formulation, the route of administration, the timing of administration to a subject, etc. In general, intracellular concentrations of the oligonucleotide of from 0.05 to 50 microM, or more particularly 0.2 to 5 microM, are desirable. For administration to a mammalian patient such as a human, a dosage of about 0.001, 0.01, 0.1, or 1 mg/Kg up to about 50, or 100 mg/Kg or more is typically employed. However, other doses are also contemplated. Depending on the solubility of the active compound in any particular formulation, the daily dose may be divided among one or several unit dose administrations.

The aerosols of liquid particles comprising the antisense compound may be produced by any suitable means, such as with a nebulizer. Nebulizers are commercially available devices that transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active antisense oligonucleotide ingredient in a liquid carrier in an amount of up to 40% w/w preferably less than 20% w/w of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, anti-oxidants, anti-bacterials, flavorings, volatile oils, buffering agents and emulsifiers and other formulation surfactants.

The aerosols of solid particles comprising the active oligonucleotide compound(s) and a pharmaceutically acceptable surfactant may likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. The active oligonucleotide ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 microL, to produce a fine particle spray containing the active ingredient. Suitable propellants include certain chlorofluorocarbon compounds, for example, dichlorodifluoromethane, trichlorofluoromethane, dichlorotetrafluoroethane or hydrofluoroalkanes and mixtures thereof. The formulation may additionally contain one or more co-solvents, for example, ethanol, emulsifiers and other formulation surfactants, such as oleic acid or sorbitan trioleate, anti-oxidants and suitable flavoring agents.

The aerosol, whether formed from solid or liquid particles, may be produced by the aerosol generator at a rate of from about 1 to 150 liters per minute.

In a further aspect of the present invention, an article of manufacture is provided which includes packaging material contained within which is a pharmaceutically acceptable antisense oligonucleotide composition that is therapeutically effective to treat conditions associated with allergy, asthma, rhinitis and inflammatory disease. In one embodiment, the composition comprises an antisense oligonucleotide compound that is effective to inhibit a CCR3 chemokine receptor or the common beta-chain for IL-3/IL-5/GM-CSF, -receptors, gene, said oligonucleotide compound being at least 50% complementary to the gene. In another aspect, the composition comprises at least 2 antisense oligonucleotide compounds, each antisense oligonucleotide compound being capable of downregulating the CCR3 chemokine receptor and the common beta-chain for IL-3/IL-5/GM-CSF, -receptors, gene, each antisense oligonucleotide compound being present at a concentration at which the antisense oligonucleotide compound is practically ineffective on its own to downregulate the gene it is directed against, the combination of the antisense oligonucleotide compounds being effective to downregulate at least one of the genes that the antisense oligonucleotides are directed against.

In one embodiment, the packaging material of the article comprises a label which indicates that the composition can be used to treat inflammatory respiratory disease and may additionally include an indication that the disease is one of allergy, rhinitis and asthma.

In another embodiment, the packaging material of the article comprises a label which indicates that the composition can be used to treat inflammatory respiratory disease, and may additionally include an indication that the disease is one of allergy, asthma, hypereosinophilia, bronchitis, rhinitis or sinusitis.

For the purposes of the present invention, the packaging material may be any suitable material for packaging a nucleotide-containing composition in accordance with the present invention, including a bottle or other container (either plastic or glass), a carton, a tube, or other protective wrapping. As will be appreciated, the packaging may vary with the nature of the oligonucleotide composition, for example, a liquid formulation may be packaged differently than an aerosol formulation.

The present invention will be more readily understood by referring to the examples that are given to illustrate the following invention rather than to limit its scope. With respect to these examples, the following were methods and materials were used.

EXAMPLES

Materials and Methods

Materials

The following materials and reagents were used for the experiments: RPMI 1640 (Wisent, cat#10040 CV); FBS (Fetal Bovine Serum, Wisent, cat#80150); Penicillin-Streptomycin (GIBCO, cat#15140-122); HEPES (Wisent, cat#26060CI); L-glutamine (Gibco, cat#25030-081); Sodium Pyruvate (Wisent, cat#25000-Ci); PBS Sterile (GIBCO, cat#25030-081); Hanks Balanced Salt Solution (HBSS, cellgro, cat#20021-cv); Superscript First-Strand Synthesis System for RT-PCR kit (Invitrogen, cat#11904-018); dNTPs (Invitrogen, cat#10297-018; oligo $(dT)_{12-18}$ (Invitrogen, cat#11904-018); Qiagen RNAeasy Mini Kit (Qiagen, cat#74106); Qiagen gel extraction kit (Qiagen, cat#28704); Qiagen PCR extraction kit (Qiagen, cat#28104); β-Mercaptoethanol (Sigma, cat#M-6250); 99% Ethanol (Commercial alcohols Inc., Brampton, Ontario, Canada); QiaVac 24 Manifold (Qiagen, cat#19403); Disposable Vacconnectors (Qiagen, cat#19407); DNase I kit (Fermentas, cat.#EN0521); RiboGreen Quantification Reagent (Invitrogen-Molecular probes, cat#R-11490); Taq PCR core kit (Qiagen, cat#201223), Hema-3 stain set (Fisher scientific Co. cat#122-911, lot#999901); Alamar Blue (Biosource cat#DAL1100); Human CCR3 primer pair (R&D systems, cat# RDP-209-025); Human GAPDH primer pair (R&D systems, cat# RDP-39-025); Ficoll (Amersham Biosciences; cat#: 17-1440-03); anti-CD16 (Eosinophils purification kit, Miltenyi Biotec, Auburn, Calif., cat#130-045-701); rhEotaxin (Biosource, cat# PMC1434); Chemotaxis chamber and membranes (NeuroProbe, Nucleopore-Neuroprobe, Cabin John, Md.); Human serum albumin (SIGMA; cat.#A9511); Anti human IL-3/IL-5/GM-CSF Receptors beta-chain (mouse monoclonal IgG2b; Santa Cruz Biotechnology, cat.#sc-457); Anti-mouse IgG2b (goat monoclonal, Alexa Fluor 488, Molecular Probes, cat#A-21141); Anti-human CCR3 antibody (rat monoclonal, IgG2a, R&D, cat.# MAB155); Anti-rat IgG (goat monoclonal, Alexa Fluor 633, Molecular Probes, cat.# A-21094); rhGM-CSF (R & D systems, cat#215-GM-005); rhIL-3 (R & D systems, cat#203-IL-010); rhIL-5 (R & D systems, cat#205-IL-005), rhIL-2 (R&D systems, cat#202-IL-010); TOP 004-(n−1) (Biosource, Oligonucleotide with one nucleotide less on 3' end); TOP 005-(n−1) (Biosource, Oligonucleotide with one nucleotide less on 3' end); TOP 004-TP (Biosource, Template Probe); TOP 004-(n−1-TP-T) (Biosource Biosource, template Probe); LP (Biosource, Ligation Probe); TOP 005-TP (Biosource); TOP 004-(n−1-LP-A, Biosource); Reacti-Bind neutravidin-coated high binding capacity plates (Pierce, cat #15508); T4 DNA Ligase 5 U/mL (Roche, cat #799 009); Anti-DIG-AP antibody (Roche, cat#1093274); SuperBlock Blocking Buffer in PBS (Pierce, cat #37515); Methylumbelliferyl phosphate alkaline phosphatase substrate (Molecular Probes, cat #M-6491); Monkeys plasma samples containing ASM8; MW96 Plate Washer (Beckman Coulter); 96-well large capacity polypropylene plate, Nunc); Micropipettors from Eppendorf Research Brand; Black opaque 96-well plates (Costar, cat#3915).

Antisense Synthesis and Sequence Identification

Oligonucleotides were synthesized with a Gene Assembler-Plus™ (Pharmacia Biotech, Piscataway, N.J., USA), phosphorothioated and purified by HPLC. The TOP005 used in experiments illustrated in FIGS. 5-7 were performed with cGMP oligonucleotides. Antisense sequences and identifications are described in Table 1.

TABLE 1

| Antisense # | Antisense Sequence 5'-3' | Gene bank accession # and/or SEQ ID NO |
|---|---|---|
| 828 | 5-GTTACTACTTCCACCTGCCTG-3 (SEQ ID NO: 1) | AF224496- SEQ ID NO. 50 |
| 773 | 5-TGGAAAAGCGACACCTACCTG-3 (SEQ ID NO: 2) | AF247360- SEQ ID NO. 51 |
| 786 | 5-CCCTTTTCCTGGAAAAGCGACA-3 (SEQ ID NO: 3) | AF247360- SEQ ID NO. 51 |
| 788 | 5-CTCCCTTTTCCTGGAAAAGCG-3 (SEQ ID NO: 4) | AF247360- SEQ ID NO. 51 |
| 793 | 5-TCCACCTCCCTTTTCCTGGA-3 (SEQ ID NO: 5) | AF247361- SEQ ID NO. 52 |
| 807 | 5-CCTCCTTGTTCCACCTCCCTT-3 (SEQ ID NO: 6) | AF247362- SEQ ID NO. 53 |
| RZ1 | 5-ACCCATTGGCATTGCTCATTT-3 (SEQ ID NO: 7) | AF247360- SEQ ID NO. 51 |
| RZ2 | 5-TCCTTGCAATTAGTGCTGCTT-3 (SEQ ID NO: 8) | AF247361- SEQ ID NO. 52 |
| RZ3 | 5-TCGTGCAGTTCTTCTTTTTCA-3 (SEQ ID NO: 9) | AF247362- SEQ ID NO. 53 |
| RZ4 | 5-CAGACTAGCTTCTCAGTTTTG-3 (SEQ ID NO: 10) | AF247363- SEQ ID NO. 54 |
| RZ5 | 5-TGCTAATTTAGTGAAGTCCTT-3 (SEQ ID NO: 11) | AF247364- SEQ ID NO. 55 |
| RZ6 | 5-CTTCTCCCTGAAAATCTCTTCT-3 (SEQ ID NO: 12) | AF224495- SEQ ID NO. 56 |
| 107A | 5-GGGTCTGCAGCGGGATGGT-3 (SEQ ID NO: 43) | NM_000398-1- SEQ ID NO. 43 |
| A86 | 5-CTGGGCCATCAGTGCTCTG-3 (SEQ ID NO: 29) | NM_178329-1- SEQ ID NO. 58 |
| *TOP004 | 5-GGGTCTGCXGCGGGXTGGT-3 (SEQ ID NO: 13) | NM_000395-1- SEQ ID NO. 59 |
| *TOP005 | 5-GTTXCTXCTTCCXCCTGCCTG-3 (SEQ ID NO: 14) | AF224496 SEQ ID NO. 60 |

*X =, X represents a DAP modification of an adenosine residue.

Cells and Cell Culture

The following cell lines were used: TF-1 (Human erythroleukemia cell line, ATCC#CRL-2003); EOL-1 (Human acute myeloid "Eosinophilic" leukemia cell line; DSMZ#ACC386) and U937 (Human histicytic lymphoma cell line; ATCC#CRL-1593.2). EOL-1 and U937, were cultured in RPMI 1640 with 2 mM L-glutamine; 1.5 g/L sodium bicarbonate; 4.5 g/L glucose; 10 mM Hepes; 1 mM sodium pyruvate; 10% FBS, Penicillin 100 U/mL, Streptomycin 100 microg/mL. The same medium is used for TF-1 culture, except that rhGM-CSF is added at 2 ng/mL.

HL-60 Clone 15 Cell Culture and Differentiation

HL-60 clone 15 was differentiated to Eosinophils as described by Tiffany et al., 1998, J. Immunol. 160:1385-1392. Briefly, The promyelocytic cell line HL-60 was maintained in RPMI 1640 with L-glutamine supplemented with 10% heat-inactivated FBS and 25 mM N-[2-hydroxyethyl] piperazine-N'-[2-hydroxypropanesulfonic acid] (Sigma Chemical Co., St. Louis, Mo.), pH 7.6, at 37° C. and 5% $CO_2$. Cells were induced to differentiate to eosinophil-like phenotype by treating them with 0.5 microM butyric acid (Sigma Chemical Co., St. Louis, Mo.) for at least 5 days. FACS analysis was used to assess the presence of the common beta-chain for IL-3/IL-5/GM-CSF receptors, after cells differentiation.

Cell Viability and Antisense Treatment

Cell viability was systematically assayed using Alamar Blue test following the manufacturer procedure. EOL-1; TF-1; HL-60 or U937 cells were harvested by centrifugation (5 minutes, 1500 RPM, at room temperature), washed with 3×HBSS and re-suspended at $1 \times 10^6$ cells/mL in RPMI medium without serum. $1 \times 10^6$ cells were incubated, in triplicates, for 5 minutes with an exact antisense concentration (between 0 and 20 microM) in a sterile microtube. Each reaction was then transferred in 12 well plates and incubated at 37° C., 5% $CO_2$ for 5 hours for mRNA quantification or 12 hours for protein analysis. RPMI/FBS 20% was added to a final concentration of 10% FBS and cells were incubated at 37° C., 5% $CO_2$ overnight. Cells were harvested by centrifugation (5 minutes, 1500 RPM, at room temperature) and washed with 1×HBSS. Control experiments were included and consisted of cell treatments in absence of antisense or in presence of mismatch oligonucleotides.

Purification of Human Eosinophils

The granulocyte fraction was obtained by centrifugation of whole blood through Ficoll-Hypaque gradients (1.077 g/mL at 350 g for 30 minutes) to obtain the buffy coat layer. Human eosinophils were further purified by negative selection with anti-CD16 coated immunomagnetic microbeads at 4° C. using the magnetic cell sorting system of Miltenyi Biotec (Auburn, Calif.). The purity of eosinophil populations, estimated by Giemsa staining, was typically 92%-100%.

Purification of Human and Cynomolgus Monkey PBMC

Fresh blood from cynomolgus monkeys was obtained from ITR Laboratories Canada Inc. PBMC were isolated by Ficoll-Hypaque density gradient centrifugation of EDTA K3 blood from normal donors. PBMC were plated at $2 \times 10^6$ cells/mL/well in 12 well plates in RPMI 1640 cell culture medium supplemented with 10% heat inactivated FBS, Penicillin 100 U/mL, Streptomycin 100 microg/mL. Cell viability was assessed using Alamar Blue and was typically 85%-95%.

Human PBMC and Eosinophils Transfection

Human PBMC were harvested by centrifugation (5 minutes, 1500 RPM, at room temperature), washed with 3×HBSS and re-suspended at $2 \times 10^6$ cells/mL in RPMI medium 5% serum containing 10 microg/mL PHA. $2 \times 10^6$ cells were incubated, in triplicates, for 5 minutes with an exact antisense concentration (between 0 and 20 microM) in a sterile microtube. Each reaction was then transferred in 12 well plates and incubated at 37° C., 5% $CO_2$ overnight for mRNA quantification or 48 hours, or less when stated, for protein analysis. Cells were harvested by centrifugation (5 minutes, 1500 RPM, at room temperature) and washed with 1×HBSS. Control experiments were included and consisted of cell treatments in absence of antisense or in presence of mismatch oligonucleotides.

Purified Human Eosinophils were harvested by centrifugation (5 minutes, 1500 RPM, at room temperature), washed with 3×HBSS and re-suspended at 2.5×10⁶ cells/mL in RPMI medium 10% serum containing 2 nanog/mL rhGM-CSF or rhIL-5, overnight. The day after, cells were washed twice with HBSS and re-suspended at 2.5×10⁶ cells/mL in RPMI medium 5% serum and were incubated, in triplicates, for 5 minutes with an exact antisense concentration (between 0 and 20 microM) in a sterile microtube. Each reaction was then transferred in 12 well plates and incubated at 37° C., 5% $CO_2$ overnight for mRNA quantification or 48 hours, or less when stated, for protein analysis. Cells were harvested by centrifugation (5 minutes, 1500 RPM, at room temperature) and washed with 1×HBSS. Control experiments were included and consisted of cell treatments in absence of antisense or in presence of mismatch oligonucleotides.

Monkey PBMC Transfection

Cynomolgus Monkey PBMC were harvested by centrifugation (5 minutes, 1500 RPM, at room temperature), washed with 3×HBSS and re-suspended at 2×10⁶ cells/mL in RPMI medium 5% serum and 10 microg/mL PHA (or 10 nanog/mL rhIL-2, when stated). 2×10⁶ cells were incubated, in triplicates, for 5 minutes with an exact antisense concentration (between 0 and 20 microM) in a sterile microtube. Each reaction was then transferred in 12 well plates and incubated at 37° C., 5% $CO_2$ overnight for mRNA quantification or 48 hours, or less when stated, for protein analysis. Cells were harvested by centrifugation (5 minutes, 1500 RPM, at room temperature) and washed with 1×HBSS. Control experiments were included and consisted of cell treatments in absence of antisense or in presence of mismatch oligonucleotides.

Flow Cytometric Analysis

Cells were Counted and re-suspended at 1×10⁶ cells per mL. The cells were Centrifuged at 400×g for 3 min. at 20-25° C., and the supernatants discarded. Thereafter, the cell pellet was re-suspended in 50 microL of FACS buffer (1×PBS, pH 7.2-7.4; 0.5% human albumin; 2.5% human serum) and incubated at 37° C. for 30 min. Without discarding the supernatant add primary antibody directly to the tube and mix. Incubate at 4° C. protected from light for 1 h, (Anti human CCR-3 antibody was used at 1 microg per 0.5×10⁶ cells. Anti human common beta-chain was used at 2 microg per 0.5×10⁶ cells). Wash with 2 mL of FACS buffer, centrifuge at 400×g for 3 min. and discard the supernatant. For isotype controls, resuspend cell pellet with 300 microL of FACSFix (1×PBS, pH 7.2-7.4; 4% paraformaldehyde), keep at 4° C. protected from light.

For CCR3 and common beta-chain labeling, resuspend cell pellet with 50 microL of FACS buffer and add the secondary antibody, (Anti rat IgG2a Alexa Fluor 633 was used at 1 microg per 0.5×10⁶ cells. Anti mouse IgG2b Alexa Fluor 488 was used at 2 microg per 0.5×10⁶ cells). Incubate at 4° C. protected from light for 1 h. Wash with 2 mL of FACS buffer, centrifuge at 400×g for 3 min. and discard the supernatant. Fix labeled cells with 300 microL of FACSFix, keep at 4° C. protected from light. Data were analyzed in a BD biosciences FACS calibur and processed with the Cell Quest program.

Calcium Mobilization Assay

Eosinophils were resuspended at 1×10⁷ cells/mL in RPMI 1640 containing 10% FBS and loaded by incubating with 5 M Fura-2 AM (Molecular Probes, Eugene, Oreg., USA) at room temperature for 30 min in the dark. The cells (1×10⁶ cells/mL) were washed three times and resuspended in saline buffer (138 mM NaCl, 6 mM KCl, 1 mM $CaCl_2$, 10 mM Hepes, 5 mM glucose, and 1% BSA, pH 7.4). Each 2 mL of the cell suspension was then transferred to a quartz cuvette, which was placed in a luminescence spectrophotometer LS50B (Perkin-Elmer, Beaconsfield, UK). $Ca^{2+}$ mobilization of the cells was measured by recording the ratio of fluorescence emitted at 510 nm after sequential excitation at 340 and 380 nm in response to chemokine.

Chemotaxis Assay

In vitro chemotaxis was assessed in 48-well chambers (NeuroProbe, Cabin John, Md.) using polyvinylpyrrolidone-free polycarbonate membranes with 5 mm pores (Nucleopore-Neuroprobe). Control or antisense treated eosinophils were suspended in 1×10⁶ cells/mL in RPMI 1640 medium containing 0.25% BSA. The upper and lower wells contained 50 microL and 31 microL of cell suspension, respectively, with the latter suspension supplemented with an optimal concentration of eotaxin (80 nanog/mL). After 1 hour of incubation at 37° C. in 5% $CO_2$, migrated cells present in the lower well were counted. Spontaneous migration was determined in the absence of eotaxin and factored into results.

Monkey Antisense Treatment and Toxicity Studies

This protocol was reviewed and assessed by the Animal Care Committee (ACC) of ITR Laboratories Canada Inc. All animals were cared for in accordance with the principles outlined in the current "Guide to the Care and Use of Experimental Animals" as published by the Canadian Council on Animal Care and the "Guide for the Care and Use of Laboratory Animals", an NIH publication.

The toxicity of ASM8, consisting of a 1:1 mixture of two oligonucleotides (TOP 004 and TOP 005) was investigated to characterize the toxicokinetic profile of its individual oligonucleotide components, when administered by inhalation exposure once daily for 14 consecutive days. The reversibility of any effects of ASM8 following a 14-day recovery period was also assessed. Any systemic hypersensitivity condition following 14 days of inhalation exposure to ASM8 (detectable by intra-dermal injection (ID)) was also assessed.

The vehicle control article was 0.9% sodium chloride solution for injection USP, and was used as received. Liquid formulations of the test article (ASM8) for aerosolization was prepared by mixing TOP 004 and TOP 005 with 0.9% sodium chloride solution for injection, USP, to achieve a 1:1 mixture. The target dose solution concentrations was based on pure oligonucleotide. Therefore, a correction factor to adjust for purity was applied for weighing and dispensing the test article components. The correction factors are 1.15 for TOP 004 and 1.24 for TOP 005. Prior to the start of the 14-day exposure period, the amounts of each respective oligonucleotide required for each daily exposure was weighed out, combined (as powders) in vials designated for each day of exposure, and stored frozen at −80° C. On each day of exposure the correct vial was removed from frozen storage, the contents dissolved in the saline vehicle, filtered through a sterile 0.2-μm filter and the formulation was used for that day's exposure only.

Number of animals per group and treatments are set out in Tables 2 and 3 below:

TABLE 2

| | | No. of Animals | | | |
| --- | --- | --- | --- | --- | --- |
| | | Main Phase | | Recovery Phase | |
| Group No | Treatment | Males | Females | Males | Females |
| 1 | Vehicle Control | 3 | 3 | 1 | 1 |
| 2 | ASM8 Low Dose | 3 | 3 | — | — |
| 3 | ASM8 Mid Dose | 3 | 3 | — | — |

TABLE 2-continued

| | | No. of Animals | | | |
|---|---|---|---|---|---|
| | | Main Phase | | Recovery Phase | |
| Group No | Treatment | Males | Females | Males | Females |
| 4 | ASM8 High Dose | 3 | 3 | 1 | 1 |

Body Weight Range 2-4 kg on Day 1 of treatment
Age Range Young adults on Day 1 of treatment

TABLE 3

ASM8 exposure concentrations and dose levels (4)

| Group No. | Treatment | Dose of ASM8 (mg/kg/day), (1) | Aerosol concentration of ASM8 (mg/L), (3) |
|---|---|---|---|
| 1 | Vehicle control, (2) | 0 | 0 |
| 2 | ASM8 low dose | 0.05 | 0.00795 |
| 3 | ASM8 mid dose | 0.25 | 0.0397 |
| 4 | ASM8 high dose | 2.5 | 0.3976 |

(1): Based on an estimated body weight of 2.5 kg.
(2): Vehicle control animals were exposed to an aerosol generated from vehicle solution at an aerosol concentration considered to be equivalent in terms of mass to that generated for high-dose group.
(3): The target dose and aerosol concentrations were based on absolute purity of the test articles, which were achieved by utilizing the appropriate correction factors for purity in the dose solution formulation process.
(4): Achieved dose levels during the exposure period were estimated using the following formula: $D_L = E_c \times RMV \times T/BW$, where,
$D_L$ = Achieved dose levels (mg/kg/day)
$E_c$ = Actual concentration delivered to animals (mg/L air)
RMV = Minute volume (mL/min) estimated according to the formula of Bide et al., 2000, J. App. Toxicol., 20, 273-290. as detailed : RMV (L) = $0.499 \times W(kg)^{0.809}$
T = Time, duration of daily exposure (min)
BW = Mean body weight (kg) during exposure period.

This estimation of achieved dose assumed 100% deposition within the respiratory tract.
In-life observations including mortality, clinical examinations, body weight, food consumption, electrocardiography, ophtalmoscopy, clinical pathology, plasma level determinations, hypersensitivity testing, were performed on all animals. Upon completion of the treatment period, the animals were euthanized and subjected to anatomic pathology tests, necroscopy, organ weights, histopathology.
Semi-quantitative RT-PCR was used to measure whether there was any ASM8 inhibitory effect on the common beta-chain and the CCR3 mRNA expression on trachea samples from the high dose treated cynomolgus monkeys 24 hrs after ASM8 administration.
HL-ELISA for Oligonucleotide Measurements in Monkey Plasma Monkeys blood samples (approximately 1 mL each) were collected from each animal on Days 1 and 14 at pre-dose, 0.5, 1, 3, 6 and 24 hours post-dose. The blood samples were centrifuged at 4° C. to generate plasma, and the plasma was separated and frozen on dry ice until analyzed for determination of TOP004 and TOP005 (and proximal n−1 metabolites) concentrations using hybridization/ligation ELISA quantification assay.

Standard curve solution for oligonucleotide was prepared by serial dilutions for monkey plasma samples. Usual standard curve working range is 125 nM to 0.007629 nM. Plasma samples were diluted appropriately for measurement in the linear portion of the standard curve, making more than one dilution for accurate measurement.

Each standard or plasma sample was aliquoted (200 microL) in a 96-well polypropylene plate in which 200 microL of appropriate template probe solution was added to the 200 microL of plasma sample and incubated at 37° C. for 60 minutes. 150 microL was transferred to a NeutrAvidin coated plate in duplicate and incubate 37° C. for 30 minutes. This was washed 4 times with washing buffer using plate washer (200 microL each). 150 microL ligation probe solution was added followed by incubation at room temperature for 120 minutes. Following incubation, the sample was washed 2 times with washing buffer using plate washer (200 microL each) followed by washing 3 times with ddH2O using plate washer (200 microL). 150 microL of 1:2000 dilution (in Super block, Peirce) of anti-DIG-AP was added followed by incubation at room temperature for 30 minutes. The sample was washed 4 times with wash buffer using plate washer (200 microL). 150 microL of 10 microM MUP reagent was then added followed by incubation at room temperature for 60 minutes. Fluorescence at 355ex/485em was read.

Solutions Used in HL-ELISA:

Template Probe solution (0.05 microM Template probe, 60 mM Na2HPO4 pH 7.4, 0.9M NaCl, 0.24% Tween-20; 10× Ligation Buffer (0.8248M Tris-Cl pH 7.5, 0.0828M MgCl2, 1.93% DTT; ATP 100 mM solution (Prepare in water and adjust to pH 7±0.5 with NaOH); Ligation Probe Solution (0.067 microM oligo in 1× Ligation Buffer, 0.025 Units/mL T4 DNA ligase, 0.05 mM ATP; Washing buffer (25 mM Tris-Cl pH 7.2, 0.15M NaCl, 0.1% Tween)

Monkey Trachea Homogenization and RNA Extraction

Monkey trachea were homogenized using a polytron PT 1200 (Brinkmann Instruments) and total RNA was extracted using the Qiagen RNAeasy mini kit (Qiagen, Mississauga ON, Canada) followed by DNase I digestion. Total RNA was quantified using the Ribogreen Fluorescent Assay (Invitrogen Corporation, Burlington ON, Canada). cDNA was prepared from 1-2 microg RNA using the First-Strand cDNA Synthesis Using SuperScript™ II RT kit (Invitrogen Corporation, Burlington ON, Canada)

RNA Extraction, Reverse Transcription and Polymerase Chain Reaction

RNA was extracted from cell pellets according to Qiagen RNAeasy mini Kit protocol using the QiaVac 24 manifold from Qiagen and RNA was treated with DNase-I according to Fermentas procedures. RNA was quantified using the RiboGreen reagent according to the manufacturer protocol. Otherwise, RNA was quantified using a spectrophotometer. Preparation of first-strand cDNA was performed using the Superscript First-Strand Synthesis System for RT-PCR kit from Invitrogen, in a total reaction volume of 20 microL. Briefly, 1-2.5 microg of RNA were first denatured at 65° C. for 5 minutes, with 0.5 mM of each dNTPs, 0.5 microg of oligo $(dT)_{12-18}$ and chilled on ice for at least 1 min. The mixture was incubated at 42° C. for 2 minutes and a second pre-mix containing 1× First-Strand Buffer, 10 mM DTT, 40 units of RNaseOUT and 40 units of SuperScript II RT was added. Reactions were incubated at 42° C. for 10 minutes, at 50° C. for 1 hour and inactivated by heating at 70° C. for 15 minutes. PCR was performed with optimized quantity of cDNA (100-250 nanog for CCR3 and 1-10 nanog for G3PDH) in 1×PCR buffer (10×: Tris-HCl, KCl, $(NH_4)_2SO_4$, 15 mM $MgCl_2$; pH8.7) in a total reaction volume of 50 microL, 0.2 mM of each dNTPs, 8.5 pmol of each PCR primer and 2.5 units of Taq DNA Polymerase. The mixture was heated at 94° C. for 5 minutes, followed by 30-35 cycles, each consisting of incubation for 1 minute at 94° C., 45 seconds at 60° C. and 45 seconds at 72° C. Supplemental elongation was performed at 72° C. for 10 minutes. PCR products were analyzed by 1.5% agarose gel electrophoresis in the presence of ethidium bromide. Quantification of PCR products was performed using the Total Lab software (Background subtraction with Rolling Ball; Ultra Lum Inc., Model UC4800).

The PCR primers were: Human CCR3 primer pair (R&D systems, cat# RDP-209-025); Human GAPDH primer pair (R&D systems, cat# RDP-39-025) and primers shown in Table 4. Control experiments were systematically included and consisted of PCR on non RT-RNA.

TABLE 4

| Primer ID. | Primer sequence: 5'-3'. | SEQ ID NO. |
|---|---|---|
| huBcATG.for | 5-ATGGTGCTGGCCCAGGG-3 | 15 |
| huBcATG1.for | 5-CCAGGGAGATGGTGCTGG-3 | 16 |
| huBc6.rev | 5-CCGCTTGTAGACCACCTCAAC-3 | 17 |
| huBc7.rev | 5-CCTTGGCTGAACAGAGACGATG-3 | 18 |
| mkCCR3.for | 5-TGCTCTGTGAAAAAGCCGATG-3 | 19 |
| mkCCR3-2.rev | 5-ACCAAAAGTGACAGTCCTGGC-3 | 20 |
| huBc4.for | 5-AAGTCAGGGTTTGAGGGCTATG-3 | 21 |
| huBc4.rev | 5-CAAGGGGGCAGAGACAGGTAG-3 | 22 |
| G3pdh.for | 5-ACCACAGTCCATGCCATCAC-3 | 23 |
| G3pdh.rev | 5-TCCACCACCCCTGTTGCTGTA-3 | 24 |

Oligonucleotide Chemical Degradation

To induce degradation of TOP 004 and TOP 005 prior to analysis (in order to ensure resolution of degradation products from the intact molecules), the following treatments were performed:
*Depurination: ASM8 was resuspended in 30% CH3COOH at a final concentration of 0.5 mg/mL, and incubated for 3, 4, or 6 hours at room temperature. The reaction was stopped by addition of 5 volumes of water and the mixture placed at −20° prior to lyophilization in a Speed-Vac to remove acetic acid.
*Cleavage: the depurinated oligonucleotides were resuspended in 0.2 M NaOH (0.5 mg/mL), incubated at 50° C. for 1 hour, and stored at −20° C. or analyzed by HPLC.
HPLC Fractionation of TOP004 and TOP005

ASM8 was weighted, and solubilized in PBS at a concentration of 0.5 mg/mL (0.25 mg/mL TOP004 and 0.25 mg/mL TOP005). HPLC gradient parameters are shown below in Table 5.

TABLE 5

HPLC gradient parameters:

| Time (min) | Flow (ml/min) | % Buffer A | % Buffer B |
|---|---|---|---|
| 0 | 1 | 100 | 0 |
| 5 | 1 | 100 | 0 |
| 10 | 1 | 93 | 7 |
| 100 | 1 | 65 | 35 |
| 102 | 1 | 20 | 80 |
| 122 | 1 | 20 | 80 |
| 124 | 1 | 100 | 0 |
| 144 | 1 | 100 | 0 |
| 146 | 0.1 | 100 | 0 |

HPLC separation was performed with a Waters 1500 Series Binary HPLC pump coupled to a Waters 2487 Dual λ Absorbance detector and equipped with in-line degasser, oven, and 1500 series manual injector, Reodyne 7725i. The mixture of oligonucleotides was fractionated on a Waters Protein Pak DEAE 5PW anion exchange column (0.5 cm×75 cm), maintained at 60° C., and detected by UV absorption at 260 nm. The oligonucleotide mixture (volume=25 microL) was loaded onto the column in water (buffer A: water (MilliQ grade)) and the elution was performed by progressively increasing the proportion of buffer B (1 M LiClO$_4$, (0.22 micrometer filtered)), resulting in an increase of ionic strength of the liquid phase, which eluted the oligonucleotide from the solid phase (column).

Under the assay conditions, 62.5 microg of either TOP 004 or TOP 005 produced a measurable change >0.15 absorbance unit (AU) at 260 nm.

Oligonucleotide Storage

Aliquots of ASM8 (0.5 mg/mL) in PBS were incubated at −20° C., 4° C., 30° C., and 40° C. for 2 months. At weeks 4, and 8, the HPLC profile of ASM8 was established. The control condition was defined as the HPLC profile of ASM8 prior to any storage time (i.e., at time zero). The HPLC system was driven by Breeze™ (V 3.30) software from Waters.

Oligonucleotide Melting Curves and Thermodynamic Summary Tables

TOP 004 and TOP 005 were mixed at equimolar concentrations in 1×PBS (as well as in other buffer systems). Total oligonucleotide concentration ranged from approximately 1.2 to 8.7 mM. Standard UV thermo-denaturation methods were conducted using a Beckman DU640 spectrophotometer with a Tm accessory. Change in absorbance was detected at 260 nm at each degree from 10 to 90° C. Melting curves were fitted using MELTWIN™ 3.5 software to determine thermodynamic parameters. Screen pictures of melting curves and thermodynamics summary tables were produced.

Example 1

Efficacy of Antisense Oligonucleotides Directed to the CCR3 Receptor

Several antisense oligonucleotides directed to the CCR3 chemokine receptor were analyzed for their ability to inhibit mRNA expression of the receptor and inhibit the function of the receptor. The CCR3 antisense primary screening was performed in Eol-1 and U937 cell lines. These cells express CCR3 mRNA under the normal cell culture conditions described above. Table 6 shows antisense oligonucleotides directed against the human CCR3 chemokine receptor.

Referring to Table 6, antisense oligonucleotide 828 directed against the CCR3 receptor (828: 5'-GTTACTACT-TCCACCTGCCTG-3' SEQ ID NO. 1) is effective in inhibiting mRNA expression of the receptor as shown in Table 6.

The oligonucleotide 828 is directed against the CCR3 gene and begins 48 bases after the end of exon 1 and is 21 bases long. BLAST searches were performed on 828 and, other than to the CCR3 receptor, the next closest homology is reported at less than 72% homology. This is considered to be insignificant homology for achieving the complete association of two complementary sequences. The specificity of 828 was assessed by using a mismatch oligonucleotide (SEQ ID NO. 32). The mismatch had no effect on CCR3 mRNA or house keeping gene G3PDH used as internal control in these experiments. The antisense oligonucleotide 828 is therefore specific.

TABLE 6

| Antisense Identification | Antisense Sequence 5'-3' | % of CCR3 mRNA inhibition |
|---|---|---|
| 773 | 5-TGGAAAAGCGACACCTACCTG-3 (SEQ ID NO: 2) | 73% |

TABLE 6-continued

| Antisense Identification | Antisense Sequence 5'-3' | % of CCR3 mRNA inhibition |
|---|---|---|
| 828 | 5-GTTACTACTTCCACCTGCCTG-3 (SEQ ID NO: 1) | 71% |
| 786 | 5-CCCTTTTCCTGGAAAAGCGACA-3 (SEQ ID NO: 3) | 45% |
| 788 | 5-CTCCCTTTTCCTGGAAAAGCG-3 (SEQ ID NO: 4) | 37% |
| 793 | 5-TCCACCTCCCTTTTCCTGGA-3 (SEQ ID NO: 5) | 35% |
| 807 | 5-CCTCCTTGTTCCACCTCCCTT-3 (SEQ ID NO: 6) | 31% |

Example 2

Efficacy of Two DAP-Substituted Oligonucleotides in Monkey Peripheral Blood Mononuclear Cells (PBMCs)

As discussed above, antisense oligonucleotides 107A and 828 were modified by substituting adenosine with DAP to produce antisense oligonucleotides TOP004 and TOP005 respectively. TOP004 (5'-GGGTCTGCXGCGGGXTGGT-3' (SEQ ID NO: 13), where X represents a DAP modification of an adenosine residue), as with 107A, is a 19-mer directed to the common beta-chain of the IL-3, IL-5, and GM-CSF receptors. TOP005 (5'-GTTXCTXCTTCCXCCTGCCTG-3' (SEQ ID NO: 14)), as with 828, is a 21-mer directed against the chemokine receptor CCR3.

The efficacies of TOP004 and TOP005 were tested both separately and in combination. ASM8 is a composition that comprises, in part, both TOP004 and TOP005. The efficacy studies were performed in monkey peripheral blood mononuclear cells (PBMCs), to validate the use of this species to explore the potential for toxic effects arising from the pharmacological activity of ASM8.

For ASM8 to be effective in the Cynomolgus monkey, sufficient homology to their target sequences must exist. The Cynomolgus Beta-chain sequence is not available from public databases and thus the segment encompassing the TOP004 sequence region was cloned and sequenced. However, the activity of TOP004 across primate species can be assessed directly in a relevant in vitro system. Specifically, a peripheral blood mononuclear cell (PBMC) preparation is a suitable system to test the functionality of TOP 004, since the common beta-chain is found on most of the mononuclear leukocyte sub-populations (T and B cells, monocytes, and macrophages).

Sequence information for the cynomolgus monkey CCR3 receptor is available only for the coding region; no sequence information for the TOP005 binding region is available in the public databases. The TOP005 target sequence begins 48 bases after the end of exon 1 of the human gene; this intron spans more that 20 kilo base pairs, rendering its cloning and sequencing very tedious. Reports in the literature have shown that some segments of intron sequences are conserved between human and monkey (Rahman et al., 2004. Genomics. 8376-84). Evolutionary studies also show that segments of homologous intronic sequences are found across taxa (human, whale and seal), and that these segments are found more often near the intron-exon junctions (Hare M P and Palumbi S R., 2003 Mol Biol Evol. 20, 969-978). Functionality of TOP005 in monkeys was tested in a PBMC preparation in which expression of the CCR3 receptor is found on T and B cells subsets.

Sequencing of the Cynomolgus Monkey Common β Chain

Analysis of common beta-chain for IL3/IL-5/GM-CSF receptor genes from human, chimpanzee, pork, mouse and rat revealed a high degree of gene sequence similarity among vertebrates. Primer sequences for cloning PCR were designed. The primer sequences were derived from highly conserved nucleotide sequences in human, chimpanzee, pork, mouse and rat, surrounding the TOP004 oligonucleotide region of common beta-chain gene. Table 2 shows the different primers. These primers were used to amplify specific products from Cynomolgus PBMC cDNA. Several PCR products were obtained, depending on the set of primers used. A nested PCR round was used to assess the specificity of the obtained products. The positive amplicons were cloned and sequenced.

FIG. 1A shows the sequences of three clones (SEQ ID NO.'s 25, 26 and 27 respectively) obtained from PCR amplification of the cynomolgus TOP004 region aligned to the human sequence (SEQ ID NO. 28) and the corresponding region in chimpanzee (SEQ ID NO. 33), pork (SEQ ID NO. 34), rat (SEQ ID NO. 35) and mouse (SEQ ID NO. 36) nucleotide sequences. Non-homologous nucleotides are shown with lower cases while conserved regions are shown in upper case. The TOP004 region is underlined. The Cynomolgus beta-chain sequence complementary to the TOP004 region showed significant homology (18 of 19 bases identity) in all of the three clones sequenced. The difference was found at position 6 (starting from the 5' end of TOP 004), where both an "A" and a "G" were found ("A" being the expected base).

FIG. 1B shows the alignment of protein sequences predicted from the cloned Cynomolgus (SEQ ID NO. 37) and known nucleotide sequences from Human (SEQ ID NO. 38), chimpanzee (emb. AADA01213660) (SEQ ID NO. 39); pork (U94688.1) (SEQ ID NO. 40); mouse (NM_007780.1) (SEQ ID NO. 41) and rat (NM_133555.1) (SEQ ID NO. 42). The nucleotide discrepancy found at position 6 (starting from the 5' end of TOP 004 where both an "A" and a "G" were found) corresponds to the second base of the Glutamine (Q) or Lysine (K) codon in the common beta-chain of available protein sequences in the public data bank. The data presented in FIG. 1B shows that highly evolved species contain a Glutamine residue (arrow in human, chimpanzee, pork), in the TOP004 complementary region. Glutamine is encoded by 2 codons, CAA or CAG. In lower species (mouse and rat), the Glutamine is substituted by a lysine residue. Lysine is encoded by 2 codons, AAA or AAG. In either case, an Adenosine at the second position is conserved. As such, the Adenosine residue is a likely candidate for the Monkey sequence to be functional as it is in the other higher vertebrates. However, GM-CSF beta-chain polymorphisms cannot be ruled out. Freeburn et al. discloses several mutations in the intra-cytoplasmic region of the beta-chain receptor, which could be accounted for susceptibility to leukemia, (Freeburn et al., 1997, Exp. Hematol., 25:306-311). The sequencing data presented in FIG. 1A shows that a guanosine residue can occur at position 6 starting from the 5' of the underlined TOP004 sequence. In this case, the codon will be CGG and the protein sequence will contain an Arginine (R) residue at that position. A basic base (H, K or R) in that position is reminiscent of lower vertebrates and is unlikely the case for primates.

Despite this discrepancy, the very high degree of identity between the monkey and the human beta-chain sequence suggests functionality of TOP004 in cynomolgus monkey.
TOP 004 and TOP005 Efficacy in Cynomolgus Monkey PBMCs TOP 004 and TOP005 were tested individually in cynomolgus monkey PBMCs for their ability to selectively decrease the expression of the beta-chain and CCR3, respectively. Purified monkey PBMCs were incubated with different concentrations of TOP004 and TOP 005.

Referring to FIGS. 2A and 2B, results from experiments performed on more than 10 bloods obtained from monkeys are presented in bar graph A and in bar graph B. The bar graphs show reduced beta-chain and CCR3 mRNA expression with TOP004 (A) and TOP005 (B) in monkey PBMC. The inhibition was specific for TOP004 and TOP005 and not due to RNA degradation or to loss of cell viability, as evidenced by the internal control (451-bp product corresponding to G3PDH mRNA and cell viability test). TOP004 specifically reduced the expression of the common β-chain in primary monkey PBMCs as measured by RT-PCR (FIG. 2A). Maximum efficiency was obtained with concentrations of 10 to 15 microM, where >50% inhibition was mostly observed. The inhibition of monkey beta-chain by TOP004 confirmed the sequencing data (FIG. 1A) that showed a very high degree of identity between the human and the monkey beta-chain mRNA sequences. Similarly, transfection of TOP005 into monkey PBMCs diminished the expression of CCR3 mRNA, as measured by RT-PCR (FIG. 2B). Maximum inhibition for the CCR3 mRNA expression by TOP005 was obtained at lower antisense oligonucleotide concentrations (0.05 to 2.5 microM) than for the 0 chain (10 to 15 microM).

The inhibition of mRNA expression, as measured by RT-PCR was also corroborated at the protein level by flow cytometry (FACS). Monkey PBMCs were incubated for 36 hrs in growth media in the presence of various concentration of either TOP004 or TOP005. Flow cytometry quantification was done as described above. Referring to FIGS. 3A and 3B, bar graphs show beta-chain and CCR3 cell surface expression in the presence of TOP004 and TOP005 respectively in cynomolgus monkey PBMCs. The graphs show that, after treatment with TOP004 or TOP005, a reduction in the percentage of cells expressing the beta-chain and CCR3 of greater than 30% was achieved at 7.5 microM and 0.5 microM, respectively, was observed.

TOP004 and TOP005 were also tested in combination, in a 1:1 ratio (ASM8), in Cynomolgus monkey PBMCs for their ability to selectively decrease the expression of the beta-chain and CCR3, respectively. Monkey PBMCs were incubated overnight in the presence of various concentration of ASM8 before the expression of the beta-chain and CCR3 was assessed by RT-PCR. Referring to FIGS. 4A and 4B, bar graphs representing beta-chain and CCR3 mRNA expression in the presence of ASM8 in cynomolgus monkey PBMCs are shown for more than five (5) bloods obtained from monkeys. Significant inhibition of the beta-chain was observed with concentrations of ASM8 ranging from 2.5 to 5 microM (FIG. 4A), which is lower than the optimal concentration range giving the maximum inhibition by TOP004 alone (between 10 to 15 microM (FIG. 2A)). These results show that the combination of TOP004 and TOP005 antisenses provides enhanced-potency and synergy of ASM8 at blocking beta-chain expression, compared to TOP004 alone. Similarly, transfection of ASM8 into monkey PBMCs diminished the expression of CCR3 mRNA, as measured by RT-PCR (FIG. 4B). Maximum inhibition for the CCR3 mRNA expression by TOP005 was obtained at lower antisense oligonucleotide concentration (0.05 to 5 microM) than for the beta-chain (2.5 to 5 microM). The effect for ASM8 on CCR3 inhibition was not clearly concentration-dependent, this result may reflect that maximum inhibition (plateau) is reached at lower concentration for CCR3 than for the beta-chain.

In summary, sequencing of the cynomolgus common beta-chain indicated a very high degree of identity (at least 18 out of 19 bases that encompass the TOP004 sequence). It was expected that this high degree of homology with the human gene will allow for the sufficient hybridization of TOP004 to the monkey beta-chain mRNA to induce antisense activity and thereby diminish its expression.

TOP 004 was transfected in purified cynomolgus PBMCs to evaluate its ability to downregulate the expression of the monkey 0 chain. TOP004 effectively decreased the expression of β chain mRNA, measured by RT-PCR, by 30 to 70%.

Similarly, TOP005 was transfected in cynomolgus monkey PBMCs and the level of CCR3 expression determined by semi-quantitative RT-PCR. The results demonstrate that TOP005 down-regulates the expression of the cynomolgus CCR3 in a range varying between 30% and 85%.

In the same way, the transfection of either TOP004 or TOP005 in monkey PMBCs induced a specific reduction at 0.5 microM (>30%) in the number of cells positive for the beta-chain or CCR3, measured by flow cytometry.

ASM8 was also transfected in purified monkey PBMCs to evaluate the efficacy of the combined treatment (TOP 004 and TOP 005) to downregulate the expression of the monkey beta-chain and CCR3, mRNA. In these conditions, ASM8 significantly reduced the expression of the beta-chain and CCR3, measured by RT-PCR, at concentration of ASM8 as low as 0.1 to 0.5 microM. This also suggests that cynomolgus monkey is an appropriate species in which to examine potential toxic effects due to the pharmacological activity of ASM8.

Example 3

Effect of Antisense Oligonucleotides Directed Against CCR3 in Human Cells and Cell Lines Further experiments were performed to assess the ability of A86 and TOP005 to inhibit CCR3 mRNA expression in HL-60 differentiated eosinophil like cells (Lee Tiffany et al, J. Immunol 1998, 160:1385-92), U937 and Eol-1 cells as well as in peripheral blood mononuclear cells (PBMC). The ability of A86 and TOP005 to inhibit eosinophil cell migration and calcium mobilization in both HL-60 cells and human purified peripheral blood eosinophils was also investigated. A86 is an antisense oligonucleotide (5'CTG GGC CAT CAG TGC TCT G 3' (SEQ ID NO. 29) that corresponds to the 87-105 nucleotide sequence of the coding region (exon 7) of CCR3. As discussed earlier, TOP005 is 828 but with all three adenosines replaced by 2,6 diaminopurine (5'GTT XCT XCT TCC XCC TGC CTG 3' (SEQ ID NO. 14)). The 828 complementary sequence begins 48 bases after the end of exon 1 and is 21 bases long. As controls for A86, a complementary sense oligonucleotide (5' CAG AGC ACT GAT GGC CCA G 3' (SEQ ID NO. 30)) and a mismatch (5' CGT GGC ACT CAG TGT CCT G 3' (SEQ ID NO. 31)) were used. As a control for 828/TOP005, a mismatch (5' CCT TTG ACC TGC CAA TGC TCT 3' (SEQ ID NO. 32)) was used.

Figure 5:
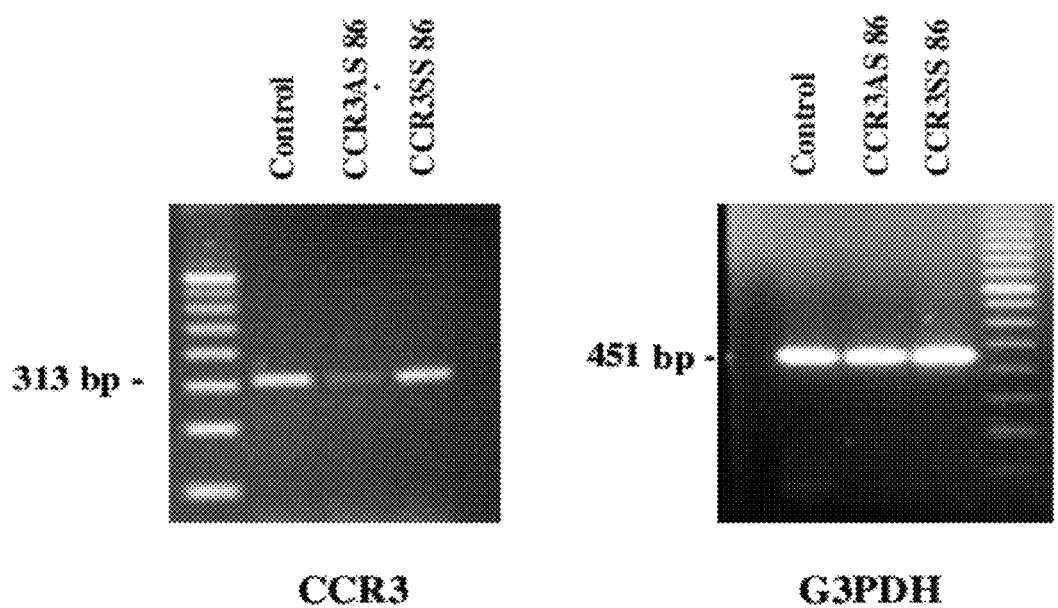
FIG. 5 shows the effect of oligonucleotides on CCR3 mRNA expression in HL60 differentiated cells. Antisense oligonucleotide A86, directed against CCR3, is shown to decrease CCR3 mRNA expression when compared to control and sense oligonucleotides with no effects on G3PDH expression.

Effect of A86 Antisense Oligonucleotides on the CCR3 mRNA Expression in HL-60 Clone 15-Derived Eosinophils It is known that the clone 15 variant of HL-60 cells can be induced by butyric acid treatment to differentiate into cells having many characteristics of peripheral blood eosinophils (Lee Tiffany et al, J. Immunol 1998, 160:1385-92). Using the same differentiation protocol, we confirmed the expression of CCR3 mRNA in differentiated HL-60 cells. RT-PCR was then performed to examine the abilities of synthetic oligonucleotides to modulate the expression of mRNA coding for the CCR3 receptor in HL-60 cells differentiated into eosinophils. After cells treatment with 10 microM of A86, CCR3 mRNA was assessed by semi-quantitative PCR using as internal control G3PDH. Total RNA was isolated from freshly harvested cells as described above. Referring to FIG. 5, the effect of antisense oligonucleotides against CCR3 on CCR3 mRNA expression in HL60 differentiated cells is shown. In contrast to sense oligonucleotides, and mismatch oligonucleotides, antisense oligonucleotides inhibit markedly the expression of CCR3 mRNA. The expression of CCR3 mRNA in cells treated with sense oligonucleotides and mismatch oligonucleotides was not significantly different from that obtained in non-treated cells. Moreover, all oligonucleotides at the concentration used did not affect G3PDH mRNA expression. Antisense oligonucleotide A86 used in this experiment is therefore able to inhibit specifically CCR3 mRNA expression.

Effect of A86 on CCR3 Protein Cell Surface Expression

It was further investigated whether the decrease mRNA for CCR3 could reflect that of the CCR3 cell surface protein density. In this respect, flow cytometric analysis was performed to assess the expression of CCR3 receptor on HL-60 derived eosinophils after treatment with oligonucleotides. After butyric acid treatment, the percentage of HL-60 derived eosinophils expressing CCR3 receptor was 40%. When treated with sense and mismatch oligonucleotides (10 microM), the percentage of positive cells were slightly and non-significantly decreased; the percentage of positive cells was 35% and 38% respectively. However, the density of CCR3 receptor on cells treated with A86 was significantly reduced (26% of positive cells versus 40% in non-treated cells). A86 at 10 microM is able to reduce CCR3 cell surface expression by 65%. The effect of A86 was more significant at higher concentrations. Specifically, 20 and 30 microM of A86 was used and the results show that CCR3 cell surface expression was decreased by 75% and 85% respectively. A86, an antisense oligonucleotide to CCR3, is able to inhibit CCR3 cell surface expression in a dose dependent manner.

Effect of A86 on Eotaxin Induced Calcium Mobilization in HL-60 Cells

Figure 6:
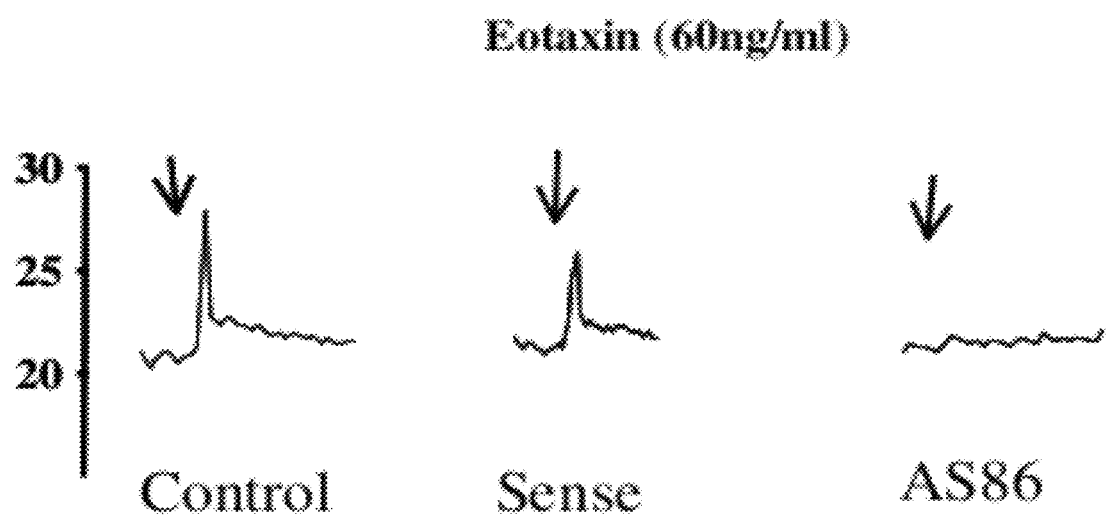
FIG. 6 shows a calcium mobilization assay in oligonucleotide-treated HL-60 cl-15 cells. The decreased mobilization in response to eotaxin in A86 treated cells is compared to the control and the sense oligonucleotides treated cells.

A rapid transient flux of calcium is typically observed when leucocytes are stimulated by chemokines for which they express a specific receptor. This calcium mobilization can be followed in real time by Fura-2AM loaded cells and is a convenient measure of receptor activation. The chemokine Eotaxin is a specific ligand for CCR3 receptor and induces a rapid calcium influx and leukocytes chemotaxis upon ligation to the receptor. Referring to FIG. 6, the effect of A86 on CCR3 activation is shown. Calcium mobilization in response to eotaxin was decreased in A86 treated cells when compared to control and sense oligonucleotides. Cells were treated with A86 oligonucleotide at the concentration of 10 microM. Cells treated with sense oligonucleotide were able to respond to eotaxin as non-treated cells did. In these conditions, eotaxin induces an increase in the intracellular concentration of $Ca^{++}$. However, in cells treated with A86, eotaxin induced much less $Ca^{++}$ mobilization. The results presented here show that A86 was effective at interfering with CCR3 receptor activation in HL-60 cell line.

Figure 7:
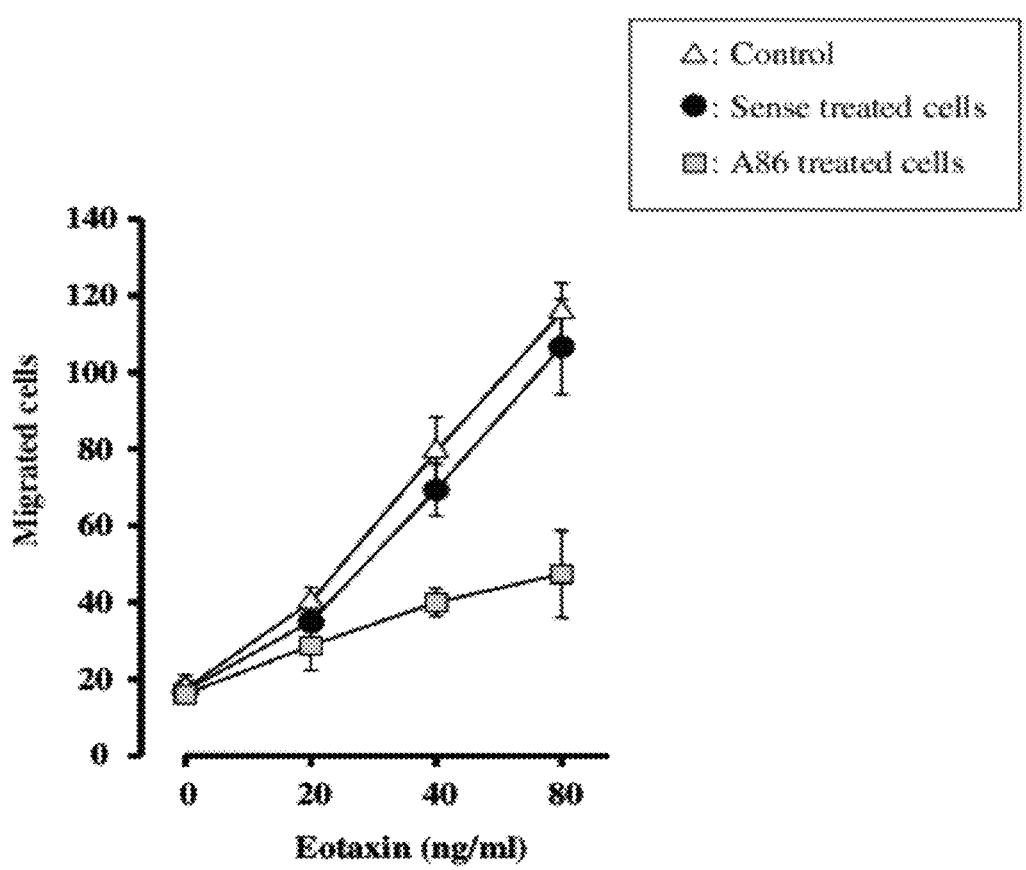
FIG. 7 shows the effect of oligonucleotides on the chemotactic response of purified human eosinophils to eotaxin. Relative chemotactic response of A86 treated eosinophils is compared to control and sense treated cells.

Treatment of Purified Human Eosinophils with Antisense Oligonucleotides Inhibit their Response to Eotaxin Referring to FIG. 7, the effect of antisense oligonucleotides on chemotactic response of purified human eosinophils to eotaxin is shown. Purified human eosinophils were incubated overnight with antisense oligonucleotides (squares) or sense oligonucleotides (circles) at the concentration of 10 microM, in RPMI 1640 supplemented with 5% FCS and IL-5 (1.5 ng/mL). Control cells (triangles) were incubated in the same conditions without ODNS. Data are from a single experiment representative of three and are presented as the mean number of migrated cells±SD of triplicate determinations of migrating cells per 5 high-power fields. Eosinophil migration was inhibited by antisense oligonucleotides against CCR3 and this inhibition was more significant when eotaxin concentration was increased. At 80 ng/mL of eotaxin, eosinophil migration was decreased by 55.6%.

Figure 8:
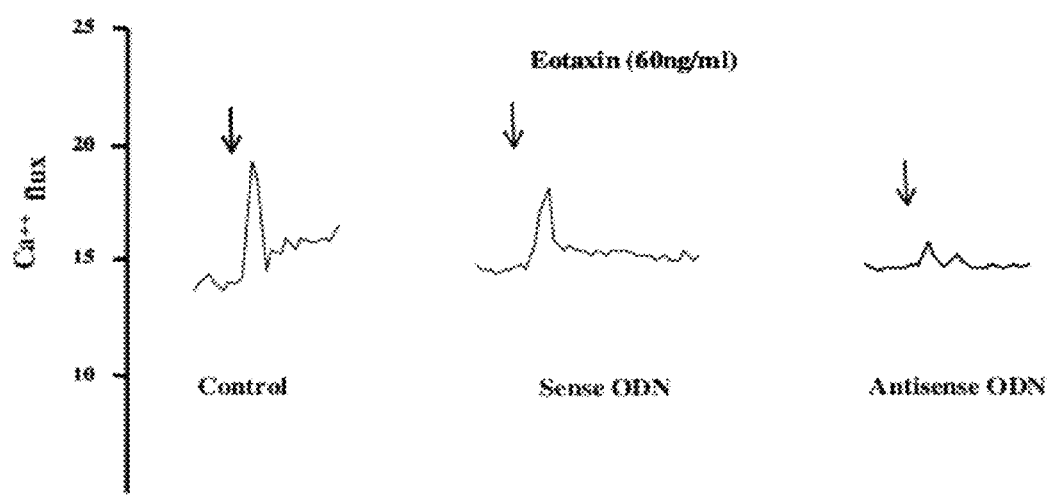
FIG. 8 shows a calcium mobilization assay in oligonucleotide-treated eosinophils in response to eotaxin. Calcium mobilization is compared in eosinophils treated with A86 and control or oligonucleotide sense treated cells.

FIG. 8 shows calcium mobilization in eosinophils treated with antisense oligonucleotides. When eosinophils cells are treated with A86 (10 microM), $Ca^{++}$ mobilization induced by eotaxin was also inhibited when compared to control and sense oligonucleotides.

The results presented here show that A86 was potent at interfering with eosinophils chemotaxis to eotaxin, by down regulating the CCR3 receptor.

Efficacy of TOP005

Similar experiments were performed using TOP 005. TOP005 was chosen because of the efficacy of 828, results from BLAST assessment of the sequence showing that 828 had no homology to known genes, the lack of hybridization of 828 with TOP004 (experiments performed at DNA software) and its length (permitting differentiation from TOP004 when mixed together and separated by anion exchange HPLC).

Figure 9:
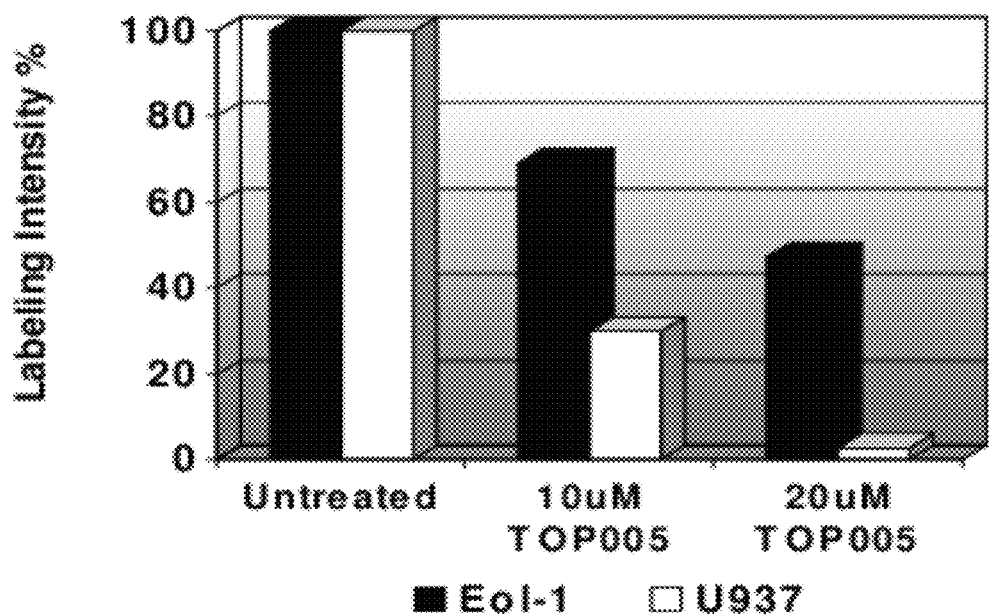
FIG. 9 shows the effect of TOP005 on cell surface expression of CCR3 presented as percent of expression vs. controls in Eol-1 and U937 cells.
Figure 11:
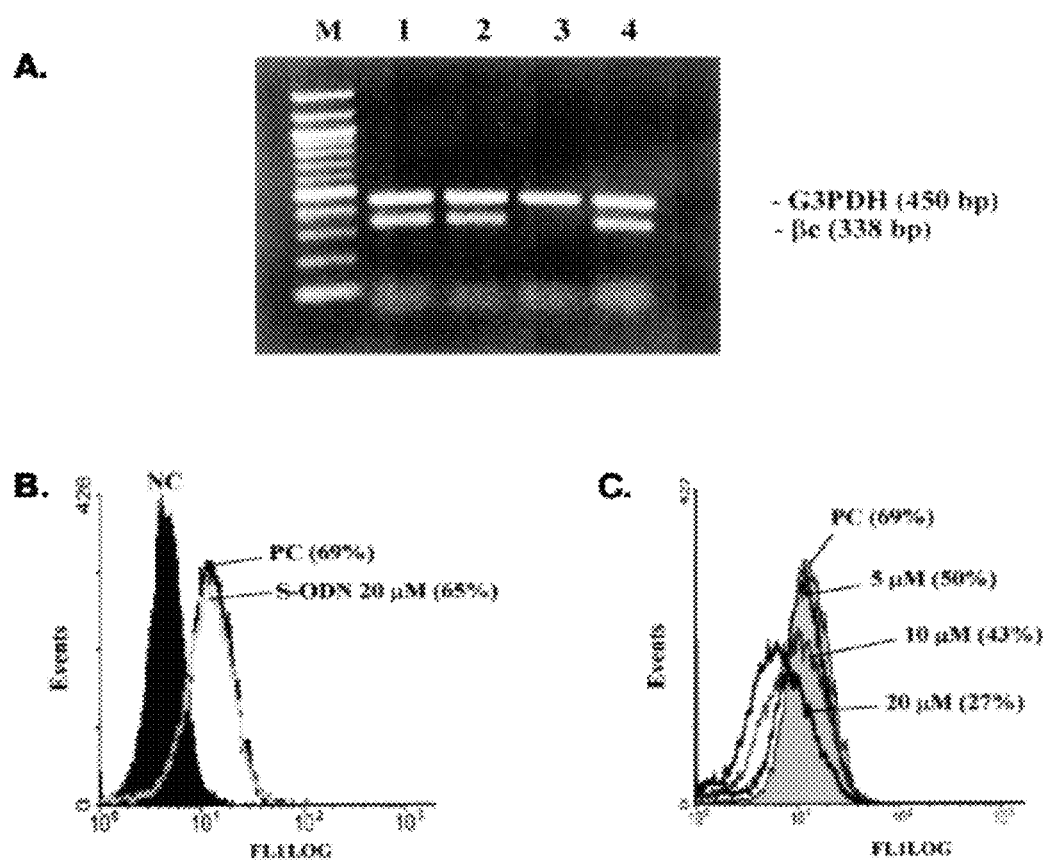
FIG. 11A shows modulation of beta-chain ($\beta_c$) mRNA expression in 107A treated TF-1 cells using RT-PCR to detect the beta-chain ($\beta_c$) mRNA or control G3PDH mRNA expression.
FIGS. 11B and 11C show the effect of sense oligonucleotide and 107A treatment on beta-chain expression on the cell surface of TF-1 cells, as determined by FACS analysis.
FIG. 11D shows the effect of TOP004 on common beta-chain expression at the mRNA and protein levels in U937 cells.
Figure 11:
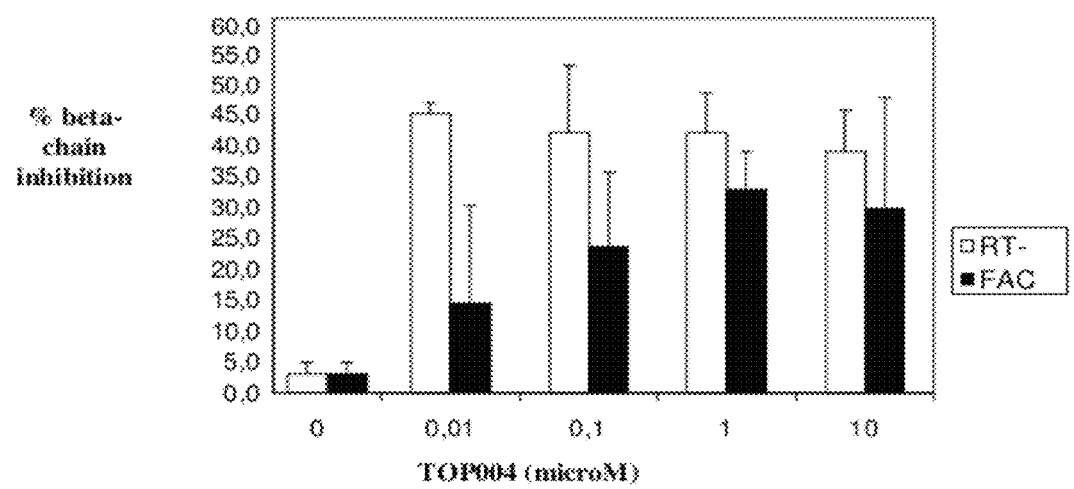

FIG. 9 shows the effect of TOP005 on cell surface expression of CCR3. The efficacy of TOP005 was assessed in Eol-1 and U937, cells. CCR3 expression was assessed by flow cytometry 36 hours after treatment with TOP 005. Results are presented as percent of expression vs. controls in Eol-1 and U937 cells. The bar graphs in FIG. 9 show that TOP005 inhibited CCR3 protein expression on the surface of U937 and Eol-1 cells.

FIGS. 10A and 10B show the effect of TOP005 on CCR3 mRNA expression in human peripheral blood mononuclear cells (PBMC). Human PBMC were either freshly isolated or cultured in human interleukin-2 (10 nanog/mL for 24 hours). They were then exposed to TOP005 and cultured for 18 hours. In FIG. 10A, Gels showing G3PDH and CCR3 expression are shown on the top. The ratio of CCR3 mRNA expression to G3PDH, normalized for controls is presented on the bottom. Referring to FIG. 10B, the bar graph shows that TOP005 is effective at decreasing PBMC CCR3 mRNA expression at doses as low as 1 microM.

Antisense oligonucleotides A86 and TOP005 can therefore inhibit CCR3 mRNA expression in Eol-1 cells (a human eosinophilic cell line), HL-60 cells differentiated into eosinophils and U937 cells. Inhibition of CCR3 with these oligonucleotides also decreased calcium mobilization in both HL-60 differentiated cells and human eosinophils as well as decreased eosinophil chemotaxis to eotaxin. Neither the corresponding sense oligonucleotides nor mismatch oligonucleotides affected the response to eotaxin.

Example 4

Efficacy of TOP004 in Reducing Expression of the Common β Chain Subunit of the IL-3, IL-5 and GM-CSF Receptors and Associated Cellular Responses in Human Cell Lines Further experiments were performed to test the effect of 107A and TOP004 on the expression of the common beta-chain subunit of the IL-3, IL-5 and GM-CSF receptors.

Modulation of Beta-Chain mRNA Expression in TF-1 and U937 Cells

Referring to FIGS. 11A, 11B and 11C, modulation of beta-chain mRNA expression in TF-1 cells is shown. TF-1 cells were treated with 107A antisense for 12 hours. Referring to FIG. 11A, RT-PCR was performed to detect the beta-chain mRNA and G3PDH mRNA expression in TF-1 cells. Cells were treated as follows: lane 1, control untreated; lane 2, sense oligonucleotide (10 microM); lane 3, 107A (10 microM); lane 4, mismatched oligonucleotide (10 microM). Semi-quantitative RT-PCR in non-saturating conditions was used to assess the expression of beta-chain and G3PDH (used as a control) mRNA. Treatment with 107A (10 microM) almost completely inhibited the beta-chain expression in TF-1 (FIG. 11A) and U937 treated cells (data not shown). The inhibition was specific for 107A and was not due to RNA degradation or to loss of cell viability, as evidenced by the internal control (450-bp product corresponding to G3PDH mRNA) (FIG. 11A). In contrast, beta-chain mRNA expression was not inhibited in untreated control cells or in cells treated with sense or mismatched oligonucleotide (FIG. 11A). Thus, 107A activity was both specific and effective in inhibiting the expression of beta-chain mRNA.

Referring to FIGS. 11B and 11C, the effect of sense oligonucleotide and 107A treatment on beta-chain expression on the cell surface of TF-1 cells, as determined by FACS analysis, is shown. FIG. 11B shows the untreated controls (PC) vs. sense oligonucleotide treated (S-ODN) and where NC represents a negative control. FIG. 11C shows cell surface expression in cells treated with 107A (at varying concentrations of 5, 10, and 20 microM) for 36 hours. The ability of antisense oligonucleotides to inhibit cellular beta-chain protein expression resulted in a corresponding lower density of beta-chain subunit on the surface of 107A-treated cells. A monoclonal antibody (MAb) against the common beta-chain protein of GM-CSF/IL-3/IL-5 receptors was used, together with FACS analysis, to measure the cell surface expression of beta-chain protein on TF-1 cells. The level of beta-chain expression by untreated TF-1 cells was very high and was not affected by sense oligonucleotide treatment. However, increasing concentrations of 107A (5, 10, and 20 microM) significantly reduced the level of beta-chain expression in a dose-dependent manner (the percentage of cells testing positive in FACS analysis decreased from 69.9% to 27.8%).

FIG. 11D shows the inhibition of the expression of the common beta-chain in U937 cells following TOP004 treatment. U937 cells were incubated in the presence of incremental concentrations of TOP004 (0.01, 0.1, 1 and 10 microM) for 12 hours in serum-free media before RT-PCR and 48 hours before FACS analysis. The percentage of the common beta-chain mRNA or protein inhibitions was determined by comparing values obtained to that of untreated cells. The experiment was performed in triplicate and the data represents average+/−SE. The results presented in FIG. 11D demonstrate that TOP004 antisense, which is the DAP containing residues homologous to 107A antisense, is effective at inhibiting the common beta-chain at the mRNA and protein levels. Moreover, small amounts of TOP004 (e.g., 1 microM) were found sufficient to knock-down the beta-chain mRNA as well as the corresponding protein. Thus, this data favours the efficacy of DAP chemistry and its use in pharmacological compositions as described above.

Cell Survival and Functional Studies

Figure 12:
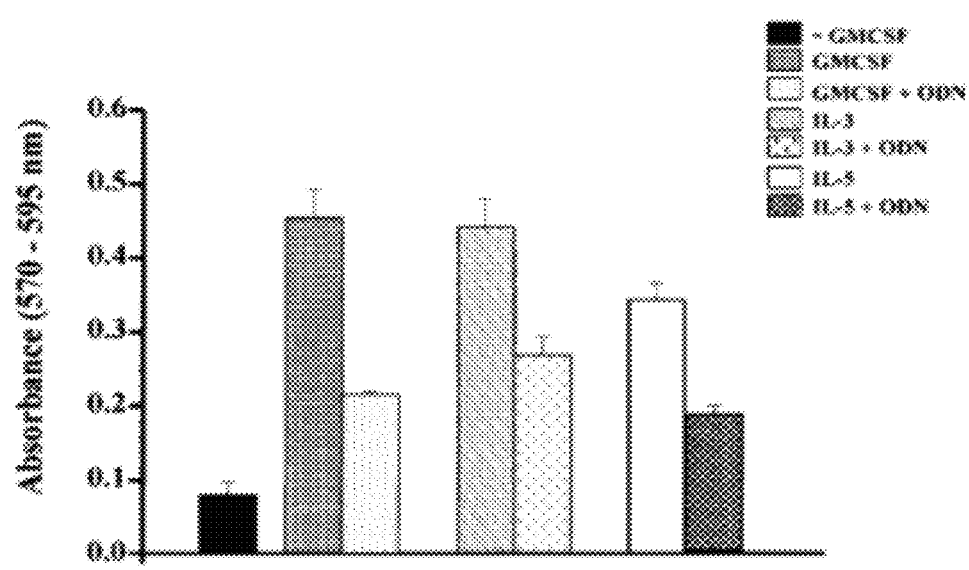
FIG. 12 shows the proliferation of TF-1 cells treated with 107A in the presence of GM-CSF, IL-3, or IL-5.
Figure 13:
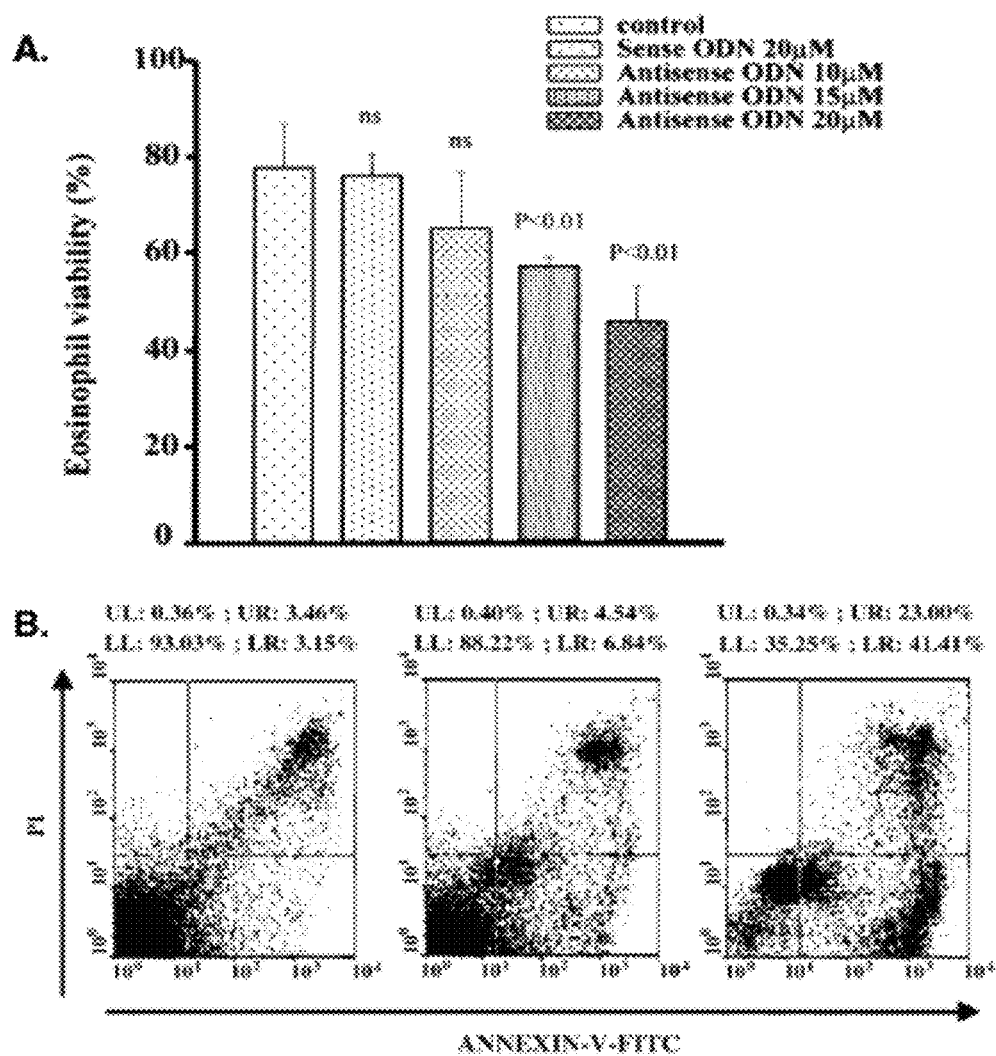
FIG. 13A shows the modulation of eosinophil survival by 107A, assessed using Trypan blue dye exclusion assay.
FIG. 13B shows the modulation of eosinophil survival by 107A as assessed by flow cytometric analysis using the Annexin-V-FITC and propidium iodide protocol.

Referring to FIG. 12, proliferation of TF-1 cells treated with 107A antisense in the presence of GM-CSF, IL-3 or IL-5 is shown. Cells were incubated with 107A (10 microM) for 5 hours in serum-free medium, containing 1 ng/mL GM-CSF or 3 ng/mL IL-3 or 3 ng/mL IL-5. The incubation was terminated after 2 days, and cell proliferation was measured by alamar blue assay (n=3). The results are expressed as the mean of absorbance (570-595)±SD.

TF-1 cells require the cytokines GM-CSF, IL-3, or IL-5 to proliferate, and the biologic response to these cytokines involves the beta-chain signalling pathway. Inhibition of cell surface expression of beta-chain protein was expected to inhibit the proliferation of TF-1 cells, even in the presence of these cytokines. 107A (10 microM) caused growth inhibition of TF-1 cells in the presence of IL-3, IL-5, or GM-CSF. These results demonstrate that inhibition of beta-chain cell surface protein expression by 107A effectively inhibited cellular biologic responses to all three cytokines.

Eosinophils express GM-CSF, IL-3 and IL-5 receptors and play a key role in inflammation and allergy. Eosinophils require GM-CSF, IL-3, and particularly IL-5 for their differentiation, activation, and survival (Oddera et al., 1998, Lung. 176: 237-247; Ohnishi et al., 1993, J. Allergy Clin. Immunol., 92: 607-615). The ability of antisense oligonucleotide targeting beta-chain mRNA to inhibit eosinophil survival in response to IL-5 was investigated. Referring to FIGS. 13A and 13B, modulation of eosinophil survival by 107A is shown.

Referring to FIG. 13A, purified human eosinophils were incubated with 107A at the indicated concentrations (10, 15, and 20 microM) in RPMI medium supplemented with 5% FBS and 1.5 ng/mL IL-5 overnight. Eosinophil viability was assessed using Trypan blue dye exclusion assay. The results are the mean results of three experiments. Treatment with 107A at the indicated concentrations significantly reduced eosinophil survival in a dose-dependent manner, to 35%±12% (10 microM), 43%±2% (15 microM), and 54%±7% (20 microM) of control levels (p<0.01). Eosinophil survival was not significantly affected by treatment with sense oligonucleotide, as a control, at a concentration of 20 microM. Thus, 107A targeting the beta-chain inhibited eosinophil survival even in the presence of culture medium containing the specific cytokine IL-5.

Referring to FIG. 13B, purified human eosinophils were incubated for 48 hours in RPMI supplemented with 5% FBS and 2 ng/mL IL-5 in the presence or absence of 107A (15 microM). Eosinophil viability was assessed by flow cytometric analysis using the Annexin-V-FITC and propidium iodide protocol as described in material and methods. When eosinophils were treated with 107A, their viability was decreased by 64%, 41% due to apoptosis. In contrast, in non-treated cells and cells treated with sense oligonucleotide, the percentage of dead cells was lower.

Thus, 107A antisense specifically inhibits the expression of the common beta-chain in TF-1 cell and primary eosinophils at the level of mRNA and protein as measured by RT-PCR and FACS. The maximum efficacy obtained on the cell system tested, under the experimental conditions used, was observed at a concentration of 20 microM. In the presence of 107A, the proliferation of TF-1 cells was reduced, whether IL-3, IL-5, or GM-CSF was used as a trophic factor. This result shows the specificity and the efficacy of 107A antisense for the beta-chain.

Eosinophil survival was inhibited by 107A in the presence of IL-5 and it appeared that apoptosis is a consequence of this inhibitory effect. Eosinophils play a key role in allergic inflammation and require GM-CSF, IL-3, and IL-5 for their differentiation, activation, and survival (Adachi et al., 1995, Am. J. Respir. Crit. Care Med. 151: 618-623 and Oddera et al., 1998, Lung. 176: 237-247). In asthma, eosinophil accumulation and survival are thought to be important contributors to inflammation and epithelial tissue damage because they release toxic products, including eosinophil cationic protein (Walsh et al., 1997, Clin. Exp. Allergy 27: 482-487).

Example 5 mRNA Analysis for ASM8 Target Genes in Trachea Samples

Further experiments were conducted to analyze trachea samples in Cynomolgus Monkeys for the levels of mRNA for the target genes to which ASM8 is directed against (beta-chain-subunit and CCR3). On Day 15 (one day after the last dose), trachea samples were collected immediately following sacrifice of all Main Phase animals in Groups 1 (control) and 4 (high-dose group; target dose level of 2.5 mg/kg/day) and quickly frozen in liquid nitrogen. The frozen trachea samples were analyzed for target mRNA levels by RT-PCR.

Target gene expression levels ($\beta_c$-subunit and CCR3) were determined for the monkey trachea samples using a validated, semi-quantitative RT-PCR method. $\beta_c$-Subunit and CCR3-specific PCR amplifications were carried out on trachea extracts for control and high-dose ASM8-treated animals (Table 7).

TABLE 7

RT-PCR Sample Analysis Results

| Animal | Sex | $\beta_c$-subunit | CCR3 | IL-4 | TNF-$\alpha$ |
|---|---|---|---|---|---|
| Dose = 0 mg/kg bw/day | | | | | |
| 1002A | M | 21787 | 28776.5 | 15312.6 | 91432.5 |
| 1003A | M | 25339 | 19986.9 | 11093.0 | 99032.7 |
| 1004C | M | 27568 | 27600.6 | 13218.8 | 77107.2 |
| 1101A | M | 21599 | 22619.4 | 12450.4 | 95441.5 |
| 1501A | F | 5452 | 5053.0 | 18074.5 | 80778.5 |
| 1502A | F | 14920 | 19799.4 | 15252.2 | 86741.0 |
| 1503B | F | 9691 | 15004.8 | 15200.0 | 90229.0 |
| 1504C | F | 22800 | 52842.7 | 9001.6 | 102726.5 |
| Mean | | 20529 | 26661 | 13700 | 90436 |
| Dose = 5 mg/kg bw/day | | | | | |
| 4002B | M | 22073 | 22778.3 | 11034.0 | 71911.0 |
| 4003B | M | 12652 | 9109.4 | 5587.0 | 86317.4 |
| 4101A | M | 21154 | 11365.8 | 15361.0 | 86526.0 |
| 4501A | F | 14755 | 2227.0 | 173.5 | 57996.7 |
| 4502B | F | 7604 | 21286.0 | 14463.4 | 98144.3 |
| 4503B | F | 3505 | 29105.0 | 16711.0 | 103532.5 |
| Mean | | 13624 | 18729 | 12691 | 84071 |

Note: shaded values represent outliers that were not included in calculation of mean values.

Although glyceraldehyde-3-phosphate dehydrogenase (G3PDH) is typically used as an internal control in the analyses of RT-PCR reactions, a mild cellular infiltrate of the lungs and trachea was observed (as is typically observed with other antisense oligonucleotides at deposition sites). Thus, as the cellular infiltrate contributed to the measured levels of $\beta_c$-subunit and CCR3 (i.e., immune cells express $\beta_c$-subunit and CCR3), G3PDH was not considered to be the most appropriate gene to use as the internal control in this case. Instead, the expression of the target genes was normalized to the mRNA levels for inflammatory cytokines; i.e., IL-4 and TNF-$\alpha$. The results demonstrate that even approximately 24 hours after administration of ASM8, the relative expression of the $\beta_c$-subunit and CCR3 mRNA to IL-4 mRNA was decreased by 29% and 24%, respectively, and the expression relative to TNF-$\alpha$ was decreased by 30% and 24%, respectively, in ASM8-treated animals (Table 8).

TABLE 8

Inhibition Table

| | Ratio | | | |
|---|---|---|---|---|
| | $\beta_c$-subunit/IL-4 | CCR3/IL-4 | $\beta_c$-subunit/TNF$\alpha$ | CCR3/TNF$\alpha$ |
| Control | 1.50 | 1.95 | 0.23 | 0.29 |
| Treated | 1.07 | 1.48 | 0.16 | 0.22 |
| Inhibition | 28.7% | 24.1% | 30.4% | 24.1% |

ASM8 treatment thus significantly inhibits the $\beta_c$-subunit and the CCR3 mRNA expression relative to the inflammatory cytokines IL-4 and TNF-alpha, despite the complexity of monkey tracheal tissue and the 24 hours that elapsed between ASM8 dosing and obtaining the tissue samples.

Example 6

Storage Stability of ASM8

Stability testing was conducted to evaluate the integrity of the oligonucleotide constituents of ASM8 (TOP004 and TOP005) under different storage temperatures. This information is important to define the optimal storage, retest, and shelf life conditions for ASM8.

Figure 15:
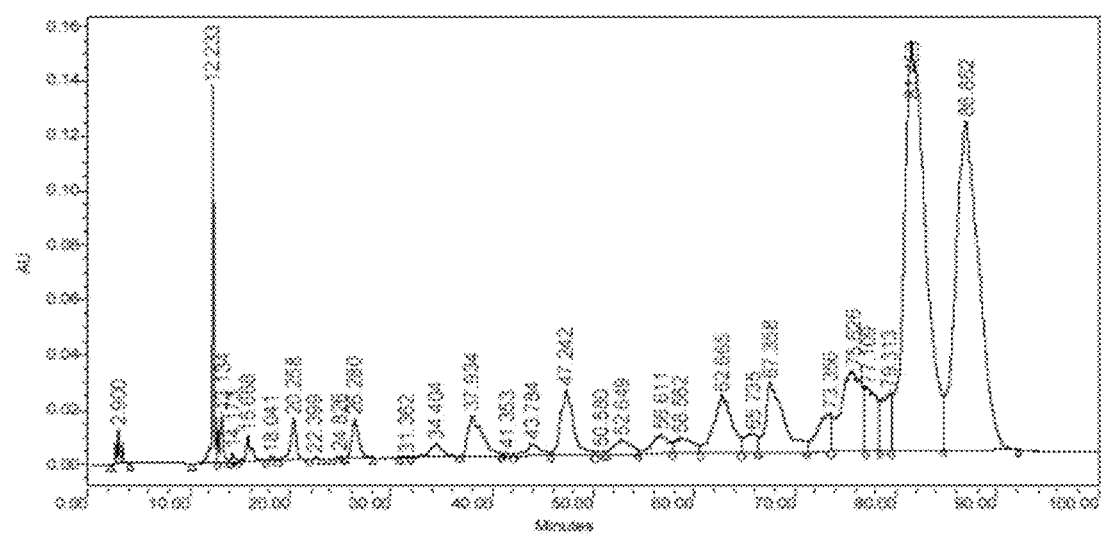
FIG. 15 shows the elution profile for ASM8 after treatment with CH$_3$COOH for 3 hours and submitted to alkaline lysis prior to fractionation by DEAE anion exchange chromatography.
Figure 16:
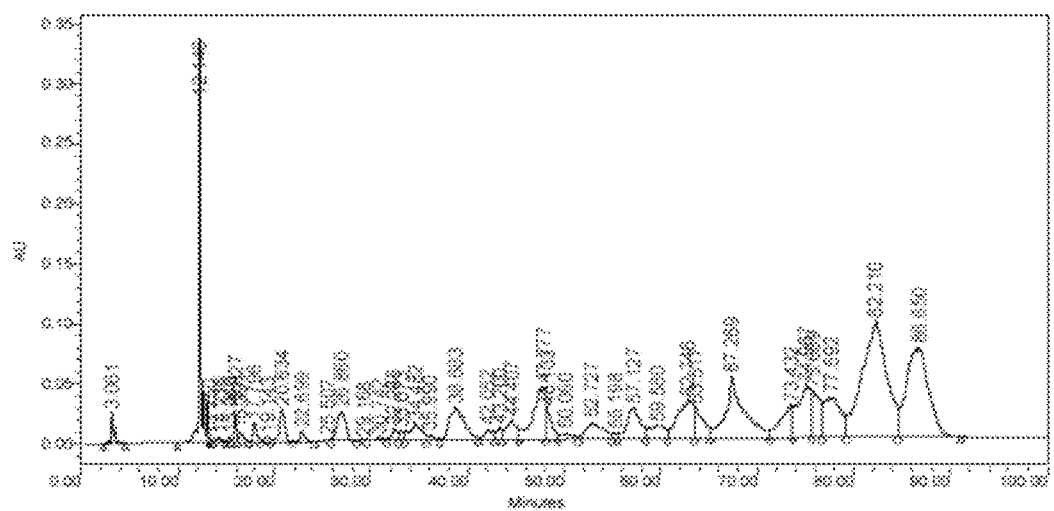
FIG. 16 shows the elution profile for ASM8 after treatment with CH$_3$COOH for 6 hours and submitted to alkaline lysis prior to fractionation by DEAE anion exchange chromatography.

Capillary gel electrophoresis (CGE) and high performance (pressure) liquid chromatography (HPLC) have been widely used for the chemical analysis of antisense oligonucleotides. As ASM8 consists of two oligonucleotides, the test system must provide adequate separation of the two individual antisense molecules. Thus, the following will be described: 1) a method based on anion exchange chromatography to separate ASM8 components (TOP 004 and TOP 005) and their degradation products, and 2) the effect of storage temperature on the stability of ASM8 constituents (FIGS. 14-16).

ASM8 was weighed and solubilized in PBS at a concentration of 0.5 mg/mL (0.25 mg/mL TOP004 and 0.25 mg/mL TOP 005). [The purity factor for TOP 004, was 1.15 (i.e., 1.15 g of powder contains 1 g of active molecule); the purity factor for TOP 005, was 1.24 (i.e., 1.24 g of powder contains 1 g of active molecule).]

To induce degradation of TOP004 and TOP005 prior to analysis (in order to ensure resolution of degradation products from the intact molecules), the following treatments were performed:

Depurination: ASM8 was resuspended in 30% CH$_3$COOH at a final concentration of 0.5 mg/mL, and incubated for 3, 4, or 6 hours at room temperature. The reaction was stopped by addition of 5 volumes of water and the mixture placed at −20° prior to lyophilization in a Speed-Vac to remove acetic acid.

Cleavage: the depurinated oligonucleotides were resuspended in 0.2 M NaOH (0.5 mg/mL), incubated at 50° C. for 1 hour, and stored at −20° C. or analyzed by HPLC.

Aliquots of ASM8 (0.5 mg/mL) in PBS were incubated at −20° C., 4° C., 30° C., and 40° C. for 2 months. At weeks 4, and 8, the HPLC profile of ASM8 was established. The control condition was defined as the HPLC profile of ASM8 prior to any storage time (i.e., at time zero). The HPLC system was driven by Breeze (V 3.30) software from Waters (FIGS. 17A1, 17A2, 17B1 and 17B2).

HPLC separation was performed with a Waters 1500 Series Binary HPLC pump coupled to a Waters 2487 Dual λ Absorbance detector and equipped with in-line degasser, oven, and 1500 series manual injector, Reodyne 7725i.

The mixture of oligonucleotides was fractionated on a Waters Protein Pak DEAE 5PW anion exchange column (0.5 cm×7.5 cm), maintained at 60° C., and detected by UV absorption at 260 nm. The oligonucleotide mixture (volume=25 microL) was loaded onto the column in water (buffer A) and the elution was performed by progressively increasing the proportion of buffer B (1 M $LiClO_4$), resulting in an increase of ionic strength of the liquid phase (Table 9), which eluted the oligonucleotide from the solid phase (column).

Under the assay conditions, 62.5 micrograms of either TOP004 or TOP005 produced a measurable change >0.15 absorbance unit (AU) at 260 nm.

TABLE 9

HPLC Gradient for Separation of ASM8 and Degradants

| Time (min) | Flow (mL/min) | Buffer A (%) | Buffer B (%) |
|---|---|---|---|
| 0 | 1 | 100 | 0 |
| 5 | 1 | 100 | 0 |
| 10 | 1 | 93 | 7 |
| 100 | 1 | 65 | 35 |
| 102 | 1 | 20 | 80 |
| 122 | 1 | 20 | 80 |
| 124 | 1 | 100 | 0 |
| 144 | 1 | 100 | 0 |
| 146 | 0.1 | 100 | 0 |

The chromatogram in FIG. 14 shows the elution profile of the individual products of ASM8 (TOP 004 and TOP 005) under DEAE anion exchange chromatography. A volume of 25 microL of freshly prepared ASM8 (0.5 mg/mL) was fractionated on the DEAE anion exchange column. Under the gradient conditions described above, TOP004 eluted earlier than TOP 005; this is consistent with TOP004 being 2 nucleotides shorter than TOP005 and having fewer negatively charged residues. The TOP004 oligonucleotide eluted at 81.3 minutes and represented 48.0% of the total material absorbing at 260 nm. TOP005 eluted at 86.8 minutes and represented 49.3% of the total material absorbing at 260 nm.

In order to confirm adequate separation between TOP004, TOP005, and the degradation products of ASM8, a two-step chemical degradation of ASM8 was performed. The cleavage step was kept constant but the incubation period for the depurination step was performed for 3 to 6 hours. Referring to FIG. 15, ASM8 (0.5 mg/mL) was treated with $CH_3COOH$ for 3 hours and submitted to alkaline lysis (as described above) prior to fractionation by DEAE anion exchange chromatography. The TOP004 oligonucleotide eluted at 81.5 minutes and represented 32.4% of the total material absorbing at 260 nm. The TOP005 product eluted at 86.9 minutes and represented 28.0% of the total material. The minor peaks represent degradation products of ASM8. Referring to FIG. 16, ASM8 (0.5 mg/mL) was treated with $CH_3COOH$ for 6 hours and submitted to alkaline lysis as described in above prior to fractionation by DEAE anion exchange chromatography. Under detection at 260 nm, the TOP004 oligonucleotide eluted at 82.2 minutes and TOP005 eluted at 86.7 minutes. By increasing the depurination time, the proportion of TOP004 decreased to 20.6% and TOP005 to 14.5%. The extent of degradation of TOP005 appeared to be slightly greater under these experimental conditions. As seen on the chromatograms in FIGS. 15 and 16, increasing the depurination time increased the degradation of ASM8.

Referring to FIGS. 17A1, 17A2, 17B1 and 17B2, the chemical stability of ASM8 under different storage temperatures was evaluated. ASM8 (0.5 mg/mL in PBS) was incubated at −20° C., 4° C., 30° C., or 40° C. for 4 weeks (FIGS. 17A1 and 17A2) and 8 weeks (FIGS. 17B1 and 17B2) and analyzed by DEAE anion exchange chromatography. The various storage temperatures tested in this experiment did not affect the elution profile of the ASM8 components. No significant degradation of ASM8 was observed at any of the temperatures at which ASM8 was stored for up to 2 months.

A separation method based on DEAE anion exchange HPLC for ASM8 has been described above. Because of the nature of this product, adequate separation of the components of ASM8 (TOP004 and TOP005 oligonucleotides) is preferred. Under the gradient conditions described, the retention time of TOP004 was more than 5 minutes earlier than the retention time of TOP 005, with very little overlap of the two peaks.

The method is also capable of detecting degradation products of ASM8. The chemical stability of ASM8 under different temperature, humidity, and light conditions can be assessed by this HPLC method.

The formulation of ASM8 in PBS was chemically stable, and no significant degradation products were detected by the HPLC procedure after storage under a range of temperatures for up to 2 months.

Example 7

Thermodynamic Evaluation of ASM8

Further experiments were conducted to ensure that the two oligonucleotide strands, TOP004 and TOP005, did not interact in solution using thermodynamic evaluations.

TOP004 and TOP005 were mixed at equimolar concentrations in 1×PBS (as well as in other buffer systems). Total oligonucleotide concentration ranged from approximately 1.2 to 8.7 microM. Standard UV thermo-denaturation methods were conducted using a Beckman DU640 spectrophotometer with a Tm accessory. Change in absorbance was detected at 260 nm at each degree from 10 to 90° C. Melting curves were fitted using MELTWIN 3.5™ software to determine thermodynamic parameters. Screen pictures of melting curves and thermodynamics summary tables were produced.

Referring to FIG. 18, melting curves for TOP004 and TOP005 in 1×PBS are shown. FIG. 19 is a thermodynamics summary based on results of melting curve fits for TOP004 and TOP005 in 1×PBS. The results demonstrated that none of the oligonucleotide combinations/conditions produced a significant transition (jump in absorbance) in melting profile upon increase in temperature. This indicated that tested oligonucleotide mixtures do not form significant secondary structure interactions at tested buffer conditions.

Example 8

ASM8 Toxicity in Cynomolgus Monkey

This example shows the toxicity of ASM8, consisting of a 1:1 mixture of TOP004 and TOP005. Also shown is the toxicokinetic profile of its individual oligonucleotide components, when administered by inhalation exposure once daily for 14 consecutive days to cynomolgus monkeys. Further, 14 days of inhalation exposure to ASM8 did not elicit a systemic hypersensitivity condition detectable by intradermal injection (ID).

TABLE 10

Estimated Achieved dosage

| Dose Group/Treatment | Estimated Achieved Dosage (mg/kg/day) | | |
|---|---|---|---|
| | Males | Females | Combined |
| 1: Vehicle control | 0 | 0 | 0 |
| 2: ASM8 Low Dose | 0.05 | 0.05 | 0.05 |
| 3: ASM8 Mid Dose | 0.22 | 0.23 | 0.22 |
| 4: ASM8 High Dose | 2.4 | 2.5 | 2.5 |

TABLE 11

Overall exposure aerosol concentrations

| Dose Group/Treatment | Mean (microg/L) | S.D. (microg/L) | C.V. (%) |
|---|---|---|---|
| 1: Vehicle control | 0 | — | — |
| 2: ASM8 Low Dose | 7.4 | 0.89 | 12.1 |
| 3: ASM8 Mid Dose | 34.6 | 5.68 | 16.4 |
| 4: ASM8 High Dose | 380.4 | 68.43 | 18.0 |

Comprehensive assessments of mortality, clinical signs, body weights, food consumption, electrocardiography, ophtalmoscopy and clinical pathology were performed. Serial blood samples were obtained on the first and last days of exposure and the end of the recovery period and tissues were collected at termination, for determination of individual oligonucleotide content. Additionally, on Day 25, animals designated for the recovery phase were given an intradermal injection (ID) of ASM8 to assess potential systemic hypersensitivity. All animals were euthanized following 14 days of exposure (Day 15) or following a 14-day recovery period (Day 29) and subjected to a full necropsy with collection of a complete set of tissues from each animal. Histopathologic evaluation consisted of microscopic examination of all tissues from animals in the high-dose and control groups, and respiratory tract tissues in the lower dose groups and recovery animals.

The formulation of ASM8 aerosolized readily and produced exposure aerosols that were consistently stable and respirable, with inter-group mass median diameter (MMAD) and geometric standard deviation (GSD) values between 1.7-1.8 micrometer and 2.12-2.22, respectively. The resultant estimated achieved doses were close to target at 0.05, 0.22 and 2.5 mg/kg/day for groups 2-4, respectively, Table 7-8.

There were no deaths, and the monkeys tolerated the dosages well. There were no effects on body weight, food consumption, electrocardiography, ophtalmoscopy or clinical pathology parameters and hypersensitivity testing revealed no effect of ASM8 administration. Following necropsy, organ weight measurements produced no evidence of toxicity. Macroscopic investigations of all organs revealed only pale discoloration to the kidneys in ASM8 treated animals. However, due to the absence of corroboratory microscopic alterations, clinical pathology findings or organ weight changes, and the fact that the discoloration was not seen following 14 days of recovery, this finding was considered of equivocal biological and toxicological significance.

Plasma levels of TOP004 and TOP005, as well as their proximal (n−1) metabolites, were very low in plasma, with low- and mid dose groups below the limit of quantification. For the high dose group (2.5 mg/kg/day), TOP004 and TOP005 concentrations were typically greatest at either the earliest sampling time of 0.5 hours postdose, or at the 1-hour timepoint. At most postdosing timepoints, the mean concentration of TOP004 was similar to that of TOP005, FIG. 20A and FIG. 20B.

There was no accumulation of either oligonucleotide component (or their n−1 metabolites) in the plasma with repeated daily administration for 14 days as shown in FIG. 21A and FIG. 21B There were no consistent gender differences in the plasma concentrations. A significant percentage of circulating oligonucleotide was present as the proximal n−1 metabolite for both TOP004 and TOP005, although the percentage tended to be slightly lower for TOP004. For both oligonucleotides and their n−1 metabolites, clearance from the blood compartment (plasma) was evident over the 24-hours collection period. At the terminal sacrifice (one day after the last inhalation of dose of ASM8), appreciable quantities of the intact oligonucleotide components of ASM8 (TOP004 and TOP005) were detected in the trachea of the high-dose animals. At the end of the 14-day recovery period (Day 29), the levels of TOP004 and its n−1 metabolite had diminished, relative to Day 15 and were measured slightly above the limit of detection of the assay. In contrast, no TOP005 or its metabolite were quantifiable at the recovery sacrifice timepoint. These results suggest that TOP004 has greater tissue stability than TOP005.

Treatment related microscopic changes were not observed in any organ except the respiratory tract. All the observed changes in the respiratory tract were graded on a 4 point scale as being the lowest (minimal). The changes that were noted were for the lungs included: foamy alveolar macrophages in animals dosed at 0.22 or 2.5 mg/kg/day, intra-alveolar granulocytic inflammation at 2.5 mg/kg/day, focal hemorrhage in two animals and focal bronchiolar metaplasia in one animal dosed at 2.5 mg/kg/day; for the nasal cavity: focal erosion of the squamous epithelium of the nasal septum in 2/6 animals dosed at 2.5 mg/kg/day, accompanied by acute inflammation and an inflammatory exudate in one monkey; and for the bronchial lymph nodes: foamy macrophages in animals dosed at 2.5 mg/kg/day. The severity of the changes observed in the lungs of mid- and high-dose animals were minor and not accompanied by evidence of local damage or cellular infiltration in the lung parenchyma. Inflammatory cells were sparse and only seen in a small number of ASM8 high-dose animals and the distribution of the changes was consistent with inhalation of the test material. Focal hemorrhages were very small and interpreted as likely to be fortuitous. The changes reported are thus generally consistent with normal pulmonary mechanisms associated with phagocytosis and clearance of an inhaled test material. Withdrawal of treatment for 14 days resulted in the continued presence of a few foamy alveolar macrophages with no inflammation in one of the two ASM high-dose animals. This observation is consistent with gradual regression of the lesions and indicates that there was no progressive or persistent alteration to the lung parenchyma.

There was no evidence of an effect of treatment on nasal tissues following the 14-day recovery period. Regarding the bronchial lymph node findings in high-dose animals, foamy macrophages in the medullary sinuses are consistent with clearance of the test material by lymphatic drainage from the lung. There was no evidence of parenchymal damage, and the lymph nodes did not appear to be in a reactive condition.

In conclusion, inhalation of ASM8 for 14 consecutive days at estimated achieved doses of up to 2.5 mg/kg/day was well tolerated and produced no effects on body weights, food consumption, electrocardiography, organ weights, ophtalmoscopy or clinical pathology parameters, and hypersensitivity testing revealed no effect of ASM8 administration. A number of mostly minimal histomorphologic alterations were noted in the lungs (0.22 and 2.5 mg/kg/day), as well as in the nasal cavity and bronchial lymph nodes (2.5 mg/kg/day). These changes were reduced in severity or absent following 14 days of recovery.

Although preferred embodiments of the invention have been described herein, it will be understood by those skilled in the art that variations may be made thereto without departing from the spirit of the invention or the scope of the appended claims.

The invention claimed is:

1. A pharmaceutical composition comprising two oligonucleotides consisting of SEQ ID NO. 13 and SEQ ID NO. 14 and a pharmaceutically acceptable carrier.

2. The pharmaceutical composition of claim 1, wherein the pharmaceutical composition is topical.

3. A method for treating asthma in a subject, comprising the step of administering to the subject an effective amount of the pharmaceutical comprising two oligonucleotides consisting of SEQ ID NO. 13 and SEQ ID NO. 14.

4. The method of claim 3, wherein the method is for treating asthma.

* * * * *

SEQUENCE LISTING

```
<160> NUMBER OF SEQ ID NOS: 63

<210> SEQ ID NO 1
<211> LENGTH: 21
<212> TYPE: DNA
<213> ORGANISM: Homo sapiens

<400> SEQUENCE: 1
gttactactt ccacctgcct g                                              21

<210> SEQ ID NO 2
<211> LENGTH: 21
<212> TYPE: DNA
<213> ORGANISM: Homo sapiens

<400> SEQUENCE: 2
tggaaaagcg acacctacct g                                              21

<210> SEQ ID NO 3
<211> LENGTH: 22
<212> TYPE: DNA
<213> ORGANISM: Homo sapiens

<400> SEQUENCE: 3 ccctttcct ggaaaagcga ca                                              22

<210> SEQ ID NO 4
<211> LENGTH: 21
<212> TYPE: DNA
<213> ORGANISM: Homo sapiens

<400> SEQUENCE: 4
ctcccttttc ctggaaaagc g                                              21

<210> SEQ ID NO 5
<211> LENGTH: 20
<212> TYPE: DNA
<213> ORGANISM: Homo sapiens

<400> SEQUENCE: 5
tccacctccc ttttcctgga                                                20

<210> SEQ ID NO 6
<211> LENGTH: 21
<212> TYPE: DNA
<213> ORGANISM: Homo sapiens

<400> SEQUENCE: 6
cctccttgtt ccacctccct t                                              21

<210> SEQ ID NO 7
<211> LENGTH: 21
<212> TYPE: DNA
<213> ORGANISM: Homo sapiens

<400> SEQUENCE: 7
acccattggc attgctcatt t                                              21
```

```
<210> SEQ ID NO 8
<211> LENGTH: 21
<212> TYPE: DNA
<213> ORGANISM: Homo sapiens

<400> SEQUENCE: 8
tccttgcaat tagtgctgct t                                              21

<210> SEQ ID NO 9
<211> LENGTH: 21
<212> TYPE: DNA
<213> ORGANISM: Homo sapiens

<400> SEQUENCE: 9
tcgtgcagtt cttcttttc a                                               21

<210> SEQ ID NO 10
<211> LENGTH: 21
<212> TYPE: DNA
<213> ORGANISM: Homo sapiens

<400> SEQUENCE: 10
cagactagct tctcagtttt g                                              21

<210> SEQ ID NO 11
<211> LENGTH: 21
<212> TYPE: DNA
<213> ORGANISM: Homo sapiens

<400> SEQUENCE: 11
tgctaattta gtgaagtcct t                                              21

<210> SEQ ID NO 12
<211> LENGTH: 22
<212> TYPE: DNA
<213> ORGANISM: Homo sapiens

<400> SEQUENCE: 12
cttctccctg aaaatctctt ct                                             22

<210> SEQ ID NO 13
<211> LENGTH: 19
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is 2,6-diaminopurine-2'-deoxyriboside
<220> FEATURE:
<221> NAME/KEY: misc_feature
<222> LOCATION: (15)..(15)
<223> OTHER INFORMATION: n is 2,6-diaminopurine-2'-deoxyriboside

<400> SEQUENCE: 13
gggtctgcng cgggntggt                                                 19

<210> SEQ ID NO 14
<211> LENGTH: 21
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n is 2,6-diaminopurine-2'-deoxyriboside
<220> FEATURE:
<221> NAME/KEY: misc_feature
```

```
<222> LOCATION: (7)..(7)
<223> OTHER INFORMATION: n is 2,6-diaminopurine-2'-deoxyriboside
<220> FEATURE:
<221> NAME/KEY: misc_feature
<222> LOCATION: (13)..(13)
<223> OTHER INFORMATION: n is 2,6-diaminopurine-2'-deoxyriboside

<400> SEQUENCE: 14
gttnctnctt cncctgcct g                                          21

<210> SEQ ID NO 15
<211> LENGTH: 17
<212> TYPE: DNA
<213> ORGANISM: Artificial sequence
<220> FEATURE:
<223> OTHER INFORMATION: Primer

<400> SEQUENCE: 15
atggtgctgg cccaggg                                              17

<210> SEQ ID NO 16
<211> LENGTH: 18
<212> TYPE: DNA
<213> ORGANISM: Artificial sequence
<220> FEATURE:
<223> OTHER INFORMATION: Primer

<400> SEQUENCE: 16
ccagggagat ggtgctgg                                             18

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
ccgcttgtag accacctcaa c                                         21

<210> SEQ ID NO 18
<211> LENGTH: 22
<212> TYPE: DNA
<213> ORGANISM: Artificial sequence
<220> FEATURE:
<223> OTHER INFORMATION: Primer

<400> SEQUENCE: 18
ccttggctga acagagacga tg                                        22

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
tgctctgtga aaagccgat g                                          21

<210> SEQ ID NO 20
<211> LENGTH: 21
<212> TYPE: DNA
<213> ORGANISM: Artificial sequence
<220> FEATURE:
<223> OTHER INFORMATION: Primer

<400> SEQUENCE: 20
```

```
accaaaagtg acagtcctgg c                                              21
```

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21

```
aagtcagggt ttgagggcta tg                                             22
```

<210> SEQ ID NO 22
<211> LENGTH: 21
<212> TYPE: DNA
<213> ORGANISM: Artificial sequence
<220> FEATURE:
<223> OTHER INFORMATION: Primer

<400> SEQUENCE: 22

```
caaggggggca gagacaggta g                                             21
```

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23

```
accacagtcc atgccatcac                                                20
```

<210> SEQ ID NO 24
<211> LENGTH: 21
<212> TYPE: DNA
<213> ORGANISM: Artificial sequence
<220> FEATURE:
<223> OTHER INFORMATION: Primer

<400> SEQUENCE: 24

```
tccaccaccc ctgttgctgt a                                              21
```

<210> SEQ ID NO 25
<211> LENGTH: 150
<212> TYPE: DNA
<213> ORGANISM: Macaca fascicularis
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (142)..(143)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 25

```
ggcagaagaa accatcccgc tgcrgaccct acgctgctac aatgactaca ccagccacat    60
cacctgcagg tggcggaca  cccaggatgc ccagcggctt gtcaacgtga ccctcagtcg   120
ccgggtgaat gangaccctc cnnagcnagt                                    150
```

<210> SEQ ID NO 26
<211> LENGTH: 150

```
<212> TYPE: DNA
<213> ORGANISM: Macaca fascicularis
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 26
ggcagaagaa accatcccgc tgcrgaccct acgctgctac aatgactaca ccagccacat      60
cacctgcagg tgggcggaca cccaggatgc ccagcggctt gtcaacgtga ccctcagtcg     120
ccgggtgaat gangaccctc cncagcnagt                                      150

<210> SEQ ID NO 27
<211> LENGTH: 150
<212> TYPE: DNA
<213> ORGANISM: Macaca fascicularis
<220> FEATURE:
<221> NAME/KEY: misc_feature
<222> LOCATION: (142)..(143)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 27
ggcagaagaa accatcccgc tgcrgaccct acgctgctac aatgactaca ccagccacat      60
cacctgcagg tgggcggaca cccaggatgc ccagcggctt gtcaacgtga ccctcagtcg     120
ccgggtgaat gaggaccctc cnnagcnagt                                      150

<210> SEQ ID NO 28
<211> LENGTH: 150
<212> TYPE: DNA
<213> ORGANISM: Homo sapiens

<400> SEQUENCE: 28
ggcagaagaa accatcccgc tgcagaccct gcgctgctac aacgactaca ccagccacat      60
cacctgcagg tgggcagaca cccaggatgc ccagcggctc gtcaacgtga ccctcattcg     120
ccgggtgaat gaggacctcc tggagccagt                                      150

<210> SEQ ID NO 29
<211> LENGTH: 19
<212> TYPE: DNA
<213> ORGANISM: Homo sapiens

<400> SEQUENCE: 29
ctgggccatc agtgctctg                                                   19

<210> SEQ ID NO 30
<211> LENGTH: 18
<212> TYPE: DNA
<213> ORGANISM: Homo sapiens

<400> SEQUENCE: 30
cagagcactg atggccca                                                    18
```

```
<210> SEQ ID NO 31
<211> LENGTH: 19
<212> TYPE: DNA
<213> ORGANISM: Homo sapiens

<400> SEQUENCE: 31
cgtggcactc agtgtcctg                                                  19

<210> SEQ ID NO 32
<211> LENGTH: 21
<212> TYPE: DNA
<213> ORGANISM: Homo sapiens

<400> SEQUENCE: 32
cctttgacct gccaatgctc t                                               21

<210> SEQ ID NO 33
<211> LENGTH: 132
<212> TYPE: DNA
<213> ORGANISM: Pan troglodytes

<400> SEQUENCE: 33
cttgtcagaa accatcccgc tgcagaccct gcgctgctac aacgactaca ccagccacat     60
cacctgcagg tgggcagaca cccaggatgc ccagcggctc gtcaacgtga ccctcattcg    120
ccgggtgaat ga                                                        132

<210> SEQ ID NO 34
<211> LENGTH: 132
<212> TYPE: DNA
<213> ORGANISM: Cavia porcellus

<400> SEQUENCE: 34
ctcagaggac accgtcccgc tgcagaccct gcgctgctac aatgactaca ccagccgcat     60
cgtgtgcagc tgggcggcgg aggcggccgc tgagcagctc atcaatgtga ccctccatcg    120
ccatcgcagg tt                                                        132

<210> SEQ ID NO 35
<211> LENGTH: 132
<212> TYPE: DNA
<213> ORGANISM: Rattus norvegicus

<400> SEQUENCE: 35
ggcagaagaa actgtccctc tgaagactct gcagtgctac aacgactata tcgagcgcat     60
catctgcagc tgggccgaca cggaggacgc ccaggggctc gttaacctga ccctctatca    120
ctggctagac aa                                                        132

<210> SEQ ID NO 36
<211> LENGTH: 132
<212> TYPE: DNA
<213> ORGANISM: Mus musculus

<400> SEQUENCE: 36
ggcagaagaa acggtccctc tgaagactct gcagtgctac aatgactaca ccaaccacat     60
catctgcagc tgggcggaca cagaggatgc ccaggggcta atcaacatga ccctctatca    120
ccagctagag aa                                                        132

<210> SEQ ID NO 37
<211> LENGTH: 12
<212> TYPE: PRT
<213> ORGANISM: Macaca fascicularis
```

```
<220> FEATURE:
<221> NAME/KEY: misc_feature
<222> LOCATION: (8)..(8)
<223> OTHER INFORMATION: Xaa is Gln or Arg

<400> SEQUENCE: 37

Ala Glu Glu Thr Ile Pro Leu Xaa Thr Leu Arg Cys
1               5                   10

<210> SEQ ID NO 38
<211> LENGTH: 12
<212> TYPE: PRT
<213> ORGANISM: Homo sapiens

<400> SEQUENCE: 38

Ala Glu Glu Thr Ile Pro Leu Gln Thr Leu Arg Cys
1               5                   10

<210> SEQ ID NO 39
<211> LENGTH: 12
<212> TYPE: PRT
<213> ORGANISM: Pan troglodytes

<400> SEQUENCE: 39

Leu Ser Glu Thr Ile Pro Leu Gln Thr Leu Arg Cys
1               5                   10

<210> SEQ ID NO 40
<211> LENGTH: 12
<212> TYPE: PRT
<213> ORGANISM: Cavia porcellus

<400> SEQUENCE: 40

Ser Glu Asp Thr Val Pro Leu Gln Thr Leu Arg Cys
1               5                   10

<210> SEQ ID NO 41
<211> LENGTH: 12
<212> TYPE: PRT
<213> ORGANISM: Mus musculus

<400> SEQUENCE: 41

Ala Glu Glu Thr Val Pro Leu Lys Thr Leu Gln Cys
1               5                   10

<210> SEQ ID NO 42
<211> LENGTH: 12
<212> TYPE: PRT
<213> ORGANISM: Rattus norvegicus

<400> SEQUENCE: 42

Ala Glu Glu Thr Val Pro Leu Lys Thr Leu Gln Cys
1               5                   10

<210> SEQ ID NO 43
<211> LENGTH: 19
<212> TYPE: DNA
<213> ORGANISM: Homo sapiens

<400> SEQUENCE: 43
gggtctgcag cgggatggt                                             19

<210> SEQ ID NO 44
<211> LENGTH: 38
<212> TYPE: DNA
<213> ORGANISM: Homo sapiens
```

```
<400> SEQUENCE: 44
ggcagaagaa accatcccgc tgcagaccct gcgctgct                              38

<210> SEQ ID NO 45
<211> LENGTH: 38
<212> TYPE: DNA
<213> ORGANISM: Pan troglodytes

<400> SEQUENCE: 45
cttgtcagaa accatcccgc tgcagaccct gcgctgct                              38

<210> SEQ ID NO 46
<211> LENGTH: 38
<212> TYPE: DNA
<213> ORGANISM: Macaca fascicularis

<400> SEQUENCE: 46
ggcagaagaa accatcccgc tgcrgaccct acgctgct                              38

<210> SEQ ID NO 47
<211> LENGTH: 38
<212> TYPE: DNA
<213> ORGANISM: Cavia porcellus

<400> SEQUENCE: 47
ctcagaggac accgtcccgc tgcagaccct gcgctgct                              38

<210> SEQ ID NO 48
<211> LENGTH: 38
<212> TYPE: DNA
<213> ORGANISM: Rattus norvegicus

<400> SEQUENCE: 48
ggcagaagaa actgtccctc tgaagactct gcagtgct                              38

<210> SEQ ID NO 49
<211> LENGTH: 38
<212> TYPE: DNA
<213> ORGANISM: Mus musculus

<400> SEQUENCE: 49
ggcagaagaa acggtccctc tgaagactct gcagtgct                              38

<210> SEQ ID NO 50
<211> LENGTH: 957
<212> TYPE: DNA
<213> ORGANISM: Homo sapiens

<400> SEQUENCE: 50
caccactaaa aatgagcaat gccaatgggt ggagagcccc taaagcagca ctaattgcaa      60
ggatttctca ggtgactggt tagtatgtgg tgtcaatcat gaaaagaag aactgcacga     120 aagtatcttt ctgaaaactt gcaaaactga gaagctagtc tgtttaaaac aggaagttat     180
atacttacat tgtttactac tttactaatg tctgtgatct gatggtatct ctgtttcagg     240
agtggtgacg cctaagctat cactggacat atcaaggact tcactaaatt agcaggtacc     300
actggtcttc ttgtgcttat ccgggcaaga acttatcgaa atacaataga agttttact      360 tagaagagat tttcaggtag gtgtcgcttt tccaggaaaa gggaggtgga acaaggaggg     420
gtccaggcag gtgaagtag taacttccag cagtgctctt ggatctagga gggaggagag     480
gaaggtacac agcaatttag aggtagtatg gggccagagt gggagaaaat atggccacat    540
```

| | | |
|---|---|---|
| atctccattt tcttcttgct ttttctaatt ttcccttcct gtctcccatc cacacaatga | 600 | |
| taagtttgcg tgtagcactc acccaaactt ggccctttat acctctttag tcaacatctg | 660 | |
| tgcccatgtt accctcctat actttcacaa attctcaact atgtgcatat gactactcca | 720 | |
| aagagcttac acttaatagc ttgtgtttat ttatattgac ttgtaagaaa tagcaaaaat | 780 | |
| ataatttac atatatatgt gtatatatat atatatacac atatatatat atatatat | 840 | |
| atacacatat atatatatat atatatatac acatatatat atatatatat atacacat | 900 | |
| atatatatat atatatatat ataccacaca cacacataca tttttatata tacaaag | 957 | |

<210> SEQ ID NO 51
<211> LENGTH: 1453
<212> TYPE: DNA
<213> ORGANISM: Homo sapiens

<400> SEQUENCE: 51

| | | |
|---|---|---|
| gggtgaatac ctgctctgtg cccagtgcca tgctaggtcc caagggacac atcagcacat | 60 | |
| acagcaggca catggctctg ccctgtgacg ctttgccctg agacatggct ctgccctatg | 120 | |
| acgcttatgt cacagtggca ttctacccac actttacatt tccttagccc tgtatattct | 180 | |
| gcagagactt ttcacatatt tatcttagtt ggttccacgg caatgctatg acttaaatat | 240 | |
| cattatttcc agtttagaga tgaaaaagct gaggtccagc aagtttaaat tactacccc | 300 | |
| agcttatgta gctgtgtatg ccacaactga aactcaaact caagtctttt agacttgtct | 360 | |
| aaacctttgc agccacattt tgccccatcc aagtgtctac tggaccctgc agaataatta | 420 | |
| gtttattcct ttgccgggaa attcttattt cattcttcat cctgtctccc gatgagtcaa | 480 | |
| atcaatgctt attcaagaat tataaatccc aggtctttag gaggccgaga ctcgcagatc | 540 | |
| acttgaggtc agaagtttga ccagcctg gccaacatgg tgaaaccctg tctctactaa | 600 | |
| aaatacaaaa attagccagg catggtggca tgtgcctcta ataccaacta ttccagaggc | 660 | |
| tgaggcagga aaatcccttg aacccaggag gtggaggttg cagtgaactg agatcatgcc | 720 | |
| actgtactcc agcctgggtg acagaatgaa atcccgtctt aaaaaaaaaa aaattataac | 780 | |
| aaccccccac cactaaaaat gagcaatgcc aatgggtgga gagcccctaa agcagcacta | 840 | |
| attgcaagga tttctcaggt gactggttag tatgtggtgt caatcatgaa aaagaagaac | 900 | |
| tgcacgaaag tatctttctg aaaacttgca aaactgagaa gctagtctgt ttaaaacagg | 960 | |
| aagttatata cttacattgt ttactacttt actaatgtct gtgatctgat ggtatctctg | 1020 | |
| tttcaggagt ggtgacgcct aagctatcac tggacatatc aaggacttca ctaaattagc | 1080 | |
| aggtaccact ggtcttcttg tgcttatccg ggcaagaact tatcgaaata caatagaagt | 1140 | |
| ttttacttag aagagatttt caggtaggtg tcgcttttcc aggaaaaggg aggtggaaca | 1200 | |
| aggagggggtc caggcaggtg gaagtaataa cttccagcag tgctcttgga tctaggaggg | 1260 | |
| aggagaagga aggtacacag caatttagag gtagtatggg gccagagtgg gagaaaatat | 1320 | |
| ggccacatat ctccattttc ttcttgcttt ttctaatttt cccttctgt ctcccatcca | 1380 | |
| cacaatgata agtttgcgtg tagcactcac ccaaacttgg cctttatac ctctttagtc | 1440 | |
| aacatctgtg ccc | 1453 | |

<210> SEQ ID NO 52
<211> LENGTH: 5791
<212> TYPE: DNA
<213> ORGANISM: Homo sapiens

<400> SEQUENCE: 52

```
ttcttcctaa atttatttac aaatgtaaca caattccacc caaacttatg tttttataag      60
taattgagta gatgatccta aagtttaata aaacaaatgg ctctaatagg taagacattt     120
ggaaatgtat aatgaaaggg agttgcataa taagatcatc tatataaatc atctaataaa     180
tctacaataa aaagtgtctc tagcacagaa ataagatatc aatagaatat aaggtacaaa     240
atcagattca ggaacattaa agaatatacg acaaaggtga tatttcaagc ccaaagggga     300
gaagatggtt attcaacaca tagtgtttta aaatttgtca gataagaatg agaggagga     360 ggctcctctc ctctgacccc agggaatgtg agaagagaca cagtggttat gaaggaagc     420 agtcacacct gtggatccct accttcccca tcagagctag ggggcatgga gcgctctctg     480
ctaagatggg gacccccaag gaatgtctcc ctgtggggca cttccttacc agatgggatg     540
gccagtgcgg ttaagttggt ggtcaggcag aaaaaaaaga tctagtttgt actcttgaga     600
gttcctcggt ttgttcatgg catgggcagg gagtcaagga gcagcagcct tgcctcagtg     660
cctaccagtg caggaaaagg tgcatagcct gggccaggc cagggccctg gtggaggcgt      720
agtggtaaca gagagggctc tccattccag cccaaggaag actaagaatg aatacctcat     780
gagtatatta gctacaaacc accacagcag gttccgaaaa aaggctcagc gttggaacca     840
ggtcaccccc actcagcaga caccagtcat ataaatcaag gaccaacagg agacaggaac     900
acccccttcc cactctgccc catgtctcaa gttgtagtgg cccttcctcc agatctctgc     960
caccatctta gaaaggaaca ctgaaagaag aaactgaaat tataagctga cagcataaag    1020
aggatgagta aaacctaaaa tcattgttca aatgaatgaa tcaagagaag tttaaaccac    1080
tttggactaa aatgtgtgaa tcctttttcc tgctatccag cagatgagaa gctggtaaca    1140
gagaccaaaa tagtttggag actaaagaat cattgcacat ttcactgctg agttgtattg    1200
tgagtaattt tagttgacct cacttttgta aatcttgcac acgggcatcc atatctgcac    1260
agagatatgt taacagtggt aaatgctgca tgaggagatt gggtgatttt tactttcgtt    1320
tttgtgctct tctttcttat tgttcttact tatttacgat taccctatcg ttttccaaaa    1380
tgtaaaaggc cattttgaaa gcctaattca aacctcttca ctattttgta tctaagtatt    1440
caccttgatt gagactgggt agacaggtga aaaccatatc aggtttttaa ttttttaatt    1500

tttaattatt tatttattta tttatttttt gagatggagt ctggctgtcg cccaggctgg    1560
agtgcagcgg cgtgatcaca gttcactgca gcctcaacct tctaggctca agggattctc    1620
ccacctcagc cccccaagta gttgggacca cacgtatgcg ccaccatgcc tggctaattt    1680
cttatttttt tgtagagata ggatctcact atattgtcca ggctggtctt gaattcctgg    1740
gctcaggtga gcctcccacc tgggcctccc aaagtactgg gattacaggc atgagccaag    1800
gtcccctgcc catatgagat tttctgtctc tgatcccatg cagctagtaa tcaaggactt    1860
ggctgctgac tctggaggac ctgcatgctt tcttgagctg tgaacttcag tgctaaaagc    1920

tcataggcag ccctgaaacc caaccaaaa ggttctatgg tttatcatcc cgatcatgtt    1980
gatttTatag aaataacaca tgaattaaag acactaccct caaactgagc aaaacttaag    2040

taattTTTtt aaagtttgac ctgttTTTaa atcactcttg gagaaaaagg aaaataaata    2100
caaataatta acggtgaata caggctacta taccttgtt ctccagaatt agcagttctg    2160

ttctttTctt gctttagatg ctgaagtgca gaaggacact ctgtgattgt acgtgtgtaa    2220
ctgacaaaat gtgtattttt tttctcagct gctatggatt ggattatgct attatgaata    2280
agaatgctga tgggagcaca cacaaaccat ttgttcctca gtccattttc ctcctcaaaa    2340
gcctggaatg tgccattgat cagtgggaga tgtacctgga cagacccatg aaaagagatc    2400
```

```
aacaagttcc acccaaggga ccctatttt  cctaatttca tttgaaatgg cttctaattg   2460
tccttctttc attcctgctt cctaccagtt ttacagcttt ttctggtttc aaatgtgaac   2520
tcacatacac tctcatttt  cctcatcaca accccaagtg acccaatggt cctcactttc   2580
gatataagta aaggaggctc tgcattaagg gcttgtccaa ggcacgcagc tgagaggcgc   2640
taggactggc tccatttcca tctctattct cactgacttt gactacccag accccaaca   2700 tgtggggcct cagtattcga tcaattattc tattaagaag caaaaacaat tccccgcatt   2760
ggccccagtt attaagcatt tctcagattt accttgagaa atgcccatcg gcctgtatat   2820
tcacatcttc acccttgtcc cttcctccta gaaaggagaa agtcagttgg atgccctctg   2880
aggaactagt gcatggctta actgtcctc  catgactcct gccttatctg ttttctattt   2940
tcctcctttt ccaccgaagt ctataatctc aagaaaagca ggcactggcc ttagggctcc   3000
tggcctaaga aatatcaagt ccagtgagaa atcccattga ctgacccctc ctgcttaccc   3060
ctttgtgatg gagaagctcc caggggtttg cttttgcat  gttaccaggc ctaactcagc   3120
atcaccaggg gcaagaaaag gaaagtaacc taaactaatg ctgcttataa ttgtaattat   3180
tgtaatagtt aattactgtg attgtacatg tgtaacagac aaaatgtgta ttttttcac   3240 agctgctgtg gattggatta tgccatttgg aataagaatg ctgttaagag cacacaagcc   3300
aggttcctca agtccgtagc aaattttca  aaagttaaat ttaaaaatca ctacatttga   3360
atctagtgac aggagaaatg gacatggata gagactaaag atctagccca aattttatat   3420
ttacttgtta gaggattttg aacaaattac taaatttctt caaggttcaa tttccccatt   3480
aactataatg aatggctcat cattatgggg ccctggagaa gcataattac ttgtaattgt   3540
aataatcatt gttattatta ttatacatat tttgcttta  aatggataag gatttttaag   3600
gtatatgtaa actgtaaaac ataaaatgca aaatgccgta agagacagta gtaataataa   3660
tgattattat attgttatca ttatctagcc tgttttttcc tgttttgtat tcttcctttt   3720
aaatgctttc agaaatctgt atccccattc ttcaccacca ccccacaaca tttctgcttc   3780
ttttcccatg ccgggtcatg ctaactttga aagcttcagc tctttccttc ctcaatcctt   3840
ttcctggcac ctctgatatg ccttttgaaa ttcatgttaa agaatcccta ggctgctatc   3900
acatgtggca tctttgttga gtacatgaat aaatcaactg gtgtgttta  cgaaggatga   3960 ttatgcttca ttgtgggatt gtattttct  tcttctatca cagggagaag tgaaatgaca   4020
acctcactag atacagttga gacctttggt accacatcct actatgatga cgtgggcctg   4080
ctctgtgaaa aagctgatac cagagcactg atggcccagt ttgtgccccc gctgtactcc   4140
ctggtgttca ctgtgggcct cttgggcaat gtggtggtgg tgatgatcct cataaaatac   4200
aggaggctcc gaattatgac caacatctac ctgctcaacc tggccatttc ggacctgctc   4260
ttcctcgtca cccttccatt ctggatccac tatgtcaggg gcataactg  gttttttggc   4320 catggcatgt gtaagctcct ctcagggttt tatcacacag gcttgtacag cgagatcttt   4380
ttcataatcc tgctgacaat cgacaggtac ctggccattg tccatgctgt gtttgccctt   4440
cgagcccgga ctgtcacttt tggtgtcatc accagcatcg tcacctgggg cctggcagtg   4500
ctagcagctc ttcctgaatt tatcttctat gagactgaag agttgtttga agagactctt   4560
tgcagtgctc tttacccaga ggatacagta tatagctgga ggcatttcca cactctgaga   4620
atgaccatct tctgtctcgt tctccctctg ctcgttatgg ccatctgcta cacaggaatc   4680
atcaaaacgc tgctgaggtg ccccagtaaa aaaagtaca  aggccatccg gctcattttt   4740
gtcatcatgg cggtgttttt catttctctgg acaccctaca atgtggctat ccttctctct   4800
```

```
tcctatcaat ccatcttatt tggaaatgac tgtgagcgga gcaagcatct ggacctggtc    4860
atgctggtga cagaggtgat cgcctactcc cactgctgca tgaacccggt gatctacgcc    4920
tttgttggag agaggttccg gaagtacctg cgccacttct tccacaggca cttgctcatg    4980
cacctgggca gatacatccc attccttcct agtgagaagc tggaaagaac cagctctgtc    5040
tctccatcca cagcagagcc ggaactctct attgtgtttt aggtcagatg cagaaaattg    5100
cctaaagagg aaggaccaag gagatgaagc aaacacatta agccttccac actcacctct    5160
aaaacagtcc ttcaaacttc cagtgcaaca ctgaagctct tgaagacact gaaatataca    5220
cacagcagta gcagtagatg catgtaccct aaggtcatta ccacaggcca ggggctgggc    5280
agcgtactca tcatcaaccc taaaaagcag agctttgctt ctctctctaa aatgagttac    5340 ctacattta atgcacctga atgttagata gttactatat gccgctacaa aaaggtaaaa    5400 cttttttatat tttatacatt aacttcagcc agctattgat ataaataaaa cattttcaca    5460
caatacaata agttaactat tttattttct aatgtgccta gttctttccc tgcttaatga    5520
aaagcttgtt ttttcagtgt gaataaataa tcgtaagcaa cataatggca tgccattcct    5580
gttctaaata ttcttcatag tttgttgatt tcctgttcac actgaatgac aaaatttccc    5640
atgggtgact cacagagccc tgagaagtgt gcactgtcct cttaatgcca atctgacatt    5700
gcagaggagg ccagggcctc ctgtacatat gaagtagccc gggtatggag cggggaggtg    5760
ttgggcttgc agggactctc ggcacctgta g                                  5791

<210> SEQ ID NO 53
<211> LENGTH: 1272
<212> TYPE: DNA
<213> ORGANISM: Homo sapiens

<400> SEQUENCE: 53
cacgcgtaga ctcccacccc ccccaactca acctcctctc tcgcttgctc gctcgctcgc      60
acgtacgcac gctcgcacgc acgctcgcca tcgctcgtca cccttggtgc catcaccacc     120
acgacgtcgg ccagccaaga agagagtcgg gaggagagag ttggtccgcc cgcccgcttg     180
attgctatag gagtttggtc tgagagcctt tctcatccgg aagatgctgg caatgcacac     240
catgcagccc atgtatgccg agctgcgaga cgcattagcg tcaagctatg acgatgaagc     300
atcattaaca tacagctcgg atacggacaa cagcctgaag tatgatgacc ctttggacat     360
catcgatcag tacatcatac acgagctgca gaagtgcggg aactcagata aaaactttat     420 cagtggggagc gacgtgacgc tgtctgggta cgaaggctcc gagtcctcct accagtccct     480
gctcgatgag ccccacacgg ctccctccgt gccgtctccg acgctgagct cggcggacga     540
cgccgattac gacagcgacg tcccgacgct gcagatctcc gacacggaga gcgaggacga     600
ggaggaggag gaggaggagg gggacgagga gggctgccgg aggaggtgcc gcccggttga     660
gctgccgccc ttcggcagcg tcgctggcgg cgacggccaa cagcagcagc agcagcaggg     720
ccgccaccgc caccaccagc agcaccacca ccagcagcag cagcagcagc tacctcgtgg     780
tgtgaccgtg aagagggaga aaggagtggg gaagcgaggc aagacgaggt tgtaccagtt     840
cctcatggag atcctccagg accagaggat gtgccactgc atctggtggg tggacgagcg     900
ccagggcatc ttccagttct cgtcgcagca caaggaggag ctggcgaaga gtgggccac     960 gcggaagggc aaccgcaagg cgatgaccta ccagaagctg cgcgggcgc tgcggaacta    1020 cgaggcgacg ggcgagatcc gcaagatcaa gaagaagctg acgtaccagt tcggcgccaa    1080 gatgatggc gccttcaggc gatgatgaag aggccgactc cgccgccatc gccacttgtc    1140
```

| | |
|---|---:|
| cacgggccat cgcgctggag ggaagaggga ggagagagag ggcttctctc tcccccgtcc | 1200 |
| gttgccctct gcgcgtggtt ttttgagggg aagcgtcgtg ttgccgcgct tccggaggct | 1260 |
| gcctgtgtgg gc | 1272 |

<210> SEQ ID NO 54
<211> LENGTH: 1497
<212> TYPE: DNA
<213> ORGANISM: Homo sapiens

<400> SEQUENCE: 54

| | |
|---|---:|
| taaggacctc acctcagaac ctattagaga aaagtatgaa aatgtggtag ggcctttctc | 60 |
| ccatcctgag atccatcaca gtacgdggac ttcaaggagt ccaaggatct cattttttgtt | 120 |
| gtatttttttg tttgatgtga ttttttaaagt cagttttctg gatgtttgaa aattgaagtc | 180 |
| agaacattcg ctaagaagtt gactgaatgt tgcaagcttg caaaatggaa ggattccccc | 240 |
| tcattccccc tccctctgaa gacatggtaa cctatgagtc agacctctac cgacagcccc | 300 |
| atgactatta ccaatatctc aacagtgatg gagacagtca tggtgagcat tactgggact | 360 |
| atcatccaca ccacatgcac agtgaattttg agaactttgg ggacaatcac ttcacagaac | 420 |
| tccagagtgt acagcctcca cagctgcagc agttgtaccg gcacatggag attgagcaga | 480 |
| tgcacgttct agacttaggg ctccctgccc cacatattgg gctgaaccac caggtctcct | 540 |
| atttgccccg gatgtgccta cagtacccat ctccacacca gcccagttct gatgaggaag | 600 |
| acatggagag gcagagccca ccattggagg tatcagatgg ggagactgat ggtgtagacc | 660 |
| caactcctgg gattatgcat ggagaaccag gcagcaagaa aaaaatccgt ctgtaccagt | 720 |
| tccttctgga ccttcttcgc aatggagaca tgaaagacag catctggtgg gtagacaagg | 780 |
| aaaaaggcac tttccagttc tcctccaaac acaaagaggc actggcaaac cgctggggca | 840 |
| tccagaaggg taaccgcaag aaaatgacct accagaaaat ggcacgggct ttgagaaact | 900 |
| atggcaagac aggggaagtc aagaaggtca agaagaagct gacctaccaa tttagtggag | 960 |
| aggtgatggg aagggcaagc agcgatagga agcattatcc tcactgaata caggtcttgg | 1020 |
| gagcccatgc aagaaaaaga tattacaacc tcctggctgg atgccagtag aggagatgga | 1080 |
| cgcatctttc tcttttcttc ctgtgcccac ctctctacct ttacagggcc cttaacatcc | 1140 |
| gatgttttgg tacgaattcc cttcttcagc atctgagaat cctaaagata acagaattct | 1200 |
| ttgcttctct ccaacaagct ggacagagtt gggaaattta agaaatgtat aaatatatta | 1260 |
| ttgtcagaaa atatttgttc aattgtgttg taattaaaga atacaacttg ttgaagtttt | 1320 |
| gccttcaaag gtggtgctgt gtcaccctgt gacactgcat tagcttacag cttttgaaact | 1380 |
| agcattaata caggctctgc tgcagctctc aacagctaga gagacgtttg cagatcttgg | 1440 |
| aatgatactt attatgttta aatagtaata acttgtatat atttaataaa atttgca | 1497 |

<210> SEQ ID NO 55
<211> LENGTH: 1563
<212> TYPE: DNA
<213> ORGANISM: Homo sapiens

<400> SEQUENCE: 55

| | |
|---|---:|
| tccgcctggc cgttcaccag cccacaccgc tccccaaaga tgcttacact tgaggcatcg | 60 |
| cagcttgatg ggccacaccc cagctacatg ttttccgaca gtagtttcta cgacctggac | 120 |
| tcatgcaagc tctgcgcccac cttcccacac tgcctgatgg aggccgagcc ccccacggat | 180 |
| ccgtgtgcgg gctggctgga gctggcagag ccgggctatg agcccttcga ttcggggcag | 240 |

```
ttggccccgc tgcacaccgt gacggtcccc tacgggcatg gccctaccc accagccccc      300
tcggacgcca tctacagcct ggaggggccg ctgcctgccc ctagccactg cccgtcctg      360
cccgaggagt acggagccca gccctacacg ctgtacagtc catgccccct gcccagcacc      420
ccgctctcgg aggatgacga cttccccact gatgccccgg ccctggaggt gtctgacagc      480
gactcagatg agaacctgtc acctggcggg tctctggacc tcgactcagg ctcgcggcgg      540
aagctgcgcc tgtaccagtt cctgctggga ctgctgcagc gcggtgacat gcaggagtgc      600
gtgtggtggg tggagcacga ctccggcgtc ttccagttct cgtccaagca caaggaggca      660
ctggcacacc gctggggaca gcagaagggc aaccgcaagg ccatgaccta ccagaagatg      720
gcacgggccc tgcgcaacta tgcaagacg ggtgagatcc gcaaggtcaa gaagaagctt      780
acctaccagt ttggccacaa actgctgggg ctgtccggcc ccgcgcccc ctcctaggag      840
cccctgtgcc tgccacggga ctgcacagcc atggcatgg catgccacc aggggggcact      900
gccccacccc tgcccaccg gggtgtctgc tcccggcagg accgggtgcc aggactcctg      960
ggttctctcc tctgcactgg gttcagtggg tgagatggat ggggaggagc caggatgctg    1020
aattcttcta tttcctgtat cccggtggag tttagtttgg ggtggttgg gcaccagaac    1080
acctaggttc catcccccg ctccctcccc tcagagaggg gagtggggcc tagtgaatta    1140
gagcagggag cctggttcca ctccctggct ctggttggag tgtaggttg agcacaagta    1200
cacttgagtt ccacccctgg ctcagagaga ggagtgggta cctatggttt agagcaggga    1260
gctgggaacc agtacacttg ggttccagct ccagctctgg gcagcaaatg gggtgggggt    1320
gggcactaaa gtagggtggg ctggaagcca gggctcctag cttctgttgc cctctggctt    1380
ggcagggtct actcctttgt gtggagtggt cctctccagg tgtgagttca gggagcaacg    1440
tgtatattta tatttcagga gggcatctca gagtttgtat aagttgggtc tttctgtctt    1500
ttttaaagca atcaagtttg tataattttg taaattccta ataaaatgtt gctagaaaag    1560
aaa                                                                  1563

<210> SEQ ID NO 56
<211> LENGTH: 260
<212> TYPE: DNA
<213> ORGANISM: Homo sapiens

<400> SEQUENCE: 56
accactggtc ttcttgtgct tatccgggca agaacttatc gaaatacaat agaagttttt       60
acttagaaga gattttcagg gagaagtgaa atgacaacct cactagatac agttgagacc      120
tttggtacca catcctacta tgatgacgtg ggcctgctct gtgaaaaagc tgataccaga      180
gcactgatgg cccagtttgt gccccgctg tactccctgg tgttcactgt gggcctcttg      240
ggcaatgtgg tggtggtgat                                                 260

<210> SEQ ID NO 57
<211> LENGTH: 2923
<212> TYPE: DNA
<213> ORGANISM: Homo sapiens

<400> SEQUENCE: 57
ctgctccgga gtgacgcggg cccgggcgcg acggtctcgg cggcggcggc ggcggcgaca       60
gagcgagcgc ggcgcggggc caccatgggg gcccagctca gcacgttggg ccatatggtg      120
ctcttcccag tctggttcct gtacagtctg ctcatgaagc tgttccagcg ctccacgcca      180
gccatcaccc tcgagagccc ggacatcaag tacccgctgc ggctcatcga ccgggagatc      240
```

```
atcagccatg acacccggcg cttccgcttt gccctgccgt cacccagca catcctgggc      300 ctccctgtcg gccagcacat ctacctctcg gctcgaattg atggaaacct ggtcgtccgg      360
ccctatacac ccatctccag cgatgatgac aagggcttcg tggacctggt catcaaggtt      420
tacttcaagg acacccatcc caagtttccc gctggaggga agatgtctca gtacctggag      480
agcatgcaga ttggagacac cattgagttc cggggcccca gtgggctgct ggtctaccag      540
ggcaaaggga agttcgccat ccgacctgac aaaaagtcca accctatcat caggacagtg      600
aagtctgtgg gcatgatcgc gggagggaca ggcatcaccc cgatgctgca ggtgatccgc      660
gccatcatga aggaccctga tgaccacact gtgtgccacc tgctctttgc caaccagacc      720
gagaaggaca tcctgctgcg acctgagctg gaggaactca ggaacaaaca ttctgcacgc      780
ttcaagctct ggtacacgct ggacagagcc cctgaagcct gggactacgg ccagggcttc      840
gtgaatgagg agatgatccg ggaccacctt ccaccccag aggaggagcc gctggtgctg      900
atgtgtggcc cccacccat gatccagtac gcctgccttc caacctgga ccacgtgggc      960 caccccacgg agcgctgctt cgtcttctga gggccgggca cggtcacacg gccacccgcc     1020
ccgcgcaccc cacgccctgt tcacgctcac ccagtcacct ccccacatcg cacactgggg     1080
ccccgggttc agcctggcct gcccgtgccc tggtgaatca cctggctgag cagttcccct     1140
ggagcccctt cgggagcagg gctgtgtccc agatgggcca cggctgagcc ttcagagtac     1200
gtcctgcctg gcacttactg gtccttacca gagacgccca gccccatccc tgtcctcatg     1260
acccctcgtc cacccccac acacactata aggctgaggg ctgccagcag cccgtctgc      1320 ccaccattcc cggccgtgga ccatagtcgg gatgtcagca gacacacatg ggcagcccaa     1380
agctgcaggt gccagggccc accccagcct cgcctgtcac cccactccc gcctcagggc      1440 caggcccagg cctcaccacc tgacgctgca tgagacattg acaccagaaa gccctcttgg     1500
gggcactgct ccctacccca gggccctggc cagccgggag cttggctctc ctctggctag     1560
agtgggaaga gggggctggc catggggccc tcccagaacc tcagcatttc cttccagccc     1620
atccaaacac tgaggcagcc ttggggaacc ccgagctggg gggttggcag cccactgcac     1680
cgcctcaggg ttttggggtc ctgggctggg gccaccatcc ctgatggcag aactcccaca     1740
accacatgta tttattcctc tgtcctaaac cgtcccctcc ttccctcacc ccagcacag      1800 ggggattctg agcagtgcct cttgtctgag ggacatatca gtgacctcga cgttgccttt     1860
agactacagt tgtgttagcc tcttgcgtat tggctttttc agagtcattt atgagcagaa     1920
aaaaaaaaag taaaactttg ctaatattaa cccttctcta gctcctcgag ggtctgtgac     1980
ctgcaacaca aggggtgggg tcaggaaagg gctggggaag acctagcatt ttttttttct     2040
tttttttttt tttttgagac ggagtctccc tttgtcaccc aggctggagt ggcatgatct     2100
cagctcacta caacctccac ctctcgggtt caagcgattc tcctgcctca gcctcccgag     2160
tagctgggac taaaagtgcc caccaccaca cccagctagt ttttgtattt ttttttttt      2220 tttttgaga cggagtctcg ctctgtcgcc caggctggag tgcagtggcg ggatctcggc     2280
tcactgcaag ctccgcctcc cgggttcacg ccattctcct gcctcagcct cccaagtagc     2340
tgggactaca gcgcccgcc actacgcccg gctaatttttt tgtatttttta gtagagacgg      2400 ggtttcaccg ttttagccgg gatggtctcg atctcctgac ctcgtgatcc gccgcctcg      2460 gcctcccaaa gtgctgggat tacaggcgtg agccactgcg cccggctcca gcatttattt     2520
ctgatgtatc tttgtggtag aaaatttgga aagtgcagag aagtatacac aggaagaaaa     2580
attcccaacc cccagaggca aaccagctga aaccacgcaa ccccagtcac cccaatgcac     2640
```

```
cgcgaggctg ctgcctcctg tcagggtcag atgagcctcg aggctcagga aagtcagagg    2700
atgccatctg catggtggta aattacagag gtgatgaggc aaggtgggtg tggggctgtt    2760
cttaaaacgg ggcagcagga aggccccaag gagatggatt tgggctggga cgggaagaga    2820
gagctggcca tgctggggtg ggtgggtgtt caaatggtgg aaacagcaga cgcaaaggcc    2880
ctgccgttgg aaccagcttg tggaataaac tttcagaaac aga                      2923
```

<210> SEQ ID NO 58
<211> LENGTH: 1717
<212> TYPE: DNA
<213> ORGANISM: Homo sapiens
<400> SEQUENCE: 58

```
ctgatggtat ctctgtttca ggagtggtga cgcctaagct atcactggac atatcaagga      60
cttcactaaa ttagcaggta ccactggtct tcttgtgctt atccgggcaa gaacttatcg     120
aaatacaata gaagttttta cttagaagag attttcaggg agaagtgaaa tgacaacctc     180
actagataca gttgagacct ttggtaccac atcctactat gatgacgtgg gcctgctctg     240
tgaaaaagct gataccagag cactgatggc ccagtttgtg cccccgctgt actccctggt     300
gttcactgtg ggcctcttgg gcaatgtggt ggtggtgatg atcctcataa aatacaggag     360
gctccgaatt atgaccaaca tctacctgct caacctggcc atttcggacc tgctcttcct     420
cgtcacccct ccattctgga tccactatgt caggggcat aactgggttt ttggccatgg     480
catgtgtaag ctcctctcag ggtttttatca cacaggcttg tacagcgaga tcttttttcat     540 aatcctgctg acaatcgaca ggtacctggc cattgtccat gctgtgtttg cccttcgagc     600
ccggactgtc acttttggtg tcatcaccag catcgtcacc tggggcctgg cagtgctagc     660
agctcttcct gaatttatct tctatgagac tgaagagttg tttgaagaga ctctttgcag     720
tgctctttac ccagaggata cagtatatag ctggaggcat ttccacactc tgagaatgac     780
catcttctgt ctcgttctcc ctctgctcgt tatggccatc tgctacacag gaatcatcaa     840
aacgctgctg aggtgcccca gtaaaaaaaa gtacaaggcc atccggctca tttttgtcat     900
catggcggtg ttttcattt tctggacacc ctacaatgtg gctatccttc tctcttccta     960
tcaatccatc ttatttggaa atgactgtga gcggagcaag catctggacc tggtcatgct    1020
ggtgacagag gtgatcgcct actcccactg ctgcatgaac ccggtgatct acgcctttgt    1080
tggagagagg ttccggaagt acctgcgcca cttcttccac aggcacttgc tcatgcacct    1140
gggcagatac atcccattcc ttcctagtga aagctggaa agaaccagct ctgtctctcc    1200
atccacagca gagccggaac tctctattgt gttttaggtc agatgcagaa aattgcctaa    1260
agaggaagga ccaaggagat gaagcaaaca cattaagcct tccacactca cctctaaaac    1320
agtccttcaa acttccagtg caacactgaa gctcttgaag acactgaaat atacacacag    1380
cagtagcagt agatgcatgt accctaaggt cattaccaca ggccaggggc tgggcagcgt    1440
actcatcatc aaccctaaaa agcagagctt tgcttctctc tctaaaatga gttacctaca    1500
ttttaatgca cctgaatgtt agatagttac tatatgccgc tacaaaaagg taaaactttt    1560 tatatttat acattaactt cagccagcta ttgatataaa taaacatttt tcacacaata    1620
caataagtta actattttat tttctaatgt gcctagttct ttccctgctt aatgaaaagc    1680
ttgttttttc agtgtgaata ataatcgta agcaaca                              1717
```

<210> SEQ ID NO 59
<211> LENGTH: 4848

<212> TYPE: DNA
<213> ORGANISM: Homo sapiens

<400> SEQUENCE: 59

```
gcctagaggc tccagaagaa gactggtctc tcccaccaca cagaggcctg gaggaggcag      60
aggccaggag ggagaggtcc caagagcctg tgaaatgggt ctggcctggc tcccagctgg     120
gcaggaacac aggacttcag gacactaagg accctgtcat gcccatggcc agcacccacc     180
agtgctggtg cctgcctgtc cagagctgac cagggagatg gtgctggccc aggggctgct     240
ctccatggcc ctgctggccc tgtgctggga gcgcagcctg gcaggggcag aagaaaccat     300
cccgctgcag accctgcgct gctacaacga ctacaccagc cacatcacct gcaggtgggc     360
agacacccag gatgcccagc ggctcgtcaa cgtgaccctc attcgccggg tgaatgagga     420
cctcctggag ccagtgtcct gtgacctcag tgatgacatg ccctggtcag cctgccccca     480
tccccgctgc gtgccagga gatgtgtcat tccctgccag agttttgtcg tcactgacgt      540
tgactacttc tcattccaac cagacaggcc tctgggcacc cggctcaccg tcactctgac     600
ccagcatgtc cagcctcctg agcccaggga cctgcagatc agcaccgacc aggaccactt     660
cctgctgacc tggagtgtgg cccttgggag tccccagagc cactggttgt ccccagggga     720
tctggagttt gaggtggtct acaagcggct tcaggactct gggaggacg cagccatcct      780
cctctccaac acctcccagg ccaccctggg gccagagcac ctcatgccca gcagcaccta     840
cgtggcccga gtacggaccc gcctggcccc aggttctcgg ctctcaggac gtcccagcaa     900
gtggagccca gaggtttgct gggactccca gccaggggat gaggcccagc ccagaacct      960
ggagtgcttc tttgacgggg ccgccgtgct cagctgctcc tgggaggtga ggaaggaggt    1020
ggccagctcg gtctcctttg gcctattcta caagcccagc ccagatgcag gggaggaaga    1080
gtgctcccca gtgctgaggg aggggctcgg cagcctccac accaggcacc actgccagat    1140
tcccgtgccc gaccccgcga cccacggcca atacatcgtc tctgttcagc caaggagggc    1200
agagaaacac ataaagagct cagtgaacat ccagatggcc cctccatccc tcaacgtgac    1260
caaggatgga gacagctaca gcctgcgctg ggaaacaatg aaaatgcgat acgaacacat    1320
agaccacaca tttgagatcc agtacaggaa agacacggcc acgtggaagg acagcaagac    1380
cgagaccctc cagaacgccc acagcatggc cctgccagcc ctggagccct ccaccaggta    1440
ctgggccagg gtgagggtca ggacctcccg caccggctac aacgggatct ggagcgagtg    1500
gagtgaggcg cgctcctggg acaccgagtc ggtgctgcct atgtgggtgc tggccctcat    1560
cgtgatcttc ctcaccatcg ctgtgctcct ggccctccgc ttctgtggca tctacgggta    1620
caggctgcgc agaaagtggg aggagaagat ccccaacccc agcaagagcc acctgttcca    1680
gaacgggagc gcagagcttt ggccccagg cagcatgtcg gccttcacta gcgggagtcc    1740
cccacaccag gggccgtggg gcagccgctt ccctgagctg gaggggggtgt tcctgtagg    1800
attcggggac agcgaggtgt cacctctcac catagaggac cccaagcatg tctgtgatcc    1860
accatctggg cctgacacga ctccagctgc ctcagatcta cccacagagc agccccccag    1920
cccccagcca ggcccgcctg ccgcctccca cacacctgag aaacaggctt ccagctttga    1980
cttcaatggg ccctacctgg ggcgccccca gccgctccc ctacctgaca tcctgggcca    2040
gccggagccc ccacaggagg gtgggagcca gaagtcccca ccctccaggt ccctggagta    2100
cctgtgtctg cctgctgggg ggcaggtgca actggtccct ctggcccagg cgatgggacc    2160
aggacaggcc gtgaagtgg agagaaggcc gagccagggg gctgcaggga gtccctccct    2220
ggagtccggg ggaggccctg cccctcctgc tcttgggcca agggtgggag acaggaccaa    2280
```

```
aaaggacagc cctgtggcta tacccatgag ctctggggac actgaggacc ctggagtggc   2340
ctctggttat gtctcctctg cagacctggt attcacccca aactcagggg cctcgtctgt   2400
ctccctagtt ccctctctgg gcctcccctc agaccagacc cccagcttat gtcctgggct   2460
ggccagtgga cccctggag ccccaggccc tgtgaagtca gggtttgagg gctatgtgga    2520
gctccctcca attgagggcc ggtccccag gtcaccaagg aacaatcctg tccccctga    2580 ggccaaaagc cctgtcctga acccagggga acgcccggca gatgtgtccc caacatcccc   2640
acagcccgag ggcctccttg tcctgcagca agtgggcgac tattgcttcc tccccggcct   2700
ggggcccggc cctctctcgc tccggagtaa accttcttcc ccgggacccg gtcctgagat   2760
caagaaccta gaccaggctt ttcaagtcaa gaagccccca ggccaggctg tgccccaggt   2820
gcccgtcatt cagctcttca aagccctgaa gcagcaggac tacctgtctc tgcccccttg   2880
ggaggtcaac aagcctgggg aggtgtgttg agacccccag gcctagacag gcaaggggat   2940
ggagagggct tgccttccct cccgcctgac cttcctcagt catttctgca aagccaaggg   3000
gcagcctcct gtcaaggtag ctagaggcct gggaaggag atagccttgc tccggccccc    3060
ttgaccttca gcaaatcact tctctccctg cgctcacaca gacacacaca cacacacgta   3120
catgcacaca ttttcctgt caggttaact tatttgtagg ttctgcatta ttagaacttt    3180
ctagatatac tcattccatc tcccctcat ttttttaatc aggtttcctt gcttttgcca    3240
tttttcttcc ttctttttc actgatttat tatgagagtg gggctgaggt ctgagctgag   3300
ccttatcaga ctgagatgcg gctggttgtg ttgaggactt gtgtgggctg cctgtccccg   3360
gcagtcgctg atgcacatga catgattctc atctgggtgc agaggtggga ggcaccaggt   3420
gggcacccgt gggggttagg gcttggaaga gtggcacagg actgggcacg ctcagtgagg   3480
ctcagggaat tcagactagc ctcgattgtc actccgagaa atgggcatgg tattggggt    3540 cggggggcg gtgcaaggga cgcacatgag agactgtttg ggagcttctg gggagccctg    3600
ctagttgtct cagtgatgtc tgtgggacct ccagtccctt gagaccccac gtcatgtaga   3660
gaagttaacg gccaagtgg tgggcaggct ggcgggacct ggggaacatc aggagaggag    3720
tccagagccc acgtctactg cggaaaagtc aggggaaact gccaaacaaa ggaaaatgcc   3780
ccaaaggcat atatgcttta gggccttttgg tccaaatggc ccgggtggcc actcttccag   3840
atagaccagg caactctccc tcccaccggc cacagatgag gggctgctga tctatgcctg   3900
ggcctgcacc agggattatg gttcttttaa atctttgcct ttcagataca ggaaaaataa   3960
tggcattaaa ttgctttaat ttgcattatt ttagttatcc agtttgcaca tatttttata   4020
ggtatcttag gcatcgattg gtattttta actgggccaa gcccattaag gtctttcttc    4080
tgttgggtgc tatcattttc tgattaagtc tttttgacta ttgacataca gtctttcaca   4140
gatggtggag tgttttccc ccaaatctgt tgtttgtctt ataatgttgt atatgaggtt    4200
ttatggtgta tgaatatgaa tgcttctgta atgtcaaaca gatccctagt aaactccttc   4260 ttcacttta ctgtcagatt tacaaaggtc ctcccattgc aaagcagtgt ttgtcctaat    4320
ttatatattg ttttctagt tcattttgtg tttccaactt ttcatgtaaa attttaatta    4380
tttttgaatg tgtggatgtg agactgaggt gccttttggt actgaaattc ttttccatg    4440 tacctgaagt gttactttg tgatatagga atccttgta tatatacttt attggtccct     4500
aggcttccta ttttgttacc ttgctttctc tatggcatcc accattttga ttgttctact   4560
tttatgatat gttttcataa gtggttaagc aagtattctc gttactttg ctcttaaatc    4620 cctattcatt acagcaatgt tggtggtcaa agaaaatgat aaacaacttg aatgttcaat   4680
```

```
ggtcctgaaa tacataacaa cattttagta cattgtaaag tagaatcctc tgttcataat    4740
gaacaagatg aaccaatgtg gattagaaag aagtccgaga tattaattcc aaaatatcca    4800
gacattgtta aagggaaaaa attgcaataa aatatttgta acataaaa                 4848

<210> SEQ ID NO 60
<211> LENGTH: 2711
<212> TYPE: DNA
<213> ORGANISM: Cavia porcellus

<400> SEQUENCE: 60
cagagcccac caggagatgg cgccgcgccc aggactgctc ctcatggccc tgctgcttct      60
gtgcaggggg cccagggtgg aaggctcaga ggacaccgtc ccgctgcaga ccctgcgctg     120
ctacaatgac tacaccagcc gcatcgtgtg cagctgggcg gcggaggcgg ccgctgagca     180
gctcatcaat gtgaccctcc atcgccatcg caggttgtta aaatcgaacc attccgaggc     240
ggtgtcctgc gagctcactg aggacatgcc ctggtcacac tgcccgtctt ctccttgtgt     300
gcctagaaga tgcgtcattc cctacactgc cttcgccctg gctgataatg actactactc     360
attcgagcca gaccggcctc tggacatcag gctcactgtg acgctggccc agcatgtaca     420
gccacctccg ccccaggacg tccagatcaa cacctctggg gaccaagtcc tgctgacctg     480
gagtgtggcc cttgagggtc cccacacgtc ctggctgtcg cagagggacc tggagttgta     540
agtggtctac aaaaggcttc atgagccctg ggagagtgcc agcaccctgc actccaactc     600
ctcccaggcg gccctgggc ccgagctctt cctgcccagc agcacctacg tggcccgagt     660
gcggacccgg ctggcccggg gctccggctt ctcgggaagg cccagccagt ggagccccga     720
ggtgagctga agctcgcagc caggggacca ggcccagccc cagaacctgc agtgcgtctt     780
cgatggggcc cacacgctca gctgctcctg ggaggtgagg tcgcaggtga ccagctcggt     840
ctcctttggc ctcttctaca gatccagcct ggatgcaggg gagcaggaat gtccccaggt     900
gcagaaggag gagctccatg acatctatac ccgacactct tgccagattc gggtgtccaa     960
ccccaggcct cacagccagt acactgtgac cgtgcgtccg cggaatgggg agaaattcat    1020
aaggagcgca aaccacatcc agatggcagc cccaaccctc aatgtgacca aggatggtga    1080
cacctacagc ctgcgttggg tgaccgagaa aatgtactat ccccacatcg agaacacctt    1140
cgagatccag tacaggacag cggggggaccg ctgggagaac agcaagactg agaccctgaa    1200
gaacgcccac aacatgcccc tgccacccct ggagcccgcc accacctacc tggccagggt    1260
gagggtcaaa cccagccctg aggcgcccta caatgggatc tggagcgagt ggagtgagga    1320
gcagcgctgg accacggact gggcgctgcc cacctgggtg ctggccctcg tcctggtctt    1380
ggtcaccctg gccctgctgc tggccctgcg cttctgtggc ctctacgggt acaggctgaa    1440
caggaagtgg aaagagaaaa tccccaaccc cagcaagagc cacctcttca agaatggaag    1500
cgctgggctc cggctcccag acagcaggat ggccttcgcc agcaggagcg ccccttcctg    1560
gggcgtcatg ggtggccgct tccttgagat agagggggtg tgccctgcag attcccggga    1620
cagtgaggtg tcacctctta ccacagagga ccccacagtt gtctgtgatc ctccatcaga    1680
gcctcattcc actccagccg cctcggacct gacccaagag cagcccccta gtgtccagcc    1740
aggtccacca gtccccaag accagcctgg ggaccagctg ccaccttgg actttaatgg      1800 cccctacttg gggccgcccc acagccactc cctgcctgac ctcgcaggcc agcaagggcc    1860
caagcccgaa ctgccaggct ctctggagta tctatgtctc cccccagggg gacgggcgca    1920
gctggtcccc ctggcccagg ccacaggcca ggcccagcct gccctgggg agtgtctgtc     1980
```

-continued

```
tggacctgtc acccagggca gcccctacct ggaagctggg ggaggccctg cccctcctgc      2040
atctgaccct ggaagccagg cacagggccc aggggacggc caggggata gcccagtcat       2100
tctgcccaca aactcagggg gccctgagca ccctgtcgtg gcctctggtt atgtcaccac      2160
tgcagacctg gcactcacct tgtccacaga ggcctcctct gtctccctgg ctcccctcc      2220
agacctctgc ccagggctgt ctgatgaggc cctgcagcc cccacacctg ggaagccacg     2280
ctttgagggc tacgtggagc tccctgcaag catggggcca ttgcccaagt cctttctggg    2340
cggttttgtc cctcctgcac ccagcagccc tgttctgagc ccaggactc cccagggtga     2400
tgtgtccccg ctatctccag cccctgaggg gctgcttgtc ctgcagcagg tagggggacta  2460
ctgcttcctg cctggcctag gatctggtcc cctctcacct cggagcaagc cgtcctcccc   2520
ggtaccctgt ccagaaatca tggacataga gcagggttc ccagtcaaga accccccagg    2580
ccagcctatg cctcaggtgc ctgctattca gttcttcaag tccctgaagc agcaggacta   2640
cctgacactg ccccccctggg aggtcagcag gccccatgag gtgtgctgag gacaccacat  2700
ccttcgctgc a                                                         2711
```

<210> SEQ ID NO 61
<211> LENGTH: 2905
<212> TYPE: DNA
<213> ORGANISM: Rattus norvegicus

<400> SEQUENCE: 61

```
cgcaagtaca gagcaccaga ggatgcagac tagcagtgaa gaatcacaag acctgtaaca     60
tgagtgcggc ccaaccccca gccaagcttt gacacagaac cccaggacaa tgaggacacc    120
accctgccca tagctccctg tgcagccacc taaagtgcca aaatggacca gcacatggca    180
tttatctggg ggctgtgcta catggccctg gtggctctct gctggagaca cggggtaaca   240
aaggcagaag aaactgtccc tctgaagact ctgcagtgct acaacgacta tatcgagcgc   300
atcatctgca gctgggccga cacggaggac gcccagggggc tcgttaacct gaccctctat  360
cactggctag acaagaaaca gccaatgtcc tgtgagctca gtgaggacct catgtggtca   420
gagtgcccgt catcccaccg ctgtgtgcct agaagatgtg tcctccccta tacacagttt   480
tccgtctcaa aagaagacta ctactcactc cagccggatc gtgatctgag tatccatctc   540
gtggttccgc tggcccagca tgtgcagcca ccacctccca aggacatcag catcagcccc   600
tctggggacc atttcctgct gaagtggagt gtgcccctg gggatgccca ggtctctctg   660
cttttcacaaa aggacataca gtttgaggtg gcttataagc agcttcagga ctcctgggag  720
gatgcctcca gcctccacac ttgcaacctc tgggtcactc tcgagccaaa gctcttccta  780
cccaacagta tctatgtggc ccgcgtgcgc gctcagctag cccccaggttc gagcttgtcc  840
ggaagaccca gcggatggag cccagaggta cactgggact ctccgacaga ggacaaggct  900
cggccacaga accttcagtg cttcttttgat gggatccagt ccctcaactg ctcctgggag  960
gtgtggacca aggtgactga ctctgttttcc tttgggctct ctatagctc cagtcccaaa 1020
gctggggaga agaaatgctc tccagtggtg aaggagctgc aggccagccg ctacacccgg  1080
taccactgca gcctaaatgt gtccgacccc gctgcacaca gccagtacac cgtctctgtt 1140
aagcggctgg aacaagggaa gttcatcgag agctttaacc acatccagat gaatcctcca 1200
acctcaacc tgaccaagaa cagagacagc tacagcctgc attgggagac tcagaaaatg 1260
tcctatccat tcatccagca tgcattccag gtccagtaca agaagaaact ggaccgctgg 1320
gaggacagca agacagagaa cctaaatcat gcccacagca tggacctgcc acagctggag 1380
```

```
cctggcacct catactgcgc cagggtgagg gtcaagacca tccctgaata caaagggctc    1440
tggagcgagt ggagcaatga gtgcacctgg acgactgact gggtgatgcc aacattgtgg    1500
atagtcctca tcctggtctt cctcatcctc accttcctcc tggccctccg ctttggctgc    1560
atctatgggt gcaagttgta cagaagatgg aaggagaaaa tccccaaccc cagcaagagc    1620
ctccttttcc aggatggagg taaaggactc tggcctcctg gcagcacggt gaccttctcc    1680
agtaagaacc ccactcccca ggggccacag aacaaccttt tctctgagct acaggggtg     1740 tcatatacac atctggagga caacgaagtg tcacctctca ccatagagga ccccaacatt    1800
attcgagatc catcatctgg ccctgataca accccagctg cctcatctga acccatggag    1860
cagtcttcca atgttcaagt agacccacca actctttctg gcagacccag aagcaatta     1920 cccagctttg acttcaatgg cccgtacctg gggcctcccc aatcccactc cctgcccgat    1980
ctcccaggcc agctggtttc ccccaggggg gttggaagcc tgaagccagc actgccaggc    2040
tccttggagt acatgtgtct gcccctggagg ggcaagtgc aactggtccc actgtcccag    2100 gtgatgggc agggccggga tgtggatgtg cagtgtgggt ccagcctgga gaccacagag     2160
agcccttcca tggaatcaag ggagagccct ccagttgagc tgaaggagga ggaacaggag    2220
ccaagggaca acccagtgac tctccccata agctctggag ccccaaaga cagtaaggtg     2280 gcctctgagt atgtcacacc tgcagatctg gtgctcactc tgcccacaga gcccttgtct    2340
acctctctgg gtccctctct agaggtctcc tcagcccaaa gccccagtct ctgtctcaag    2400
ctgcccaggg tccttctga aagtccagct cttgcaccag cagtgtttga agattacgtg     2460
gagctgcctc caagcatgag ccagcctgcc aagtcccttc caggcaatcc tgctcctcct    2520 gggcaagca gccccgcagt gagcccagga gagcccaggg aggaagtagg cgcagccccc     2580
acacaccctg aaggcctcct tgttcttcag caggttgggg actactgctt cctccctggc    2640
ctgggaccca gccccctctc accaccagt aagccaccct ctccgggcct gtgtctcgag      2700
actgaggacc tagacaagga cttgtctgtc aaaaagcttc cctaccaacc catacccag      2760 gtgccagcca ttcagttttt caagtcccta agcatcagg actacctgtc actgcccct       2820 tgggacaata gccagcctgg gaaggtgtgc tgagtctccc ccctcccaat ctcaccagca    2880
gccctgcgcc tcagcctgtg gacct                                            2905
```

<210> SEQ ID NO 62
<211> LENGTH: 3113
<212> TYPE: DNA
<213> ORGANISM: Mus musculus

<400> SEQUENCE: 62

```
gagctgactg ggagatggtg gggagcgagc tactctggca gaactaaatg tcatggggca    60
cagataaata ggaagagcct gcaactcact ggcacttgga ggctcccgaa ggaggctgcc    120
tgtcgcccaa gcacagagcc acaaaggatg cagtctagga gggaagaatc acaagccctg   180
taagatgagt ggagccaaac ccccagccaa gcaccaatac agaacccccgg acaatgagg    240 acaccccct gcccatagct tccagtgcag ccaccaaaag tgccaaaatg accagcaaa      300 tggcactcac atgggggctg tgctacatgg cactggtggc tctctgttgg ggacacgggg   360
tgacagaggc agaagaaacg gtccctctga agactctgca gtgctacaat gactacacca   420
accacatcat ctgcagctgg gcggacacag aggatgccca ggggctaatc aacatgaccc   480
tctatcacca gctagagaaa aaacagccag tgtcctgtga gctcagtgag aaactcatgt    540
ggtcagagtg cccgtcatcc caccgctgtg tgcccagaag atgtgtcatc ccctatacac   600
```

```
gattttccat cacaaacgaa gactactact ccttccggcc agatagtgat ctgggcatcc    660
agctcatggt gccacttgcc cagaatgtgc agccaccact tcccaagaac gtcagcatca    720
gctcctctga ggatcgtttc ctgctggagt ggagtgtgtc ccttgggat gcccaggtct     780 cctggctttc atcaaaggac atagagtttg aggtggctta agcggctt caggactcct      840 gggaggatgc ctacagtctc cacactagca aatttcaggt gaatttcgag ccaaagctat    900
tcctacccaa cagcatctat gcgcccgtg tgcgcactcg gctgtacccg ggttcaagct     960
tgtctgggag acccagcaga tggagcccag aggctcactg ggactcccag ccaggggaca   1020
aggcccagcc acagaacctt caatgcttct ttgatgggat ccagtccctc cactgctcct   1080
gggaggtgtg gacccagacg actggctctg tttcctttgg gctcttctat cgccccagcc   1140
ctgtagctcc ggaggagaaa tgctctccgg tggtgaagga gccgccgggg gccagtgtct   1200
acacccgcta ccattgcagt ctacctgtgc ctgagcccag tgcacacagc cagtacacag   1260
tctctgttaa gcacctggaa caagggaagt tcatcatgag ctataaccac atccagatgg   1320
agcctccaac cctcaacctg accaagaaca gagacagcta cagcctgcat tgggaaactc   1380
agaagatggc ttactcattc attgagcaca cattccaggt ccagtacaag aagaaatcgg   1440
acagctggga ggacagcaag acagagaacc tagatcgagc ccatagcatg gacctctccc   1500
agctggagcc agacacctca tactgcgcca gggtgagggt caagcccatc tctaactacg   1560
atgggatctg gagcaagtgg agcgaagagt acacttggaa gactgactgg gtgatgccca   1620
cgctgtggat agtcctcatc ctggtctttc tcatcctcac cttgctcctg atccttcgct   1680
ttggctgtgt ctctgtatac aggacgtaca ggaagtggaa ggaaaagatc cccaaccccca  1740 gcaagagcct cctgttccag gatggaggta aaggtctctg gcctcctggc agcatggcag   1800
ccttcgccac taagaacccc gctctccagg ggccacagag caggcttctt gctgagcaac   1860
agggggagtc atatgcacat ttggaagaca caacgtgtc acctctcact atagaggacc    1920
ctaatataat tcgagttcca ccatccgggc ctgatacaac cccagctgcc tcatccgaat   1980
ccacagagca acttcccaat gttcaagtag agggaccaac tcctaacaga cctaggaagc   2040
aattacccag ctttgacttc aatgggccct acctggggcc tcccaatcc cactctctgc     2100 ctgatctccc agaccagctg ggttcccccc aggtgggtgg gagcctgaag ccagcactgc   2160
caggctcctt ggagtacatg tgtctggccc ctggaggtca agtgcaactg gttccattgt   2220
cccaggtgat ggggcagggc caggctatgg atgtgcagtg tgggtccagc ctggagacct   2280
cagggagccc ttctgtggag ccaaaggaga accctccagt tgagctgagc atggaggaac   2340
aggaggcacg ggacaaccca gtgactctgc ccataagctc tgggggccct gagggcagta   2400
tgatggcctc tgattatgtc actcctggag atccggtgct cactctgccc acagggcccc   2460
tgtctacctc tctgggcccc tctctagggt tgccctcagc ccaaagcccc agtctctgtc   2520
ttaagctgcc cagggtcccc tctggaagcc cagctctagg gccaccaggg tttgaggact   2580
atgtggagct gcctccaagt gtgagccagg ctgccaagtc ccctccaggc catcctgctc   2640
ctcctgtggc aagcagcccc acagtgatcc caggagagcc cagggaggaa gtgggcccag   2700
catccccaca tcccgaaggc ctccttgttc ttcagcaggt tggggactac tgcttcctcc   2760
ctggcctggg acctggctcc ctctcaccac acagtaagcc accctctcca agtctgtgtt   2820
ctgagactga ggacctagtc caggacttgt ctgtcaaaaa gtttccctat cagcccatgc   2880
cccaggcgca agccattcag ttttcaagt ccctaaagca tcaggactac ctgtccctgc     2940
ccccttggga caatagccag tctgggaagg tgtgctgagt ctgtctcctc ccaatctcac   3000
```

```
cagcagcctg gcaccgcagc ctgtggtcct cagcctgagc atcaccacag aagcctctct   3060
gagttcacac tcctccttgc tcccagccct gacatggcaa taccccacc tgt            3113

<210> SEQ ID NO 63
<211> LENGTH: 1803
<212> TYPE: DNA
<213> ORGANISM: Pan troglodytes

<400> SEQUENCE: 63
gatgttcctg agcaacagga ccagacagca tcgtgtctca ggccttagac aggagccctg     60
gtccaggccc aggcccaggc cctggcggtg ggcaaagggg gtggggagtg tgagtgtggg    120
gtgggtgggg agcttctccc tggtcccctg ttgtgtcaga gcagcaggaa gcaggtcaca    180
aggaggggca ggatggtctt tgaggagaat ggagaaggtc cgacagaggc gccctggaga    240
actgaaggcg gtggaggggt gggggtggca gagccggccc cgcccccaa cgctggggtg     300 acctccaatg ggttgtcatc tgcctctccg gttccagctc tttaattatt taatttatgg    360
ctgatttagg ccctggccaa caccccagag cgattctggt cccctTcccT tgtggcacgt    420
gcccaggaga gcttgggtgg gagaggtggc agcccacata cggagggggg gcctgggaga    480
gcgcggagcc ccctcccaga cacgtccaca cagcttgctc tgccactgtc taccccgtgg    540
ccagggctgg cacctcacct ccagggcctc agtttTccca tctgtgaact cccaggctag    600
cgccatctct ccctggtcta ctctggacag gcaggcagtg gcacagctgg ggcttcgtgg    660
cctggccctg cccacctcac agtgaggagg aactaagata ggtcacgtgg ggcaattgtg    720
ttaaattgtg atgaaacaag agaagatttt caccattgtc accaccacca ttgtcaccaa    780
caacatcagt gtaggaggca ctccgcagaa accccaggtc agacggcagc acccggcctc    840
gcaggtgcct ggcggagcag gaggtcttgc agggcctccc tcctcctctg tccctgtcc     900 actcccaccc cgaggctgac ctgacaggtc cctctctaca ctgtcacccc atgccaggca    960
caggggacgt cgtagcccct gcccgtggcc cccgcaccca gcatcactca ctcattcacc   1020
cggcgaatga gggtcacgtt gacgagccgc tgggcatcct gggtgtctgc ccacctgcag   1080
gtgatgtggc tggtgtagtc gttgtagcag cgcagggtct gcagcgggat ggtttctgac   1140
aagaggggta gaaggcggtc acctctcttt tctgcaggga cccttgtcac catcacccc    1200 agctgctttg gatgcccag ctctggggag gggtctccca gctccctgca gaggcaccag    1260
gtggccaggc acatgtacac gtgttcatgt ctgccggagt gggctcctgg ttgcggaccc   1320
tcctctcctg gcagaagcac gatattctgt tggttctcag cacgctttct gggcctctgc   1380
agtgtgctgt tcctgggcac ggtccctccc cccaccccag gaccgggaca tgcatcaagc   1440
acaggcctgg cccctggacc gactgtgcag cctggagggg ggcacacact cagccctggg   1500
atgcagcgtg gcagagttct accctgcacc ctcccgcctc ctctctagtc cccatcctca   1560
ggagcctggt atttgttaag gggactgtgg tcccagcatt atcacagaag ccaggtctct   1620
gggagccctt ggagggggcc gtttcacctc aagagcccag gagcatccca gtgcgggctt   1680
caggcacaag gagggtgcta gcggctgaag caggagaga accccagcca aggccctgca    1740
ggagcaaagt cccggaggtg ggaaaaactg aggcgcagac agagtctgct gggaaggagg   1800
gac                                                                1803
```